United States Patent
Delhem et al.

(10) Patent No.: US 10,899,838 B2
(45) Date of Patent: Jan. 26, 2021

(54) ANTIBODY WHICH IS DIRECTED AGAINST GALECTIN-9 AND IS AN INHIBITOR OF THE SUPPRESSOR ACTIVITY OF REGULATORY T LYMPHOCYTES

(71) Applicants: Universite de Lille, Lille (FR); CENTRE NATIONAL DE LA RECHERCHE SCIENTIFIQUE—CNRS—, Paris (FR); INSTITUT GUSTAVE ROUSSY, Villejuif (FR); CELLVAX, Romainville (FR); UNIVERSITE PARIS-SUD, Orsay (FR)

(72) Inventors: Nadira Delhem, Marcq en Baroeul (FR); Pierre Busson, Antony (FR); Olivier Morales, Lille (FR); Clement Barjon, Villejuif (FR); Dhafer Mrizak, Lille (FR); Claire Lhuillier, Le Kremlin-Bicetre (FR); Rami Mustapha, Lille (FR)

(73) Assignees: Universite de Lille, Lille (FR); Centre National de la Recherche Scientifique, Paris (FR); Institut Gustave Roussy, Villejuif (FR); Cellvax, Romainville (FR); Universite Paris-Saclay, Saint Aubin (FR)

( * ) Notice: Subject to any disclaimer, the term of this patent is extended or adjusted under 35 U.S.C. 154(b) by 0 days.

(21) Appl. No.: 15/316,074

(22) PCT Filed: Jun. 5, 2015

(86) PCT No.: PCT/FR2015/051498
§ 371 (c)(1),
(2) Date: Dec. 2, 2016

(87) PCT Pub. No.: WO2015/185875
PCT Pub. Date: Dec. 10, 2015

(65) Prior Publication Data
US 2017/0283499 A1 Oct. 5, 2017

(30) Foreign Application Priority Data

Jun. 6, 2014 (FR) ...................... 14 55177

(51) Int. Cl.
A61K 39/385 (2006.01)
A61K 39/00 (2006.01)
C07K 16/28 (2006.01)
C07K 16/30 (2006.01)
C07K 16/18 (2006.01)
A61K 39/395 (2006.01)
A61K 45/06 (2006.01)

(52) U.S. Cl.
CPC ...... *C07K 16/2851* (2013.01); *A61K 39/3955* (2013.01); *A61K 45/06* (2013.01); *C07K 16/18* (2013.01); *C07K 16/30* (2013.01); *C07K 16/3092* (2013.01); *A61K 2039/505* (2013.01); *C07K 2317/34* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| 8,329,660 | B2  |   | 12/2012 | Kuchroo et al. |                       |
|-----------|-----|---|---------|----------------|-----------------------|
| 9,346,876 | B2  | * | 5/2016  | Kuchroo        | ............ C07K 14/4713 |
| 2014/0234320 | A1 | * | 8/2014 | Croft        | ................. C07K 16/2878 |
|           |     |   |         |                | 424/139.1             |

FOREIGN PATENT DOCUMENTS

| WO | 2010/084999 A1 | 7/2010  |
| WO | 2012/177788 A1 | 12/2012 |

OTHER PUBLICATIONS

Klibi et al. Blood diffusion and Th1-suppressive effects of galectin-9—containing exosomes released by Epstein-Barr virus-infected nasopharyngeal carcinoma cells. (Blood. 2009;113:1957-1966 (Year: 2009).*
Mengshol et al. A Crucial Role for Kupffer Cell-Derived Galectin-9 in Regulation of T Cell Immunity in Hepatitis C Infectio. PLoS ONE, 2010, 5(3): e9504. (Year: 2010).*
Shimmura-Tomita et al. Galectin-9-Mediated Protection from Allo-Specific T Cells as a Mechanism of Immune Privilege of mmune Privilege of Corneal Allografts. PLoS ONE 8(5): e63620, 2013 (Year: 2013).*
Wang et al. Tim-3-Galectin-9 pathway involves the suppression induced by CD4+CD25+ regulatory T cells. Immunobiology 214 (2009) 342-349. (Year: 2009).*
Brown et al. Tolerance of single, but not multiple, amino acid replacements in antibody VH CDR 2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
Editorial policies for BMC journal. https://www.biomedcentral.com/getpublished/editorial-policies. pp. 1-19, Oct. 18, 2018 (Year: 2018).*
The International Search Report and Written Opinion, dated Mar. 22, 2016, in the corresponding PCT Appl. No. PCT/FR2015/051498.

(Continued)

*Primary Examiner* — Maher M Haddad
(74) *Attorney, Agent, or Firm* — Morgan, Lewis & Bockius LLP

(57) ABSTRACT

The invention relates to an antibody which is directed against galectin-9 and is an inhibitor of the suppressor activity of regulatory T lymphocytes, and also to the use of this antibody for the treatment of diseases associated with the suppressor activity of regulatory T lymphocytes, in particular the treatment of cancer.

7 Claims, 26 Drawing Sheets
Specification includes a Sequence Listing.

(56) References Cited

OTHER PUBLICATIONS

Barjon et al., "A novel monoclonal antibody for detection of galectin-9 in tissue sections: application to human tissues infected by oncogenic viruses," Infectious Agents and Cancer, Jul. 17, 2012, 7:16.

Takeshi et al, "Galectin-9 signaling prolongs survival in murine lung-cancer by inducing macrophages to differentiate into plasmacytoid dendritic cell-like macrophages", Clinical Immunology, vol. 142, No. 3, 2012, pp. 296-307.

The English translation of the Japanese Office Action, dated Jan. 28, 2019, in the related Japanese Appl. No. 2017-516216.

Transmittal of third party observations to applicant, dated Jan. 21, 2019, in the related EP Appl. No. 15732846.9.

Transmittal of third party observations to applicant, dated Dec. 13, 2018, in the related EP Appl. No. 15732846.9.

Jones et al., "Tim-3 expression defi nes a novel population of dysfunctional T cells with highly elevated frequencies in progressive HIV-1 infection," J. Exp. Med., 2008, 205, 2763-2779.

Adhikary et al. "Control of Epstein-Barr virus infection in vitro by T helper cells specific for virion glycoproteins," J Exp Med 203 : 995-1006, 2006.

Schneidt et al., "Antibodies conjugated with viral antigens elicit a cytotoxic T cell response against primary CU ex vivo," Leukemia 33: 88-98, 2019.

Yip et al., "Increase in tumour-infiltrating lymphocytes with regulatory T cell immunophenotypes and reduced z-chain expression in nasopharyngeal carcinoma patients," Clinical and Experimental Immunology, 155: 412-422, 2009.

Barjon et al., "A novel monoclonal antibody for detection of galectin-9 in tissue sections: application to human tissues infected by oncogenic viruses," Infect Agent Cancer. 2012; 7: 16.

Ngjow et al., "Anti-TIM3 Antibody Promotes T Cell Ifn-γ-Mediated Antitumor Immunity and Suppresses Established Tumors," Cancer Res. May 15, 2011;71(10):3540-51.

Shin et al., "The evolution of checkpoint blockade as a cancer therapy: what's here, what's next?" Curr Opin Immunol. Apr. 2015;33:23-35.

Seki et al., "Galectin-9 suppresses the generation of Th17, promotes the induction of regulatory T cells, and regulates experimental autoimmune arthritis," Clin Immunol. Apr. 2008;127(1):78-88.

Lhuillier et al., "Characterization of neutralizing antibodies reacting with the 213-224 amino-acid segment of human galectin-9," PLoS ONE 13(9): e0202512.

Barjon, "Biochemical and Functional Characterization of New Anti-Galectin-9 Monoclonal Antibodies for Diagnostic and Therapeutic Applications," Doctoral Thesis, Paris-Sud University, Doctoral School of Cancerology (2013).

\* cited by examiner

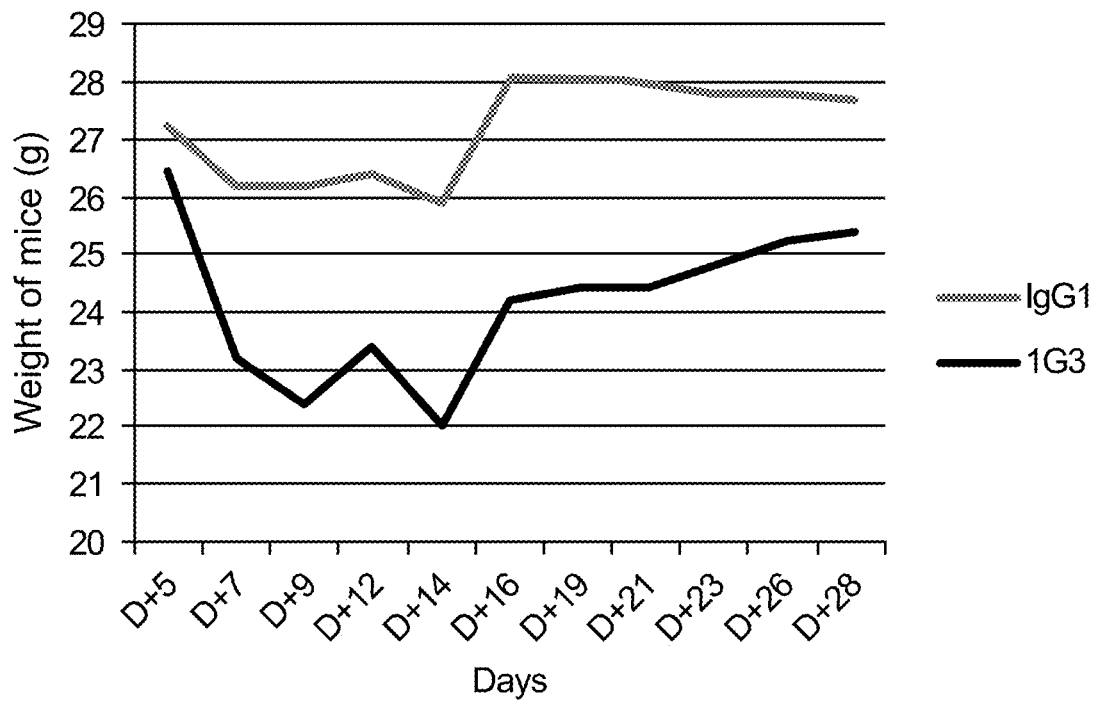
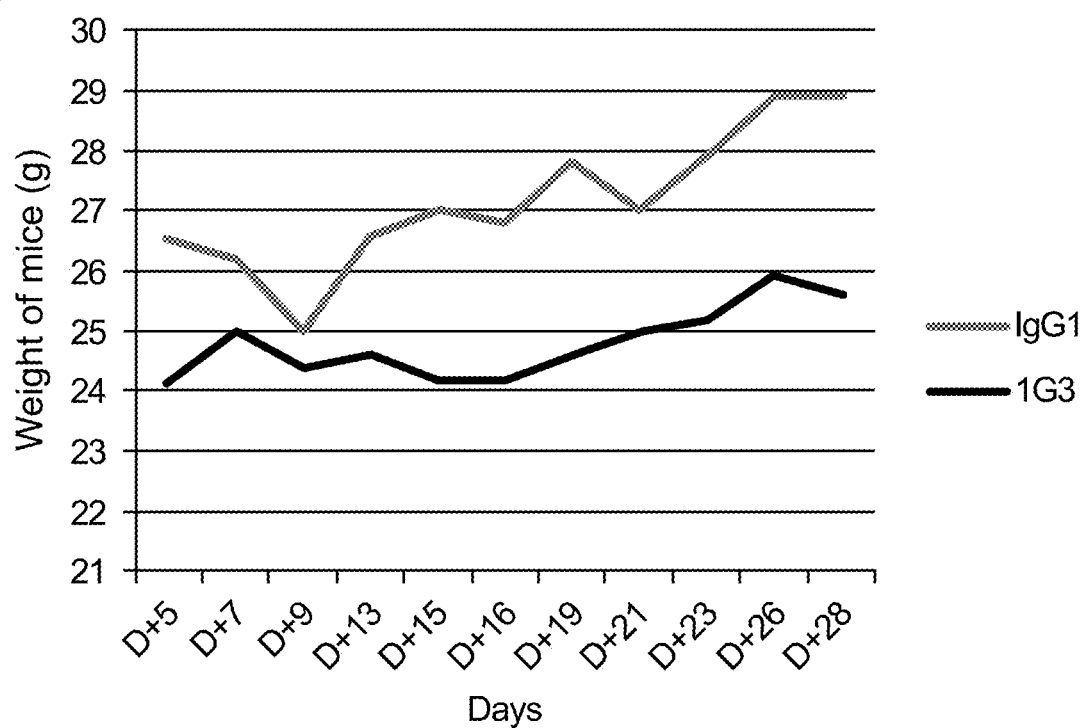
FIG. 18

Figure 19:
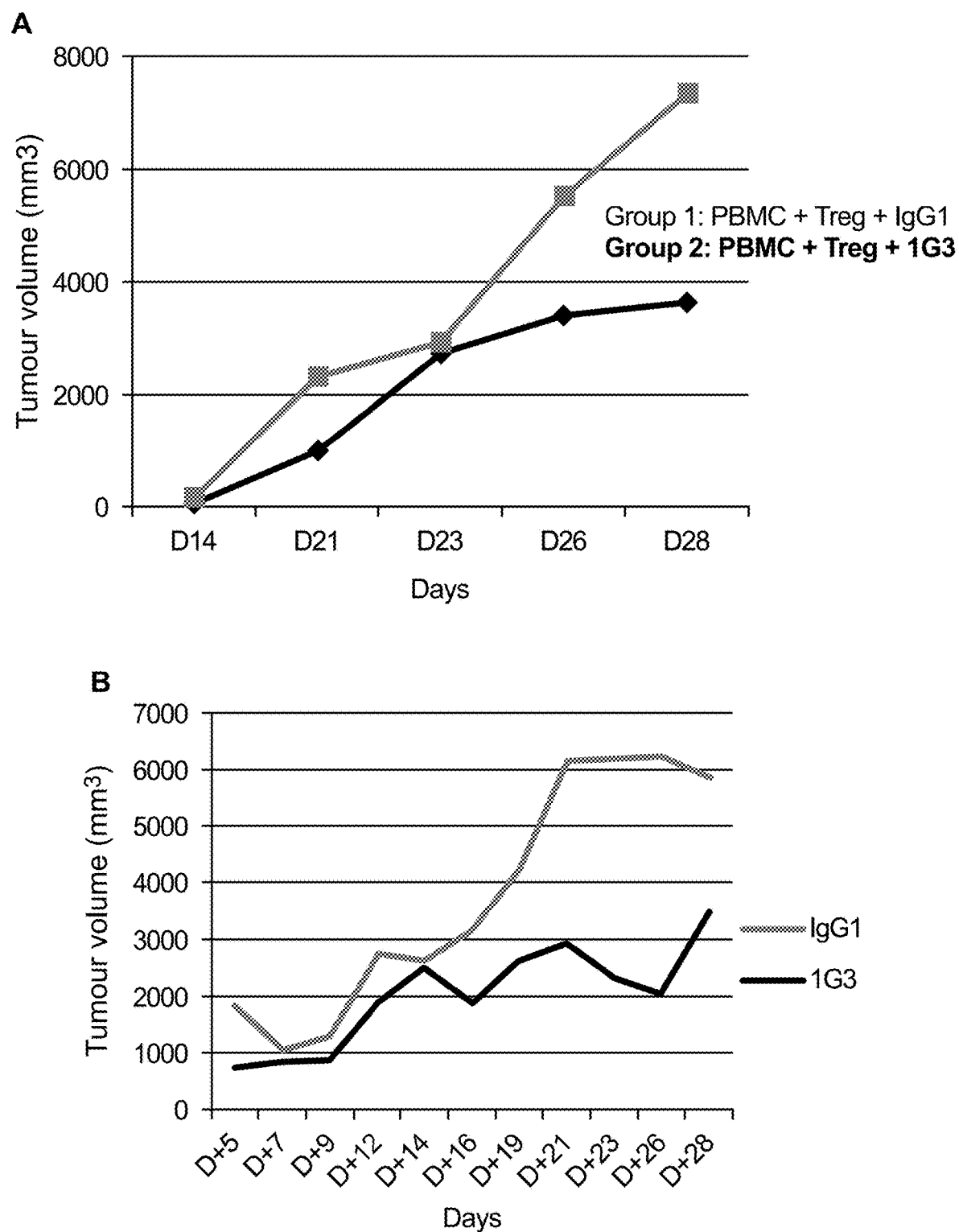

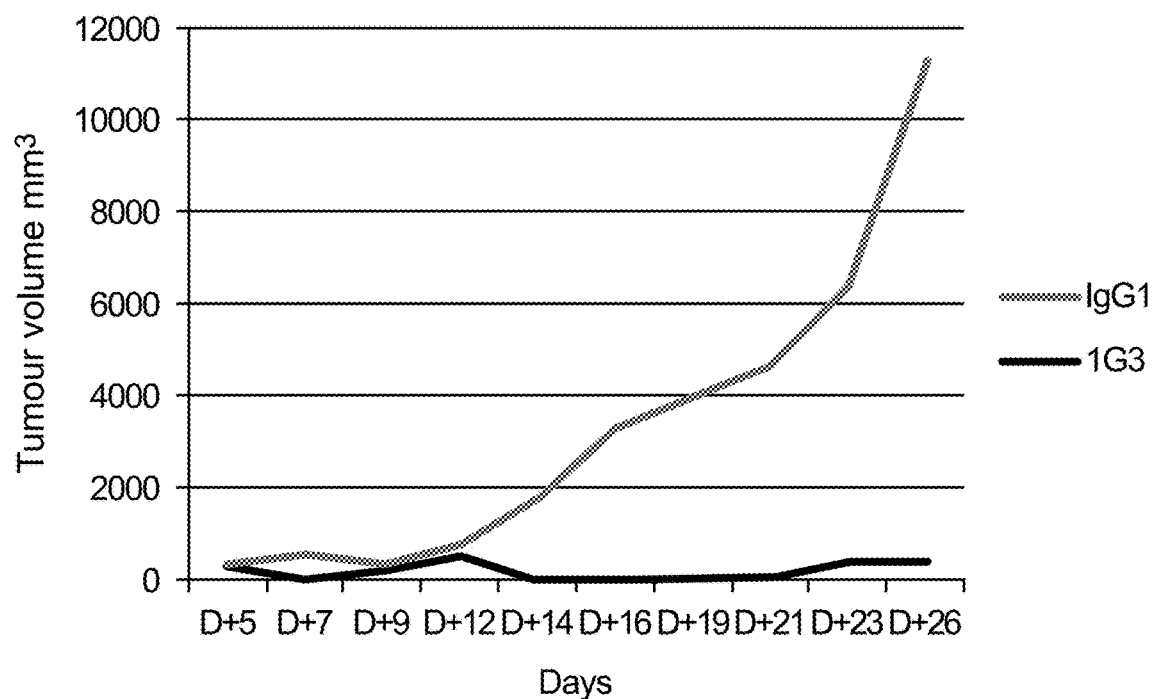
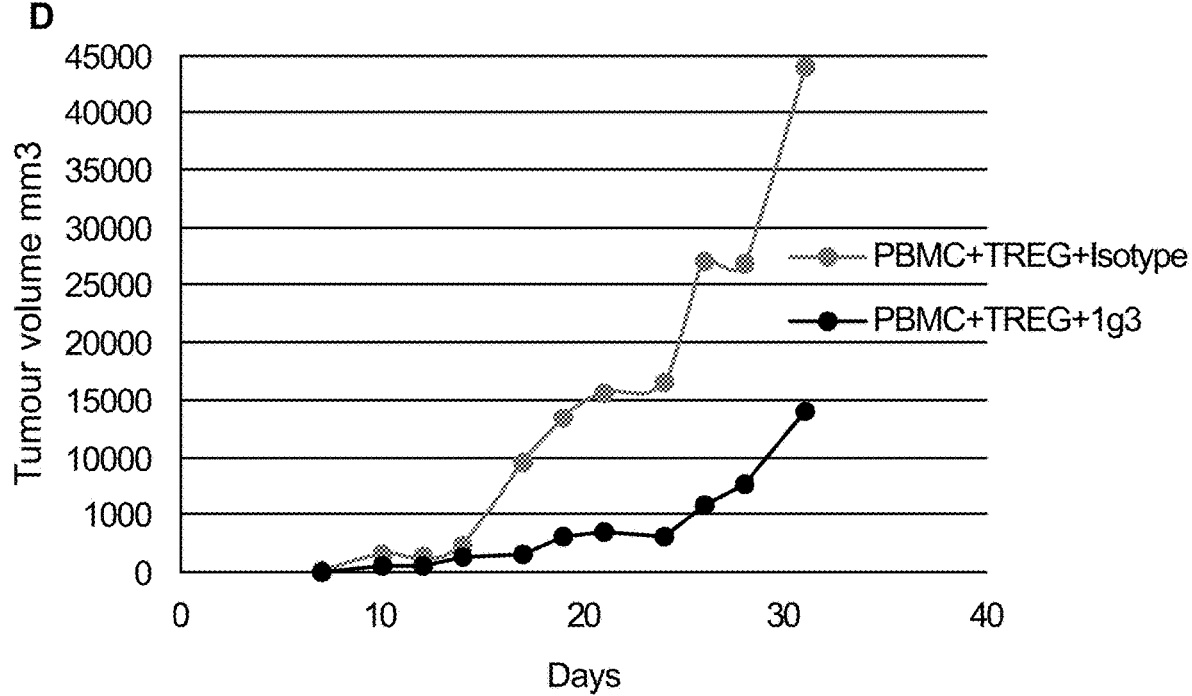
FIG. 19

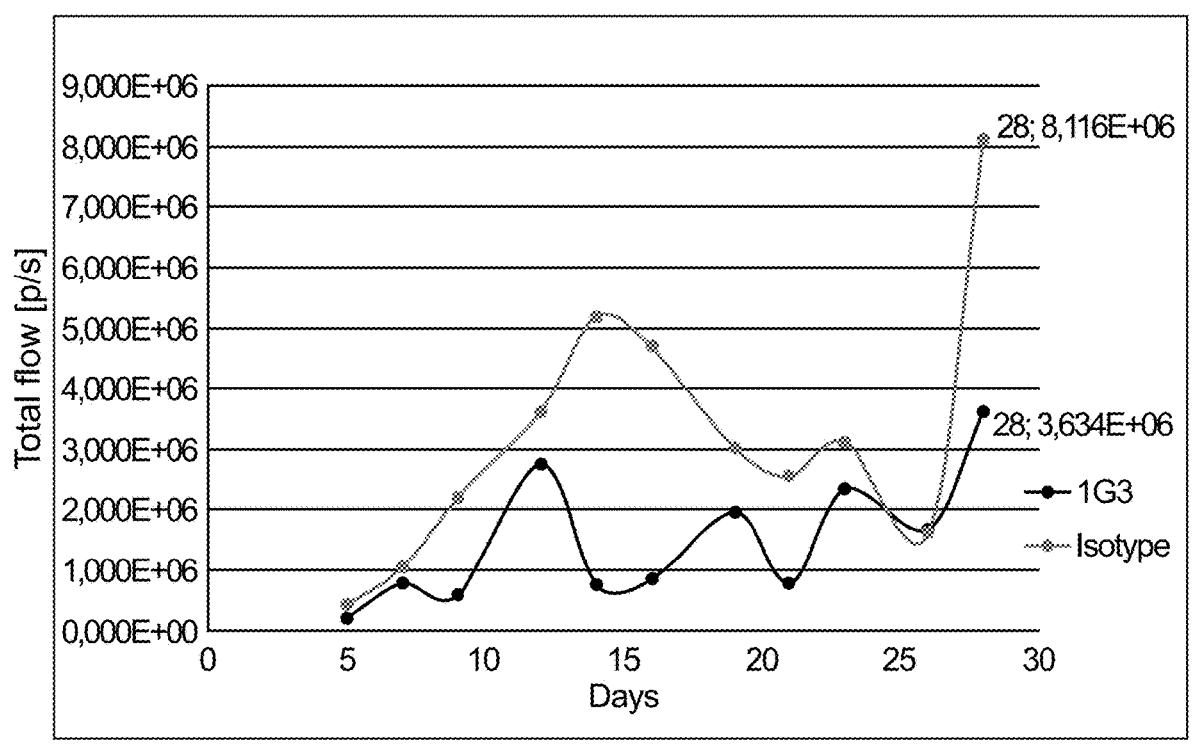
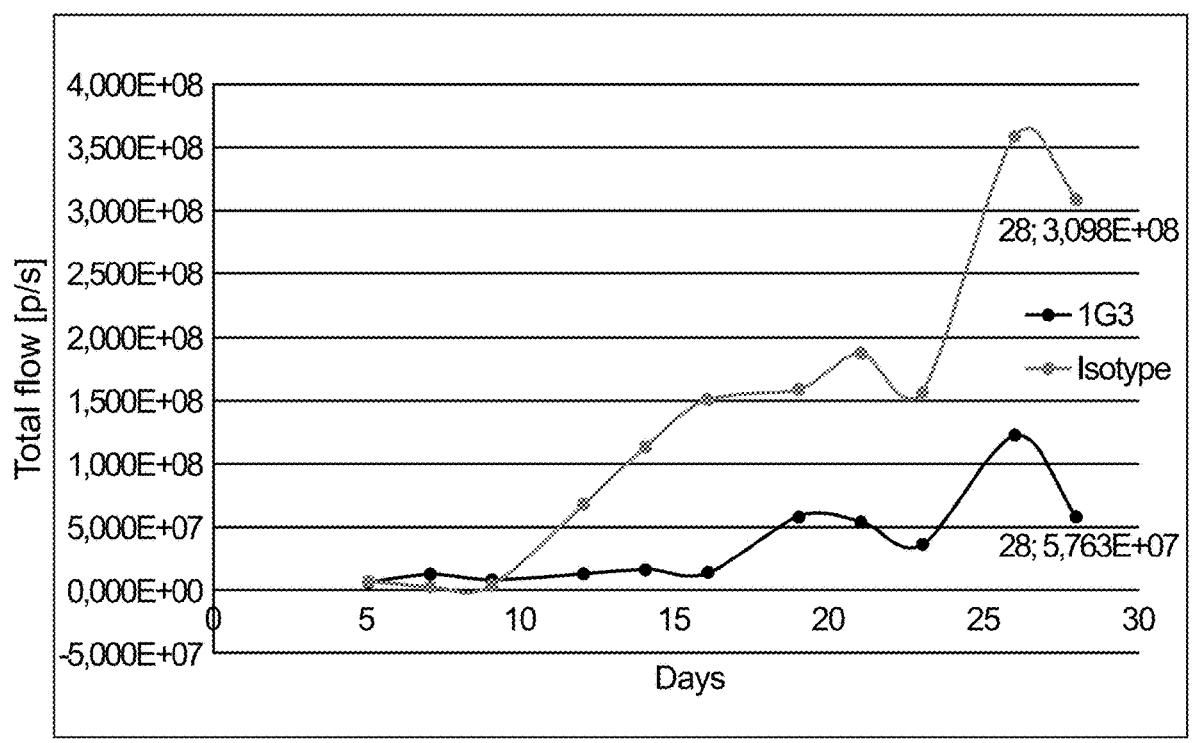
FIG. 21

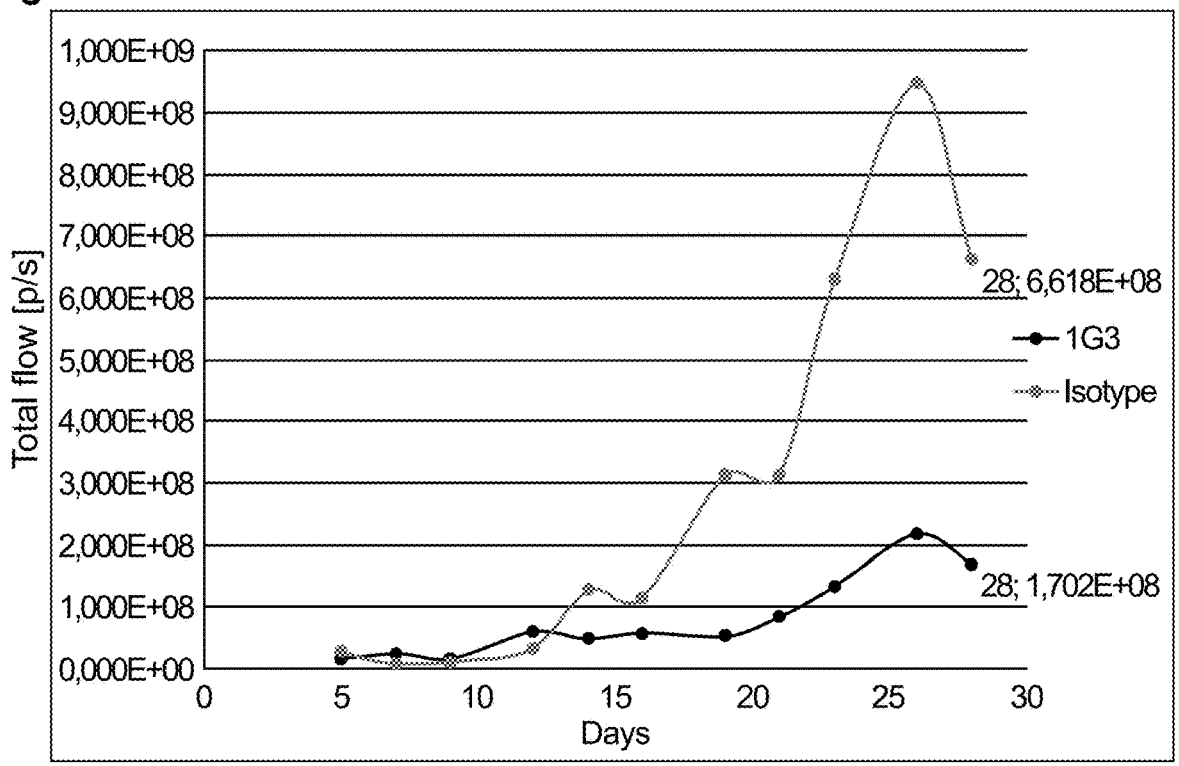
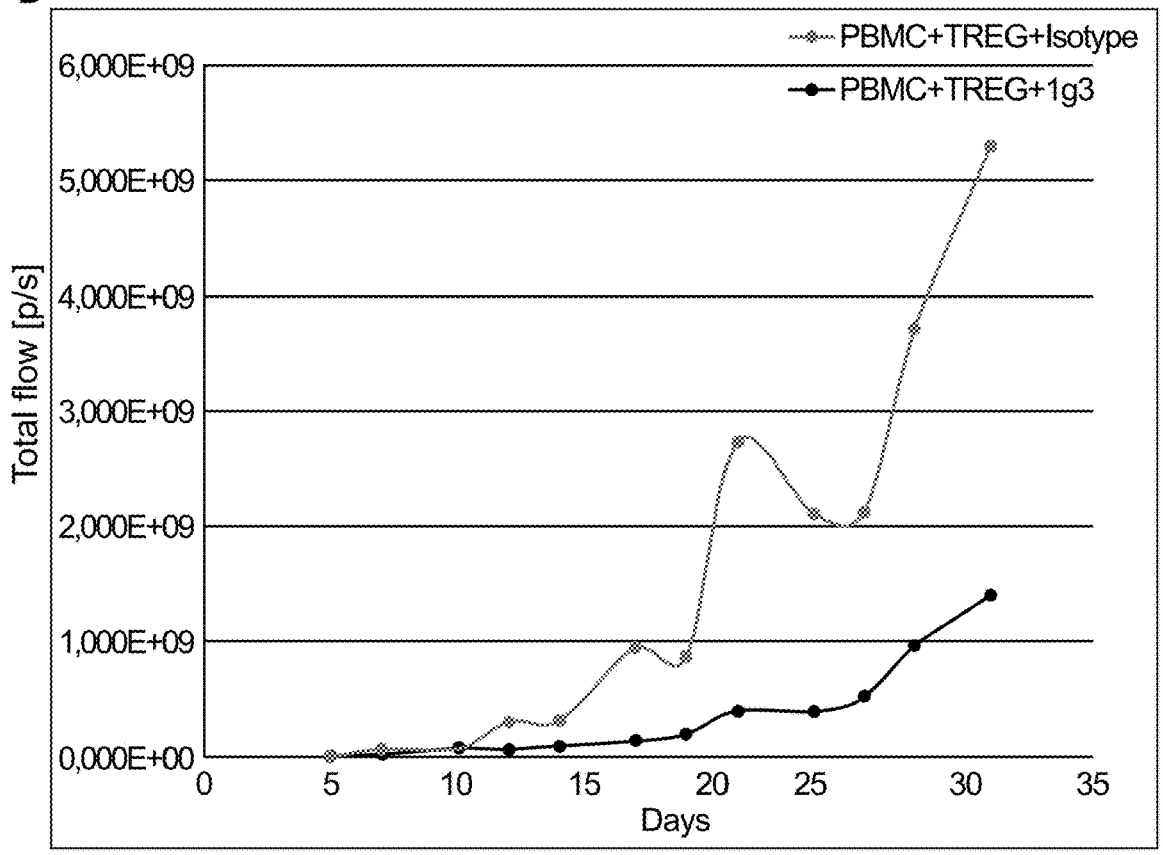
FIG. 21

ANTIBODY WHICH IS DIRECTED AGAINST GALECTIN-9 AND IS AN INHIBITOR OF THE SUPPRESSOR ACTIVITY OF REGULATORY T LYMPHOCYTES

This application is a National Stage Application of PCT/FR2015/051498 filed Jun. 5, 2015, which claims priority from French Patent Application No. 14 55177 filed Jun. 6, 2014. Each of the prior mentioned applications is hereby incorporated by reference herein in its entirety.

SEQUENCE LISTING

The instant application contains a Sequence Listing which has been filed electronically in ASCII format and is hereby incorporated by reference in its entirety. Said ASCII copy, created on May 31, 2017, is named 114353-94291_SL.txt and is **** bytes in size.

The invention relates to an antibody directed against galectin-9 and is an inhibitor of the suppressor activity of regulatory T lymphocytes, as well as to the use of this antibody for the treatment of illnesses associated with the suppressor activity of regulatory T lymphocytes.

Human T lymphocytes are characterised by the expression of a membrane marker called CD3 and a specific receptor, the TCR (T cell receptor), which is directly involved in the specific recognition of an antigen. This antigen recognition by the naïve T lymphocyte causes the activation of the primary immune response resulting in a modification of the phenotype and of the activity of the T lymphocytes.

Various types of T lymphocyte populations will develop, for example "effector" cells or effector T lymphocytes, which will fulfil specialised functions for defending the organism. Thus the CD4+ T lymphocytes, also referred to as auxiliary T lymphocytes, secrete major cytokines assisting in particular the B lymphocytes in their humoral function (the production of specific antibodies) and the CD8+ T lymphocytes in their cytotoxic activity.

Another population of CD4+ T lymphocytes consists of natural regulatory T lymphocytes, hereinafter referred to more briefly as "regulatory T lymphocytes". They constitutively overexpress the CD25 molecule (the regulator T lymphocytes may also be called "CD4+CD25+") and the Foxp3 transcription factor. This small percentage of CD4+ CD25+ T lymphocytes has the particularity of negatively regulating the actors of the immune response that would have recognised various auto-antigens by their TCRs. Regulator T lymphocytes also fulfil a major role in the physiology of the immune system in particular for protecting the organism against the emergence of autoimmune illnesses.

However, it has been proposed that, in a pathological situation, regulatory T lymphocytes may cause an inappropriate immune suppression, which then assists tumoral growth or the persistence of infectious pathogens (viruses, bacteria, parasites, etc.). Numerous studies have shown that regulatory T lymphocytes reduce anti-tumoral or anti-viral immune responses, in particular by inappropriately inhibiting the activity of the effector T lymphocytes, thus assisting the persistence of viruses and tumoral progression in a great majority of cancers.

The mechanisms by which the regulatory T lymphocytes exert their suppressor effects on the effector T lymphocytes are still poorly known. However, various studies have shown various mechanisms by means of which the regulatory T lymphocytes could suppress the immune response. Among the possible explanations, studies have for example shown that Foxp3+ regulator lymphocytes may lyse the effector T lymphocytes by the production of granzymes/perforins (1) or by depriving the effector T lymphocytes of IL-2 or by inhibiting the proliferation of effector T lymphocytes, in particular by expressing surface molecules such as Galectin-1, which interacts with receptors expressed on the effector T lymphocytes and causes the stoppage of the cell cycle of the effector T lymphocytes (2).

The physiopathological role of Tregs in cancers has thus encouraged the immergence of a new anti-tumoral therapeutic strategy. It consists of neutralising the factors inhibiting the immune response, in particular the regulatory T lymphocytes, or in other words breaking the tolerance vis-à-vis tumoral antigens.

This is because, for the purpose of reversing the balance between regulatory T lymphocytes and effector T lymphocytes in the control of anti-tumoral immunity, many teams have sought to develop therapeutic strategies aimed at inhibiting the CD4+CD25+ regulator T lymphocytes, in particular by targeting, with monoclonal antibodies, surface molecules expressed by these regulatory T lymphocytes, and in particular those acting in the suppressor activity of these regulatory T lymphocytes.

Analyses carried out in rodents have for example shown that the inhibition of the CD4+CD25+ regulatory T lymphocytes by a monoclonal antibody directed against the alpha receptor of IL-2 (CD25) promoted the activation and expansion of effector T cells, thus inhibiting tumoral growth (3). However, CD25 is also expressed by the effector T cells activated. Thus this strategy has to be adopted with care since it may also promote the elimination of effector T lymphocytes.

It has also been documented that activation of the signalling by GITR via an anti-GITR antibody was capable of inhibiting the suppressor activity of the regulatory T lymphocytes (4). In this context, the use of an anti-GITR antibody in the treatment of murine tumours made it possible to increase the anti-tumoral response of the CD4+ and CD8+ T lymphocytes, and this more effectively when the tumour is already installed. However, activated effector T lymphocytes also express GITR. Consequently there also exists a risk of suppression of effector T lymphocytes during the use of an anti-GITR antibody.

The strategy aimed at inhibiting regulatory T lymphocytes has also been envisaged by the use of an anti-CTLA4 antibody, a marker expressed by regulator T lymphocytes. Thus, in a mouse model having a KO (KnockOut) of CTLA-4 in regulatory T lymphocytes, or during the use of anti-CTLA-4 antibodies, an increase in the activity of the effector T lymphocytes and the reduction in the suppression mediated by the regulator T lymphocytes was shown, leading to an inhibition of tumoral growth (5). However, activated effector T lymphocytes also express the CRLA-4 marker. Consequently there also there exists a risk of suppression of the effector T lymphocytes by the use of an anti-GITR antibody.

Thus, despite the promising effect of these various molecules, one of the obstacles to the specific depletion of regulatory T lymphocytes is the lack of specificity of their surface markers. This is because the surface proteins CD25, CTLA-4 or GITR, expressed by the regulatory T lymphocytes, are also markers of activation of the effector T lymphocytes. The use of these proteins as targets for the depletion of regulatory T lymphocytes thus has the undesirable effect of the elimination of many CD4+ and CD8+ effector T lymphocytes, essential to tumoral regression. In this context, it remains very difficult to specifically target regulatory T lymphocytes in therapeutic protocols.

Consequently there still exists a need for compounds for selectively and effectively inhibiting the suppressor activity of regulatory T lymphocytes.

One of the aims of the invention is thus to provide an antibody that is directed against a specific marker of regulatory T lymphocytes and affords inhibition of the suppressor activity of regulatory T lymphocytes, without altering the function of the effector T lymphocytes.

The inventors have shown the merit of having shown that a molecule, Galectin-9, is expressed specifically by regulatory T lymphocytes during activation and that an antibody directed against this molecule makes it possible to inhibit the suppressor activity of the regulatory T lymphocytes, and this in a specific manner, that is to say without inhibiting effector T lymphocytes. Moreover, it has also been demonstrated that such an antibody is capable of neutralising the conversion of the conventional CD4+ T lymphocytes into immunosuppressor CD4+ T lymphocytes induced by Galectin-9, thus promoting the maintenance of anti-tumoral immune response in the patient being cared for according to the invention.

It has just been discovered that such an antibody directed against Galectin-9 and inhibiting the suppressor activity of regulatory T lymphocytes could be used in the treatment of illnesses associated with the suppressor activity of regulatory T lymphocytes.

Here "illness associated with the suppressor activity of regulatory T lymphocytes" means any illness (not autoimmune) in which the suppressor activity of regulatory T lymphocytes plays a role, in particular by promoting the development or persistence of the illness. In particular, it has been demonstrated that the suppressor activity of regulatory T lymphocytes promotes the development of tumours. The invention therefore aims more particularly at cancers in which the suppressor activity of T lymphocytes plays a role.

Galectin-9, which may be referred to more concisely as "Gal9", forms part of the family of galectins. Galectins, or type-S lectins, constitute a family composed of fifteen members in vertebrates, including ten in humans. Galectin-9 interacts preferentially with beta-galactoside residues of glycoproteins and glycolipids. In humans, Galectin-9 exists in three isoforms, long, medium and short.

Several studies have been carried out in order to determine the link existing between the development of cancers and galectins, in particular Galectin-9. However, it is considered the majority of these studies that Galectin-9 has a cytotoxic activity against activated T lymphocytes (whether CD4+ or CD8+) and does not have any cytotoxic activity against non-activated T lymphocytes.

For example, the patent application EP 1586325 starts from the postulate that, "in vitro", Galectin-9 induces apoptosis of tumoral cells, in particular in malignant or metastatic cells, but not normal cells. The application EP 1586325 thus relates to a drug comprising Galectin-9 or molecules causing the production and/or release of Galectin-9, etc.

The objective was therefore to use Galectin-9 or factors making it possible to increase Galectin-9, while the present invention on the contrary tends to inhibit it.

The subject matter of the present invention is thus an antibody directed against Galectin-9 and inhibiting the suppressor activity of regulatory T lymphocytes.

In other words, the invention relates to an antibody directed against Galectin-9, characterised in that it is an inhibitor of the suppressor activity of regulatory T lymphocytes.

This is because the invention is based on the unexpected findings made by the inventors who observed (i) on the one hand that Galectin-9 is directly expressed by regulatory T lymphocytes and that its expression is increased during their activation, and (ii) secondly that Galectin-9 is very weakly expressed by effector T lymphocytes and that this expression disappears during activation. Moreover, the inventors observed that the inhibition of Galectin-9 by an antibody allows inhibition of the suppressor activity of regulatory T lymphocytes.

"Regulatory T lymphocytes" means the subpopulation of natural regulatory T lymphocytes, also referred to as Treg, characterised by an expression constituting CD25, CTLA-4 and GITR and by a specific expression of the transcription factor Foxp3. The regulatory T lymphocytes more particularly referred to by the present invention are therefore natural regulatory T lymphocytes, or nTreg.

"Suppressor activity of the regulatory T lymphocytes" means the immunosuppressor activity that regulatory T lymphocytes exert on effector T lymphocytes, once activated, in a pathological situation, and which in particular promotes tumoral growth. Preferably, the suppressor activity of regulatory T lymphocytes can be understood as the activity reducing the anti-tumoral immune responses by inhibition of the activity of the effector T lymphocytes. The suppressor activity of the regulatory T lymphocytes can be analysed in accordance with various techniques known to persons skilled in the art, for example, an MLR (mixed leukocyte reaction) method can be implemented, which uses a co-culture of Treg lymphocytes and autologous or heterologous immune cells (total PBMCs or T CD4+). This can be done by proliferation tests based on (i) the incorporation of radioelements such as tritiated thymidine or (ii) the incorporation EdU (5-ethynyl-2'-deoxyuridine), which is incorporated during the synthesis of DNA and which follows an enzyme reaction will make possible the emission of a fluorescence (Click-it EdU Proliferation test) or (iii) flow cytometry (CSFE).

The inhibitor effect of an antibody according to the invention can thus for example be analysed by such an MLR method, carried out in the presence of the antibody being tested.

Reference can be made here to the "examples" and "equipment and methods" parts for more details concerning the use of such an analysis method.

The terms "antibodies" and "immunoglobulin" are used indifferently and refer to immunoglobulin molecules or immunologically active portions of immunoglobulin molecules, i.e. molecules comprising the specific fixing sites of a given antigen. The term antibody covers not only entire antibody molecules but also the fragments of antibodies and variants (including derivatives such as humanised antibodies) of antibodies and fragments of antibodies.

Immunoglobulins are well known to persons skilled in the art and consist of two heavy chains connected to each other by disulphide bridges, each heavy chain being connected to a light chain by a disulphide bridge. There exist two kinds of light chain, lambda (λ) and kappa (K) chains. There exist five main classes of heavy chain that determine the functional activity of the antibody: IgM, IgD, IgG, IgA and IgE.

Each chain contains distinct sequence domains. The light chain comprises two domains, a variable domain (or region) (VL) and a constant domain (CR). The heavy chain comprises four or five domains according to the class of antibody, one variable domain (VH) and three or even four constant domains (CH1, CH2, CH3 and optionally CH4).

The variable regions of the light (VL) and heavy (VH) chains determine the specificity for the antigen and the fixing site on this antigen.

The constant domains of the light (CL) and heavy (CH) chains confer important biological properties on the antibody, such as the association of the antibody chains with each other, mobility through the placenta, fixing of the complement and/or fixing to the Fc receptors (FcR). The Fv fragment corresponds to the V-terminal part of the Fab fragment, described below, of the immunoglobulin, and comprises the variable portions of a light chain and of a heavy chain (VL and VH). The specificity of the antibody lies in the structural complementarity between the recognition site of the antibody and the antigen determinant. The recognition site of the antibody consists essentially of residues coming from hypervariable regions or ones determining complementarity ("complementary determining regions" or CDRs). Occasionally the residues coming from non-hypervariable regions or framework regions (FR) influence the general structure of the domain and therefore the recognition sites. The term "complementarity regions" (CDR) relates to amino acid sequences which, together, define the affinity of the fixing and specificity of the natural Fv region of the fixing site of a native immunoglobulin. Each of the light chains and each of the heavy chains of an immunoglobulin have three regions CDRs designated by L-CDR1, L-CDR2, L-CDR3 and H-CDR1, H-CDR2, H-CDR3 respectively. A binding site of an antigen consequently comprises six CDRs. The framework regions (FRs) relate to the sequences of amino acids interposed between the CDRs, that is to say portions of the variable regions of the light and heavy chains of the immunoglobulins that are relatively preserved between various immunoglobulins of the same species.

An antibody according to the invention may be a monoclonal or polyclonal antibody. Preferably, an antibody according to the invention is a monoclonal antibody.

The term "monoclonal antibody" or "mAb" designates an antibody with a unique amino acid composition, which is directed against a specific antigen and can be produced by a single B cell clone or hybridome. Monoclonal antibodies may also be recombinant, that is to say be produced by protein engineering techniques.

The term "Fab" designates an antibody fragment with a molecular mass of approximately 50,000 daltons and has an activity of binding to the antigen. It comprises approximately half of the n-terminal side of the heavy chain and the whole of the light chain connected by a disulphide bridge. The Fab can be obtained in particular by treatment of immunoglobulin by a protease, papain.

The term "F(ab')2" designates a fragment of approximately 100,000 daltons and an activity of binding to the antigen. This fragment is slightly larger than two Fab fragments connected via a disulphide bridge in the hinge region. These fragments are obtained by treating an immunoglobulin with a protease, pepsin. The Fab fragment can be obtained from the F(ab')2 fragment by cleaving of the disulphide bridge of the hinge region.

A single Fv chain "scFv" corresponds to a VH: VL polypeptide synthesised using the genes coding for the VL and VH domains and a sequence coding for a peptide intended to bind these domains. An scFv according to the invention includes the CDRs maintained in an appropriate conformation, for example using genetic recombination techniques.

The dimers of "scFv" correspond to two scFv molecules connected together by a peptide bond. This Fv chain is frequently the result of the expression of a fusion gene including the genes coding for VH and VL connected by a linker sequence coding a peptide. The human scFv fragment may include CDR regions that are maintained in an appropriate conformation, preferably by means of the use of genetic recombination techniques. The "dsFv" fragment is a VH-VL heterodimer stabilised by a disulphide bridge; it may be divalent (dsFV2). Fragments of divalent Sc(Fv)2 or multivalent antibodies may form spontaneously by the association of monovalent scFvs or be produced by connecting scFvs fragments by peptide binding sequences.

The Fc fragment is the support for the biological properties of the antibody, in particular its ability to be recognised by immunity effectors or to activate the complement. It consists of constant fragments of the heavy chains beyond the hinge region.

The term "diabodies" signifies small antibody fragments having two antigen fixing sites. These fragments comprise, in the same VH-VL polypeptide chain, a variable heavy chain domain VH connected to a variable light chain domain VL. Using a binding sequence that is too short to allow the matching of two domains of the same chain, the matching with two complementary domains of another chain necessarily occurs and thus two antigen fixing sites are created.

An antibody of the invention may thus be an immunoglobulin consisting of two heavy chains and two complete light chains, or may be a fragment of immunoglobulin according to the invention, for example F(ab')2, Fab, Fv, scFv or Fc. Preferably, such an antibody fragment is the Fab region of an immunoglobulin, in particular the Fv region of an IgG1 antibody.

The antibodies described in the invention are isolated and purified, and are different from natural antibodies. When it is a case of an antibody or a nucleotide sequence according to the invention, the terms "isolated" and "purified" indicate that the molecule is present in the major absence of other biological macromolecules of the same type.

The term "chimeric antibody" relates to an antibody in which the sequence of each light chain and/or each heavy chain that constitutes it comprises or consists of a hybrid sequence issuing from at least two distinct animals. Preferably, the chimeric antibodies of the invention are human/mouse hybrids. In particular, a chimeric antibody of the invention may comprise a VH domain and a VL domain of an antibody coming from a non-human animal, in particular murine, and a CH domain and a CL domain of a human antibody. Thus, preferentially, an antibody of the invention comprises a VH domain and a VL domain of an antibody derived from the 1G3 antibody defined below and a CH domain and a CL domain of a human antibody.

According to the invention, the term "humanised antibodies" relates to an antibody issuing from a non-human animal in which the sequences of the heavy chains and of the light chains other than the CDRs have been replaced by corresponding sequences of one or more antibodies of human origin. Preferentially, the term "humanised antibody" relates to an antibody where the sequences of the heavy chains and of the light chains are of human origin and the CDRs of which issue from the 1G3 antibody.

The antibodies according to the invention are preferably monoclonal antibodies, that is to say they recognise only one antigen determinant in Galectin-9, unlike polyclonal antibodies, which correspond to a mixture of monoclonal antibodies, which therefore recognise several antigen determinants in the same molecule.

Monoclonal antibodies according to the invention can be obtained according to techniques well known to persons skilled in the art. For example, it is possible to use the cell fusion technique, the technique of cloning sequences of heavy and light chains, the technique of phage or ribosome display, the immunisation of mice having the list of human immunoglobulins and expression in an ad hoc cell or a transgenic animal. These techniques are well known to persons skilled in the art.

The present invention relates to antibodies directed against Galectin-9 and inhibitors of the suppressor activity of regulatory T lymphocytes. In particular, the inventors have developed a hybridome producing a murine antibody IGg1, Kappa, 1G3, directed against Galectin-9 and inhibiting the suppressor activity of regulatory T lymphocytes. The inventors have characterised the variable domains of the light and heavy chains of this monoclonal antibody mAb 1G3 and have thus determined the CDRs of this antibody, presented in table 1.

TABLE 1

| Domains mAb 1G3 | Sequence |
|---|---|
| VH | MKCSWGIFFLLSVTAGVHSKVQLQQSGAELVKPGASVKLS CKASGYTFTDYTIHWVKQRSGQGLEWIGWFYPGSHSIKYN EQFKDRATLTADKSSSTVYMELSRLTSEDSAVYFCTRHGG YDGFDYWGQGTTLTVSSAKTTPPSVYPL (SEQ ID NO: 1) |
| H-CDR1 | GYTFTDYTIH (SEQ ID NO: 2) |
| H-CDR2 | WFYPGSHSIKYNEQFKDR (SEQ ID NO: 3) |
| H-CDR3 | HGGYDGFDY (SEQ ID NO: 4) |
| VL | LDGGKMDSQAQVLMLLLLWVSGTCGDIVMSQSPSSLAVSV GEKITMSCKSSQSLFYSTNQKNYLAWYQQKPGQSPKLLIY WASTRESGVPDRFTGSGSGTDFTLTISSVKAEDLAVYYCQ QYYYFPYTFGGGTKLEIKRADAAPTVSIFPPSS (SEQ ID NO: 5) |
| L-CDR1 | KSSQSLFYSTNQKNYLA (SEQ ID NO: 6) |
| L-CDR2 | WASTRES (SEQ ID NO: 7) |
| L-CDR3 | QQYYYFPYT (SEQ ID NO: 8) |

A particular embodiment of the invention therefore relates to an antibody directed against Galectin-9 and inhibiting the suppressor activity of regulatory T lymphocytes, having the same fixing zone as the 1G3 antibody having as CDRs the six CDRs defined by:
the amino acid sequence SEQ ID NO:2 in the region H-CDR1
the amino acid sequence SEQ ID NO:3 in the region H-CDR2
the amino acid sequence SEQ ID NO:4 in the region H-CDR3
the amino acid sequence SEQ ID NO:6 in the region L-CDR1
the amino acid sequence SEQ ID NO:7 in the region L-CDR2
the amino acid sequence SEQ ID NO:8 in the region L-CDR3

In particular, a subject matter of the invention concerns an antibody directed against Galectin-9 and inhibiting the suppressor activity of regulatory T lymphocytes having as CDRs the six CDRs defined by:
the amino acid sequence SEQ ID NO:2 in the region H-CDR1
the amino acid sequence SEQ ID NO:3 in the region H-CDR2
the amino acid sequence SEQ ID NO:4 in the region H-CDR3
the amino acid sequence SEQ ID NO:6 in the region L-CDR1
the amino acid sequence SEQ ID NO:7 in the region L-CDR2
the amino acid sequence SEQ ID NO:8 in the region L-CDR3

In a particular embodiment, the variable region of the heavy chain of said antibody has the amino acid sequence SEQ ID NO: 1 and the variable region of the light chain of said antibody has the amino acid sequence SEQ ID NO: 5.

An antibody according to the invention therefore binds specifically to Galectin-9 and is an inhibitor of the suppressor activity of regulatory T lymphocytes.

According to another particular embodiment of the invention, an antibody according to the invention can bind specifically to an epitope of Galectin-9. Advantageously, an antibody according to the invention is capable of binding specifically to membrane or intracellular Galectin-9.

More particularly still, an antibody according to the invention can bind to the epitope recognised by the 1G3 antibody defined above.

Thus, according to a particular embodiment of the invention, an antibody according to the invention can bind specifically to the epitope of an amino acid sequence SEQ ID NO: 9, presented in table 2. This epitope, consisting of the amino acid sequence SED ID NO: 9, corresponds to the P4 peptide and covers the end of the binding peptide and the start of the C-terminal part of Galectin-9. This sequence exists in the three isoforms of Galectin-9 (amino acids 166 to 178 of the S isoform, amino acids 178 to 190 of the M isoform, amino acids 210 to 222 of the L isoform). Such an antibody can therefore react with all the isoforms of Galectin-9.

TABLE 2

| Sequence of Galectin-9 (epitope) |
|---|
| TPAIPPMMYPHPA (SEQ ID NO: 9) |

According to another particular embodiment, the antibody according to the invention is a chimeric antibody, preferably a murine/human chimeric antibody. In particular, this murine/human chimeric antibody may comprise the variable domains of the 1G3 antibody as defined above.

According to another particular embodiment, the antibody according to the invention is a humanised antibody. In particular, the variable domain of this humanised antibody may comprise framework regions of the human acceptor, and optionally human constant domains, and the CDRs of the non-human donor, in particular the CDRs defined above.

The inventors have also developed a hybridome producing a murine antibody IGg1, Kappa, 2E12, directed against Galectin-9 and an inhibitor of the suppressor activity of regulatory T lymphocytes. The inventors have characterised the variable domains of light and heavy chains of this monoclonal antibody mAb 2E12 and thus determined the CDRs of this antibody, presented in table 3.

TABLE 3

| Domains mAb 2E12 | Sequence |
|---|---|
| VH | MGWSFILLSVTAGVHSKVQLQQSGAELVKPGASVKLSC KASGYTFTEYTIHWVKQRSGQGLEWIGWFYPGSGSMEY NEKFDKATLTADNSSSTVYMELSRLTSEDSAVYFCERH GGYDGFDYWGQGTTLTVSSAKTTPPSVYPLIFLEDLLQ YSQLPWKIDVLLLFSQDFQAVY* (SEQ ID NO: 10) |
| H-CDR1 | GYTFTEYTIH (SEQ ID NO: 11) |
| H-CDR2 | WFYPGSGSMEYNEKFD (SEQ ID NO: 12) |
| H-CDR3 | HGGYDGFDY (SEQ ID NO: 13) |
| VL | LDGGKMDSQAQVLMLLLLWVSGTCGDIVMSQSPSSLAV SVGEKVTMSCKSSQSLLYSNNQKNYLAWYQQKPGQSPK LLIYWASTRGSGVPDRFTGSGSGTDFTLTISSVKAEDL AIYYCQQYYSYPFTFGGGTKLEIKRADAAPTVSIFPPS S (SEQ ID NO: 14) |
| L-CDR1 | KSSQSLLYSNNQKNYLA (SEQ ID NO: 15) |
| L-CDR2 | WASTRGS (SEQ ID NO: 16) |
| L-CDR3 | QQYYSYPFT (SEQ ID NO: 17) |

A particular embodiment of the invention therefore relates to an antibody directed against Galectin-9 and inhibiting the suppressor activity of regulatory T lymphocytes, having the same fixing zone as the 2E12 antibody having as CDRs the six CDRs defined by:
the amino acid sequence SEQ ID NO:11 in the region H-CDR1
the amino acid sequence SEQ ID NO:12 in the region H-CDR2
the amino acid sequence SEQ ID NO:13 in the region H-CDR3
the amino acid sequence SEQ ID NO:15 in the region L-CDR1
the amino acid sequence SEQ ID NO:16 in the region L-CDR2
the amino acid sequence SEQ ID NO:17 in the region L-CDR3

In particular, a subject matter of the invention concerns an antibody directed against Galectin-9 and inhibiting the suppressor activity of regulatory T lymphocytes having as CDRs the six CDRs defined by:
the amino acid sequence SEQ ID NO:11 in the region H-CDR1
the amino acid sequence SEQ ID NO:12 in the region H-CDR2
the amino acid sequence SEQ ID NO:13 in the region H-CDR3
the amino acid sequence SEQ ID NO:15 in the region L-CDR1
the amino acid sequence SEQ ID NO:16 in the region L-CDR2
the amino acid sequence SEQ ID NO:17 in the region L-CDR3

In a particular embodiment, the variable region of the heavy chain of said antibody has the amino acid sequence SEQ ID NO: 10 and the variable region of the light chain of said antibody has the amino acid sequence SEQ ID NO: 14.

As mentioned previously, according to another particular embodiment of the invention, an antibody according to the invention combines specifically to an epitope of Galectin-9. Advantageously, an antibody according the invention is able to bind specifically to membrane or intracellular Galectin-9.

More particularly again, an antibody according to the invention can bind to the epitope recognised by the 2E12 antibody defined above.

According to another particular embodiment, the antibody according to the invention is a chimeric antibody, preferably a murine/human chimeric antibody. In particular, this murine/human chimeric antibody may comprise the variable domains of the 2E12 antibody as defined above.

According to another particular embodiment, the antibody according to the invention is a humanised antibody. In particular, the variable domain of this humanised antibody may comprise framework regions of the human acceptor, and optionally human constant domains, and the CDRs of the non-human donor, in particular the CDRs defined above.

Antibody Production Method

The antibodies of the invention can be produced by any technique known to persons skilled in the art, for example, but without being limited thereto, by any chemical, biological, genetic or enzymatic technique taken alone or in combination.

It is for example possible to use the technique described below concerning the manufacture of the hybridome producing the monoclonal antibody directed against Galectin-9, 1G3 or 2E12.

The specific binding of the antibodies, according to the invention, directed against Galectin-9 can be analysed according to any known method of the prior art. As immunoassays that can be used, it is for example possible to site the western blot techniques, radioimmunological tests, ELISA, sandwich immunoassays, immunoprecipitation tests, precipitin tests, gel diffusion precipitin tests, immunoradiometric tests, fluorescence immunoassays or complement fixing tests. Such tests are well known to persons skilled in the art.

The action inhibiting the suppressor activity of the regulatory T lymphocytes of an antibody according to the invention thus generated can be analysed according to various techniques known to persons skilled in the art. For example, a cell proliferation test can be carried out. It is thus possible to refer to the technique used below concerning the cell proliferation test carried out with the antibody directed against Galectin-9, 1G3 or 2E12.

When the amino acid sequence of the desired sequence is known, a person skilled in the art can easily reproduce the antibody by standard polypeptide production techniques.

For example, such antibodies can be synthesised by a well-known solid-phase method, preferably using a commercially available peptide synthesis device in accordance with the recommendations of the supplier.

Alternatively, the antibodies of the invention can be obtained by techniques, well known to persons skilled in the art, of recombinant DNA in a suitable expression system. The term "expression system" means a cell host and a compatible vector under suitable conditions, that is to say conditions allowing expression of the protein coded by the foreign DNA carried by the vector and introduced into the host cell. Typically, the nucleic acid sequence coding an antibody can be inserted in a suitable expression vector, which will then be introduced into a suitable prokaryotic or eukaryotic host that will produce the desired antibody.

The terms "vector", "cloning vector" and "expression vector" relate to vehicles by means of which the DNA or RNA sequences coding the antibody can be introduced into a host cell so as to transform it and to allow the expression (that is to say transcription and translation) of the sequence introduced. An expression vector is typically a plasmid, a cosmid, an episome, an artificial chromosome, a phage or a viral vector.

Viral vectors include adenoviruses, retroviruses, the herpes virus and the vectors derived from the adeno-associated virus (AAV). Such recombinant viruses can be produced by well-known techniques, such as the transfection of cell lines enabling them to be encapsidated or by transient transfection with plasmid or complementation viruses expressing the necessary missing functions. Cell lines allowing encapsidation are for example PA317, PsiCRIP, GPenv+, 293, etc. The detailed protocols for producing such defective recombinant viruses for replication are available in the patent applications WO 95/14785, WO 96/22378, U.S. Pat. No. 5,882,877, etc.

The host cells are therefore transfected, infected or transformed by a nucleic acid or a suitable vector as described above.

The term "transformation" relates here to the introduction of a foreign (extrinsic or extracellular) gene or a DNA or RNA sequence into a host cell so that this host cell expresses the gene or sequence introduced in order to produce the desired substance, typically a protein coded by the gene or the sequence introduced.

Such usual expression systems include, without limitation, host cells and plasmid vectors of *E. coli*, insect host cells, and vectors of the baculovirus type and cells and vectors of mammals.

A method of production from a host cell expressing an antibody according to the invention may comprise the steps consisting of: (i) introducing in vitro or ex vivo a recombinant nucleic acid or a vector as described above into the competent host cell, (ii) cultivating in vitro or ex vivo the recombinant host cell thus obtained, (iii) optionally selecting the cells that express and/or secrete said antibody or polypeptide. Such host cells can be used for producing antibodies according to the invention.

According to a particular embodiment, a method for producing an antibody according to the invention may comprises the steps consisting of: (i) cultivating the transformed cell described above under conditions appropriate to the expression of the antibody; and (ii) recovering the antibody thus expressed.

The antibodies may be separated from the culture medium by conventional methods of purification of immunoglobulins such as, for example, purification on A-Sepharose protein, by hydroxyapatite chromatography, by gel electrophoresis, by dialysis or by affinity chromatography.

In a particular embodiment of the invention, a human chimeric antibody according to the invention can be produced by obtaining the nucleic sequences coding the VL and VH domains as mentioned previously, constructing a human chimeric antibody expression vector by the insertion of nucleic sequences in an expression vector for an animal cell having genes coding the CH and CL domains, and expressing the coded sequences by introducing the expression vector into the animal cell.

The CH domain of the human chimeric antibody may be of any region belonging to the human immunoglobulin. Preferably, it is a case of the class IgG, and preferably again IgG1. In the same way, the CL domain of the human chimeric antibody may be of any region belonging to the human immunoglobulin. Preferably it is a case of the Kappa class.

The chimeric or humanised antibodies according to the invention may in particular be obtained by genetic engineering of the antibodies.

A chimeric antibody may for example be constructed by a gene transfection technique or by a recombinant DNA technique.

A humanised antibody according to the invention may be produced by obtaining the CDR domains as mentioned previously, constructing a human antibody expression vector by the insertion of nucleic sequences into an expression vector for an animal cell having genes coding (i) a constant heavy chain region identical to that of a human antibody and (ii) a constant light chain region identical to that of a human antibody, and expressing the coded sequences by introducing the expression vector into the animal cell.

With regard to the humanised antibody expression vector, it may be a case of a type in which a gene coding a heavy antibody chain and a gene coding a light antibody chain exist in separate vectors, that is to say in which the genes exist in the same vector (tandem type). The tandem-type vectors are preferred with respect to the ease of construction of the expression vector, the ease of introduction into animal cells, etc. As an example of a humanised antibody expression vector of the tandem type, pKANTEX93 or pEE18 can be cited.

The humanised antibody production methods based on the gene or recombinant DNA techniques are well known in the prior art. The antibodies can be humanised according to various techniques known from the prior art, for example by CDR grafting, veneering or resurfacing, or by chain shuffling. The technique based on recombinant DNA for preparing such antibodies is also known.

An Fab fragment according to the invention may be obtained by treating an antibody, in particular an antibody directed against Galectin-9 and inhibiting the suppressor activity of regulatory T lymphocytes, by a protease, papain. This FAB fragment can also be produced by inserting a DNA coding the FAB fragment of the antibody in a vector that can be used in a prokaryotic or eukaryotic expression system and introducing this vector into the prokaryote or eukaryote appropriate for expressing the FAB fragment.

An F(ab')2 fragment according to the invention can be obtained by treating an antibody, in particular an antibody directed against Galectin-9 and inhibiting the suppressor activity of regulator T lymphocytes, by a protease, pepsin. The F(ab')2 fragment may also be obtained by joining together Fab' fragments as described above, by a thioether bond or a disulphide bridge.

An Fab' fragment according to the invention can be obtained by treating the F(ab')2 complex of an antibody, in particular an antibody directed against Galectin-9 and inhibiting the suppressor activity of regulatory T lymphocytes, by a reducing agent, dithiothreitol. The Fab' fragment can also be produced by inserting a DNA coding the Fab' fragment of the antibody in a vector that can be used in prokaryotic or eukaryotic expression system and introducing this vector into the prokaryote or eukaryote appropriate for expressing the Fab' fragment.

The ScFv fragment according to the invention can be produced by obtaining a sequence of cDNA coding the VH and VL domains previously described followed by the insertion of this DNA into a vector that can be used in a eukaryotic or prokaryotic expression system and introducing this vector in the eukaryote or prokaryote appropriate for expressing the ScFv fragment. To obtain a humanised ScFv fragment, it is possible to use the CDR grafting technique. This technique involves selecting complementarity regions (CDRs) of a donor ScFv fragment and grafting them onto the framework of a human ScFv fragment with a known three-dimensional structure (see for example WO 98/45322; EP 0173494).

Modifications to the amino acid sequences of the antibodies according to the invention can be carried out. For example, it may be desirable to improve the binding affinity and/or the biological properties of the antibody. It is known that, when a humanised antibody is produced by simple grafting solely of the CDRs of the VHs and VLs of an antibody derived from a non-human animal in the frameworks (FR) of a human antibody, the capability of binding to the antigen is reduced in comparison with that of an original antibody derived from a non-human animal. It is considered that some amino acid residues of the VHs and VLs of a non-human antibody, not only in the CDRs but also in the FRs, are directly or indirectly associated with the antigen fixing capability. Replacing these amino acid residues with various amino acid residues derived from FRs, VHs and VLs of the human antibody would therefore reduce the binding capability. Consequently, in order to solve this problem, tests must be carried out on the grafted antibodies of human CDRs in order to identify, among the amino acid sequences of the FR, VH and VL of the human antibodies, an amino acid residue that is directly associated with the binding with the antigen, or which interacts with a CDR amino acid residue or which maintains the three-dimensional structure of the antibody and is directly associated with the binding to the antigen. The binding capability could be increased by replacing the amino acids identified by the amino acid residues of the original antibody derived from a non-human antibody. Modifications and changes can be made in the structure of the antibodies of the present invention and in the DNA sequences coding them, while obtaining once again a functional molecule that codes an antibody with the required characteristics.

Another aspect of the present invention relates to the function-preserving variants of the antibodies of the present invention.

The "function-preserving variants" are those in which a given amino acid residue in a protein has been changed without altering the global conformation and the inhibiting function of the suppressor activity of regulatory T lymphocytes. Thus it is possible to replace an amino acid with another having similar properties (for example polarity, hydrogen binding potential, etc.), as long as the function of inhibiting the suppressor activity of regulator T lymphocytes is preserved.

Thus, according to a particular embodiment of the invention, it is possible to have an antibody as previously defined, directed against Galectin-9 and inhibiting the suppressor activity of regulatory T lymphocytes, comprising:
  an H-CDR1 having 1 or 2 difference amino acids with the sequence defined by SEQ ID NO: 2,
  an H-CDR2 having 1 or 2 difference amino acids with the sequence defined by SEQ ID NO: 3,
  an H-CDR3 having 1 or 2 difference amino acids with the sequence defined by SEQ ID NO: 4,
  an L-CDR1 having 1 or 2 difference amino acids with the sequence defined by SEQ ID NO: 6,
  an L-CDR2 having 1 or 2 difference amino acids with the sequence defined by SEQ ID NO: 7,
  an L-CDR3 having 1 or 2 difference amino acids with the sequence defined by SEQ ID NO: 8.

According to another particular embodiment of the invention, an antibody as previously defined, directed against Galectin-9 and inhibiting the suppressor activity of regulatory T lymphocytes, has 1, 2 or 3 difference amino acids with all the six CDRs with sequences as previously defined, that is to say the CDRs with sequences SEQ ID NO: 2, SEQ ID NO: 3, SEQ ID NO: 4, SEQ ID NO: 6, SEQ ID NO: 7 and SEQ ID NO: 8.

According to another particular embodiment of the invention, it is possible to have an antibody as previously defined, directed against Galectin-9 and inhibiting the suppressor actor of regulatory T lymphocytes, comprising:
  an H-CDR1 having 1 or 2 difference amino acids with the sequence defined by SEQ ID NO: 11,
  an H-CDR2 having 1 or 2 difference amino acids with the sequence defined by SEQ ID NO: 12,
  an H-CDR3 having 1 or 2 difference amino acids with the sequence defined by SEQ ID NO: 13,
  an L-CDR1 having 1 or 2 difference amino acids with the sequence defined by SEQ ID NO: 15,
  an L-CDR2 having 1 or 2 difference amino acids with the sequence defined by SEQ ID NO: 16,
  an L-CDR3 having 1 or 2 difference amino acids with the sequence defined by SEQ ID NO: 17.

According to another particular embodiment of the invention, an antibody as previously defined, directed against Galectin-9 and inhibiting the suppressor activity of regulatory T lymphocytes, has 1, 2 or 3 difference amino acids with all the six CDRs of sequences as previously defined, that is to say the CDRs of sequences SEQ ID NO: 11, SEQ ID NO: 12, SEQ ID NO: 13, SEQ ID NO: 15, SEQ ID NO: 16 and SEQ ID NO: 17.

Therapeutic Uses

As mentioned previously, it is known that, in a pathological situation, the regulatory T lymphocytes may cause an inappropriate immune suppression, which then promotes tumour growth. Numerous studies have thus shown that regulatory T lymphocytes reduce the anti-tumoral immune responses, in particular by inappropriately inhibiting the activity of the effector T lymphocytes, thus promoting the development of pathologies of the cancer type.

It has here been demonstrated that, firstly, during activation, Galectin-9 is directly expressed by the regulatory T lymphocytes while it is only very weakly expressed, or not at all, by the effector T lymphocytes, targeting of Galectin-9 making it possible to specifically inhibit the regulatory T lymphocytes without risking causing depletion of effector T lymphocytes. It has moreover been demonstrated that the inhibition of Galectin-9 by an antibody allows inhibition of the suppressor activity of the regulatory T lymphocytes. The antibodies according to the invention, directed against Galectin-9 and inhibiting the suppressor activity of regulatory T lymphocytes, can therefore be used in the treatment of illnesses associated with the suppressor activity of regulatory T lymphocytes, in particular the treatment of cancers.

One object of the invention thus relates to an antibody as previously described for use thereof in the treatment of illnesses associated with the suppressor activity of regulatory T lymphocytes.

A particular embodiment of the invention relates to an antibody, as previously described, used in cancer treatment.

"Cancer treatment" means any treatment capable for example of suppressing a tumour or metastases, reducing the risk of recurrence, slowing down the development of a tumour or metastases, and/or treating the symptoms of the illness.

The cancers aimed by the present invention are those in which the regulatory T lymphocytes exert their suppressor activity. Advantageously, the cancers aimed at by the present invention are those in which the regulatory T lymphocytes are present in large quantities in the tumoral tissue or in the circulation, expansion of the regulatory T lymphocytes generally being correlated with an increase their activation (6). The frequency of the regulatory T lymphocytes can be assessed by any method known to persons skilled in the art, for example by a flow cytometry (FACS) analysis of the intra-tumoral lymphocytes or circulating lymphocytes or by an immuno-histological marking of the tumoral tissue.

In general terms, an antibody as previously defined can therefore be used in the treatment of all types of cancers in which the regulatory T lymphocytes exert their suppressor activity. Numerous types of cancer in which the regulatory T lymphocytes exert their suppressor activity have been the subject of studies and are known to persons skilled in the art.

It is thus known that high levels of regulatory T lymphocytes in tumours are clearly associated with poor prognosis in chronic myeloid leukaemia (7), colon cancer (8), melanoma (9), cancer of the uterus (10), breast cancer (11), pancreatic cancer (12), gastric cancers (13), ovarian cancer (14), primary lymphoma of the central nervous system (15), multiple myelomas (16), prostate cancer (17), Hodgkin's lymphoma or hepatocellular carcinoma (18, 19).

An antibody as previously defined can therefore in particular be used in the treatment of cancer, the cancer being chosen from the group consisting of chronic myeloid leukaemia, colon cancer, melanoma, cancer of the uterus, breast cancer, pancreatic cancer, gastric cancers, ovarian cancer, primary lymphoma of the central nervous system, multiple myelomas, prostate cancer, Hodgkin's lymphoma and hepatocellular carcinoma.

Studies have also demonstrated that some cancers produce large quantities of exosomes carrying Galectin-9 fulfilling an immune suppressor role, that is to say inhibiting the immune response and potentially the anti-tumoral response. Non-limitative examples of cancers producing large quantities of exosomes carrying Galectin-9 are viro-induced cancers, for example nasopharyngeal carcinomas associated with the EBV (Epstein-Barr virus) or hepatocellular carcinomas (CHCs) related to the HCV (hepatitis C virus) or HBV (hepatitis B virus) (20, 21).

An antibody as previously defined can therefore in particular be used in the treatment of cancer, the cancer being a viro-induced cancer, preferably chosen from the group consisting of carcinomas of the nasopharynx associated with the Epstein-Barr virus, and hepatocellular carcinomas related to the hepatitis C virus or the hepatitis B virus.

It has also been demonstrated that increasing the frequency of the regulatory T lymphocytes is a factor predicting recurrence of fibrosis resulting from hepatitis C (22, 23).

An antibody according to the invention can therefore be used in preventing recurrence of fibrosis caused by hepatitis C.

In each of the previously described embodiments, the antibody directed against Galectin-9 and inhibiting the suppressor activity of regulatory T lymphocytes is administered in an appropriate manner to a patient requiring such treatment.

The antibodies according to the invention can be used alone or in combination with any other suitable compound.

One object of the invention relates to a method for treating a cancer, associated with the expression of Galectin-9 and with the suppressor activity of regulatory T lymphocytes, comprising the administration of a therapeutically quantity of an antibody according to the invention to a patient.

The term "patient" is understood to be a human affected, or caused to be affected, by an illness associated with the suppressor activity of regulatory T lymphocytes, in particular a cancer.

The term "therapeutically active quantity" of antibody means a quantity of antibody sufficient for treating such a cancer, having an acceptable benefit/risk ratio for a drug treatment. The quantity of antibody and compositions according to the present invention and the frequency of administration will be determined by clinical studies, by the doctor or by the pharmacist. The "therapeutically active" quantity specific to each of the patients can depend on a certain number of factors, such as the nature and severity of the illness to be treated, the activity of the antibody used, the composition used, the age, weight, general state of health, sex and diet of the patient, the method of administration, the duration of treatment (in a single dose or in a plurality of doses), the drugs used in combination and other factors well known to medical specialists.

According to a particular embodiment of the invention, an antibody directed against Galectin-9 and inhibiting the suppressor activity of regulatory T lymphocytes as previously defined is used in combination with a second agent for treating an illness associated with the suppressor activity of regulatory T lymphocytes, for example an anticancer agent.

Thus, when the use is the treatment of a cancer, the antibody can be used in combination with known therapies against cancer such as for example surgery, radiotherapy, chemotherapy or combinations thereof. For example, the antibody can be used in combination with an adoptive immunotherapy, consisting one or more injections of effector lymphocytes against tumoral antigens, in particular EBV antigens. According to some aspects, other anticancer agents used in combination with the antibody directed against Galectin-9 according to the invention for cancer therapy comprise anti-angiogenics. According to certain aspects, said antibody is co-administered with a cytokine, for example a cytokine that stimulates an anti-tumoral immune response.

One subject matter of the invention therefore relates to a combination product comprising an antibody, as previously defined, and an anticancer agent.

A particular embodiment relates to such a combination product for simultaneous use, separate or spread over time, in the treatment of cancer.

Pharmaceutical Compositions

For administration, the antibody is in general formulated in the form of a pharmaceutical composition. The pharmaceutical composition comprising an antibody according to the invention can be formulated by known methods of the prior art, in which the therapeutic molecule is in combination with at least one excipient.

One subject matter of the invention thus relates to a pharmaceutical composition comprising an antibody as previously described and at least one pharmaceutically acceptable carrier.

A "pharmaceutically acceptable carrier" means any standard pharmaceutical carrier, its administration being able to be tolerated by a patient. For example, sterile phosphate buffered saline solutions are pharmaceutically acceptable.

Pharmaceutically acceptable carriers can normally comprise one or more compounds, for example chosen from excipients, preservatives, solubilisers, buffer agents, albumin, etc. Known excipients are for example starch, gelatin, stearic acid, calcium or magnesium stearate, etc. Persons skilled in the art will be able to determine the compounds suited to the present composition.

The form of the pharmaceutical composition, the administration mode, the dosage and the posology can of course depend, among other things, on the illness to be treated, its symptoms, its severity, and the age, weight and sex of the patient.

Non-limitatively, the pharmaceutical composition according to the invention can be formulated so as to be able to be administered topically, parenterally, nasally, intravenously, subcutaneously/intradermally, conjunctivally or by intramuscular or intraocular method.

The pharmaceutical compositions according to the invention may optionally contain pharmaceutically acceptable excipients suitable for being able to be injected. In particular they may be isotonic sterile saline solutions, monosodium or disodium phosphate, sodium, potassium, calcium or magnesium chloride, etc., or a mixture of these salts. These compositions may also be dry compositions, in particular frozen, lyophilised or refrigerated dry compositions, which, after addition, according to circumstances, of sterile water or physiological water, constitute injectable solutions.

The doses used can be adapted according to various parameters such as in particular the administration mode according to the pathology or alternatively the duration of the treatment envisaged.

To prepare the pharmaceutical compositions, a sufficient quantity of antibody can be dissolved or dispersed in a pharmaceutically acceptable vehicle or an aqueous medium.

The pharmaceutical forms appropriate for use by injection comprise sterile water solutions, dispersions, formulations including sesame oil, or aqueous propylene glycol, as well as sterile powders for the extemporaneous preparation of sterile injectable solutions. In all cases, the form used must be sterile and must be sufficiently fluid to be able to be injected easily by means of a syringe. It must be stable under the production and storage conditions and be protected from contamination by microorganisms, such as bacteria or fungi.

The solutions of the active compounds, whether they be in free form or as salts acceptable from a pharmaceutical point of view, can be prepared with water mixed with a surfactant such as hydroxypropyl cellulose. The dispersions may be done in glycerol, in liquid polyethylene glycols, in a mixture of the two or in oils. These preparations generally contain a preservative in order to prevent the growth of microorganisms under the normal storage and use conditions.

An antibody according to the invention can be formulated in a composition in neutral form or in salt form. Pharmaceutically acceptable salts comprise acid addition salts, formed with the free amino groups of the protein, and formed with inorganic acids such as for example hydrochloric or phosphoric acids, or organic acids such as acetic, oxalic, mandelic, etc. The salts formed with the free carboxyl groups may also be derived from inorganic bases such as sodium, potassium, ammonium, calcium or iron hydroxides, and organic bases such as isopropylamine, trimethylamine, histidine, procaine, etc.

After formulation in the form of a drug, the solutions can be administered in a manner compatible with the dosage of the formulation and in a therapeutically active quantity. The drugs may be administered as described above but also in the form of capsules that release them.

FIGURES

Figure 1:
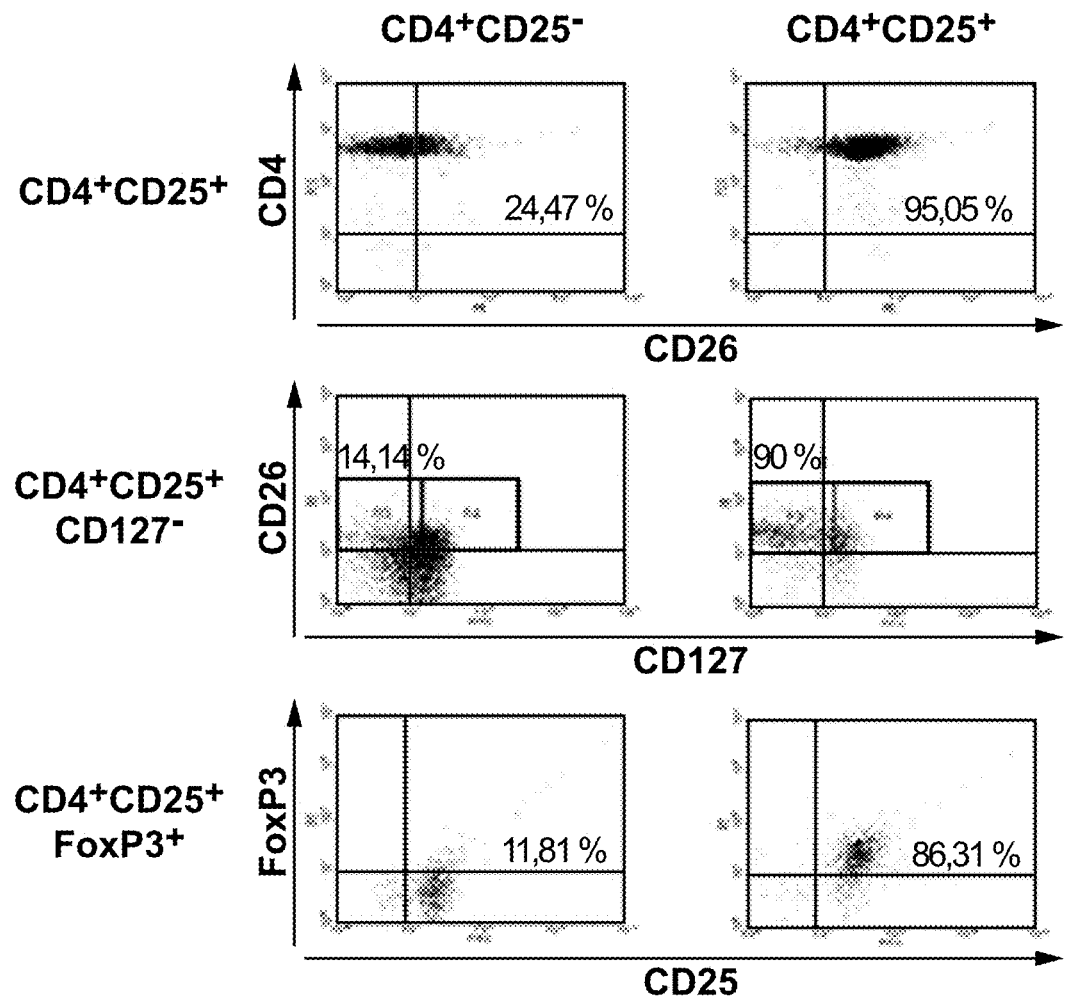

FIG. 1: Phenotype analysis by multiparametric flow cytometry of the natural regulatory T lymphocytes isolated from human blood.

Figure 2:
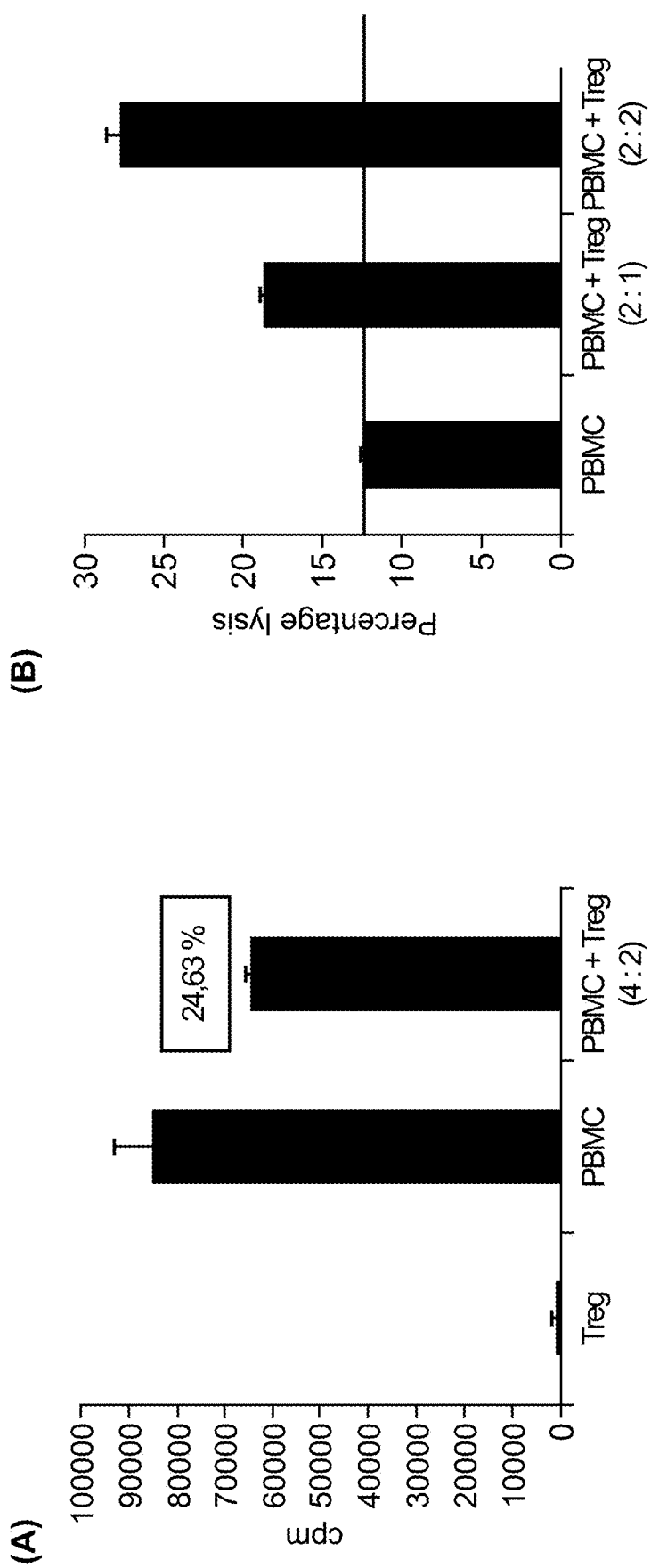

FIG. 2: Analysis of the suppressive function of natural regulatory T lymphocytes isolated ex vivo. (A) Analysis of the inhibition of the proliferation of PBMCs activated by the autologous regulatory T lymphocytes in cpm. (B) Analysis of the cytolysis percentage of the PBMCs activated by the autologous regulatory T lymphocytes.

Figure 3:
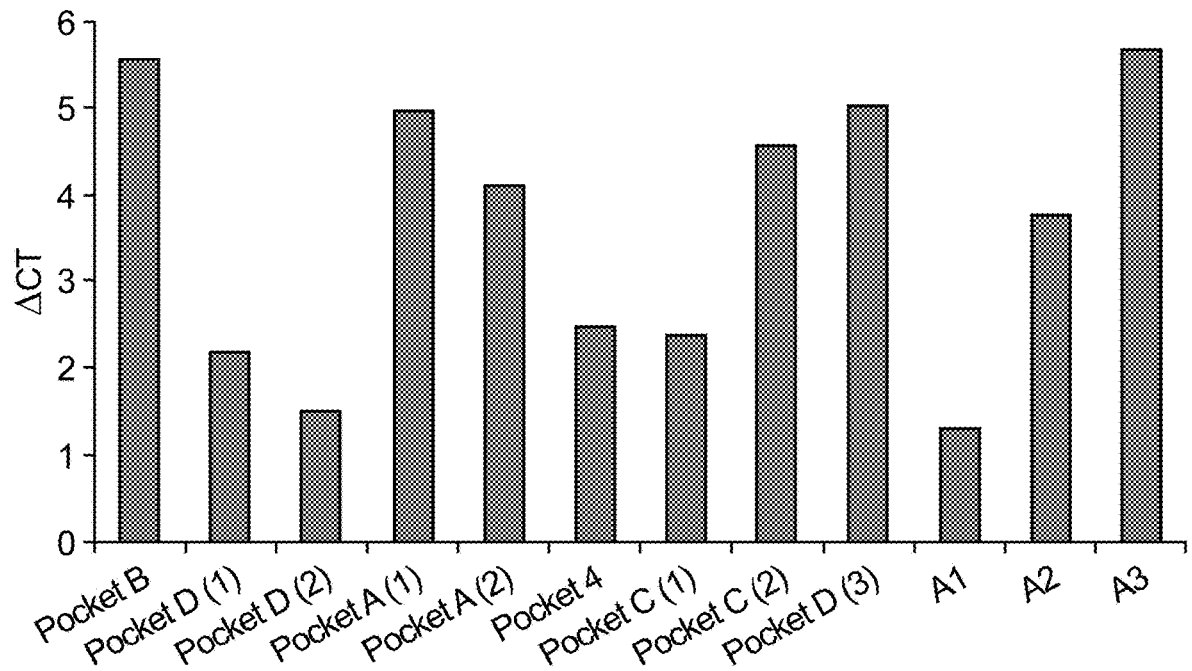

FIG. 3: Analysis by qPCR of the expression of the gene coding Galectin-9 in human regulatory T lymphocytes (n=12). 1) 8, D1, D2, A1, A2 represent the blood pockets. CT represents the cycle threshold. It is the mean threshold as from which detection of the amplification of the gene of Galectin-9 commences. The results are expressed in $\Delta$CT following normalisation with four housekeeping genes ($\beta$-actin, GAPDH, HPRT, ubiquitin).

[$\Delta$CT=CT (the sample)–CT (average of the housekeeping genes)]

Figure 4:
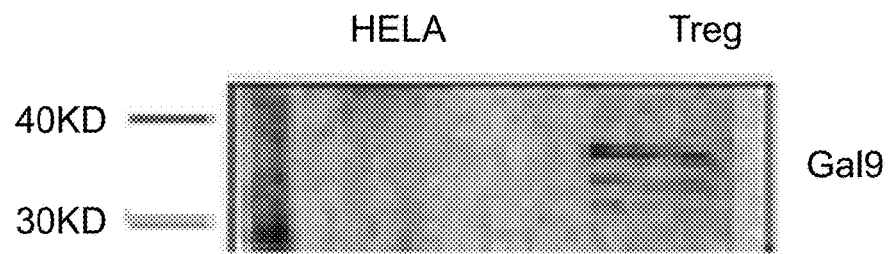

FIG. 4: Analysis by Western Blot of the expression of the three isoforms of Galectin-9 in the human regulatory T lymphocytes. The HeLa cells are used as a negative control.

Figure 5:
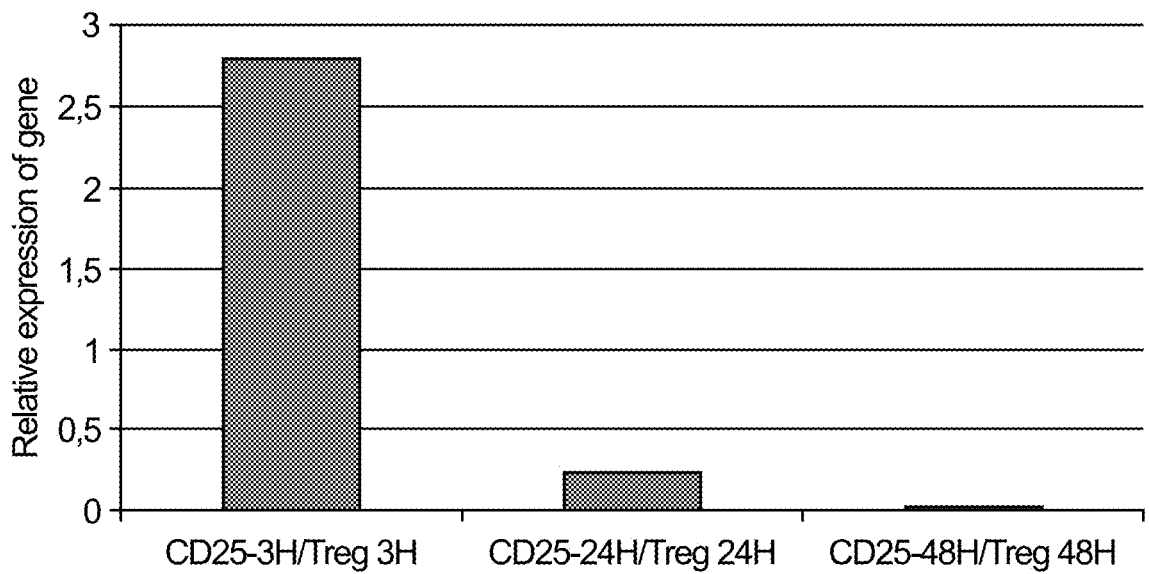

FIG. 5: Analysis by qPCR of the expression of the gene coding Galectin-9 in conventional T lymphocytes during activation (n=4).

Figure 6:
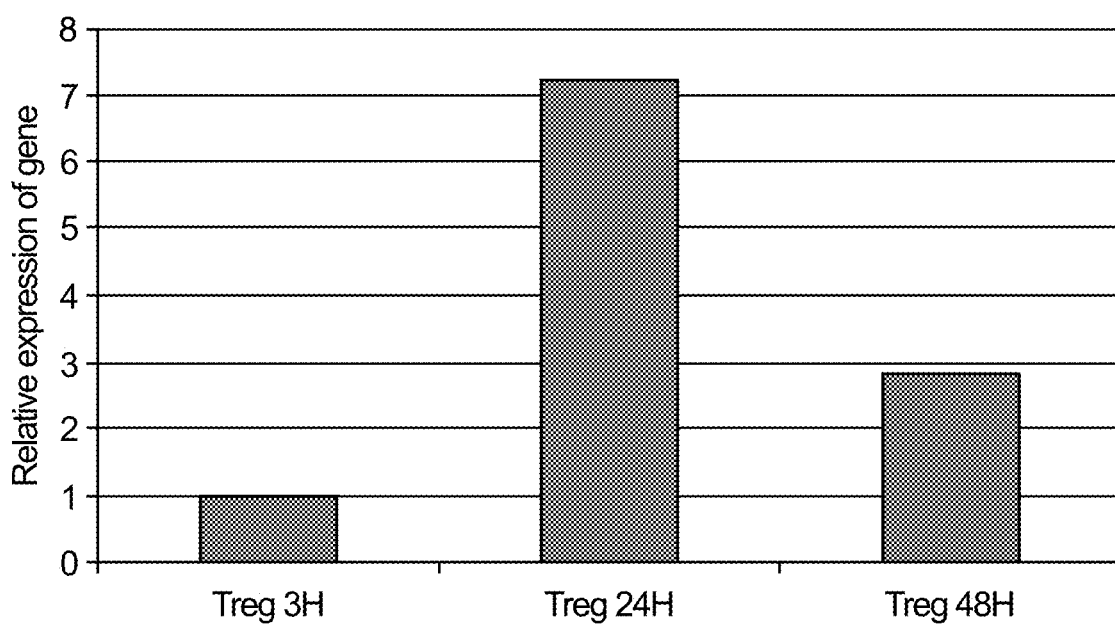

FIG. 6: Analysis by qPCR of the expression of the gene coding Galectin-9 in human regulatory T lymphocytes during activation (n=4).

Figure 7:
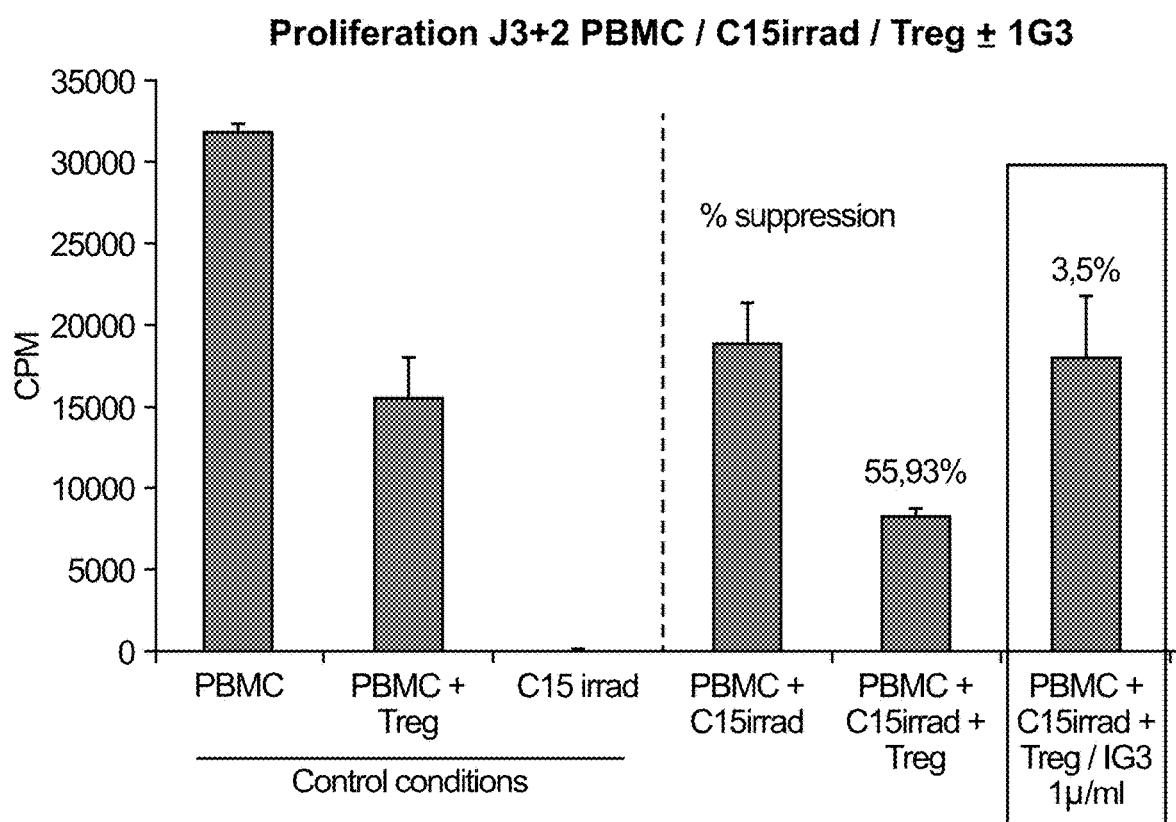

FIG. 7: Analysis of the inhibition of the suppressor activity of regulatory T lymphocytes by the anti-Gal9 1G3 antibody by analysis of the proliferation of the PBMCs in the presence of irradiated C15s, in the presence or not of regulatory T lymphocytes, and in the presence or not of 1G3 antibodies at a concentration of 1 μg/ml.

Figure 8:
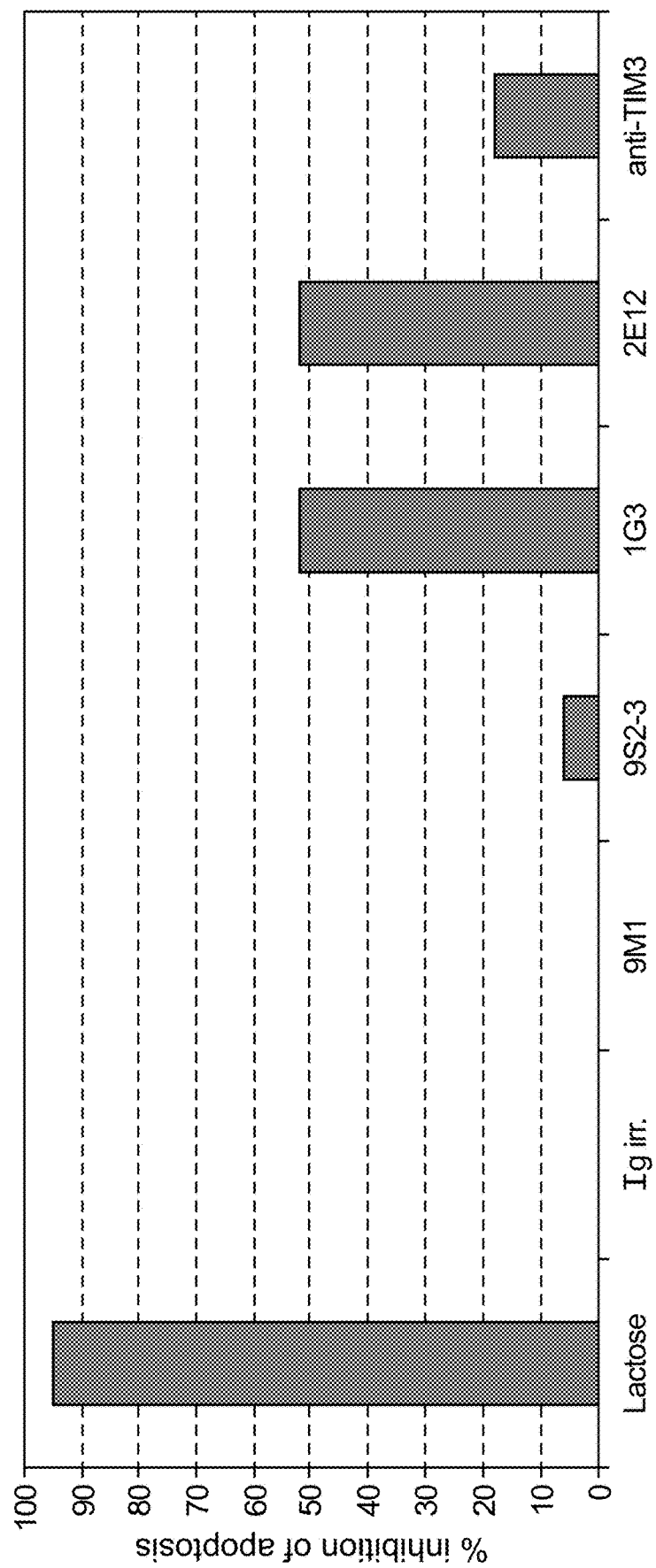

FIG. 8: Analysis of the inhibition of Jurkat apoptosis caused by Galectin-9.

With 1 hour of preincubation of Galectin-9 S at 1 μg/ml and antibodies at 5 μg/ml (9M1 antibody (anti-Galectin-9), 9S2-3 (anti-Galectin-9), 1G3 (anti-Galectin-9), an anti-TIM3, 2E12 antibody (anti-Galectin-9)).

Figure 9:
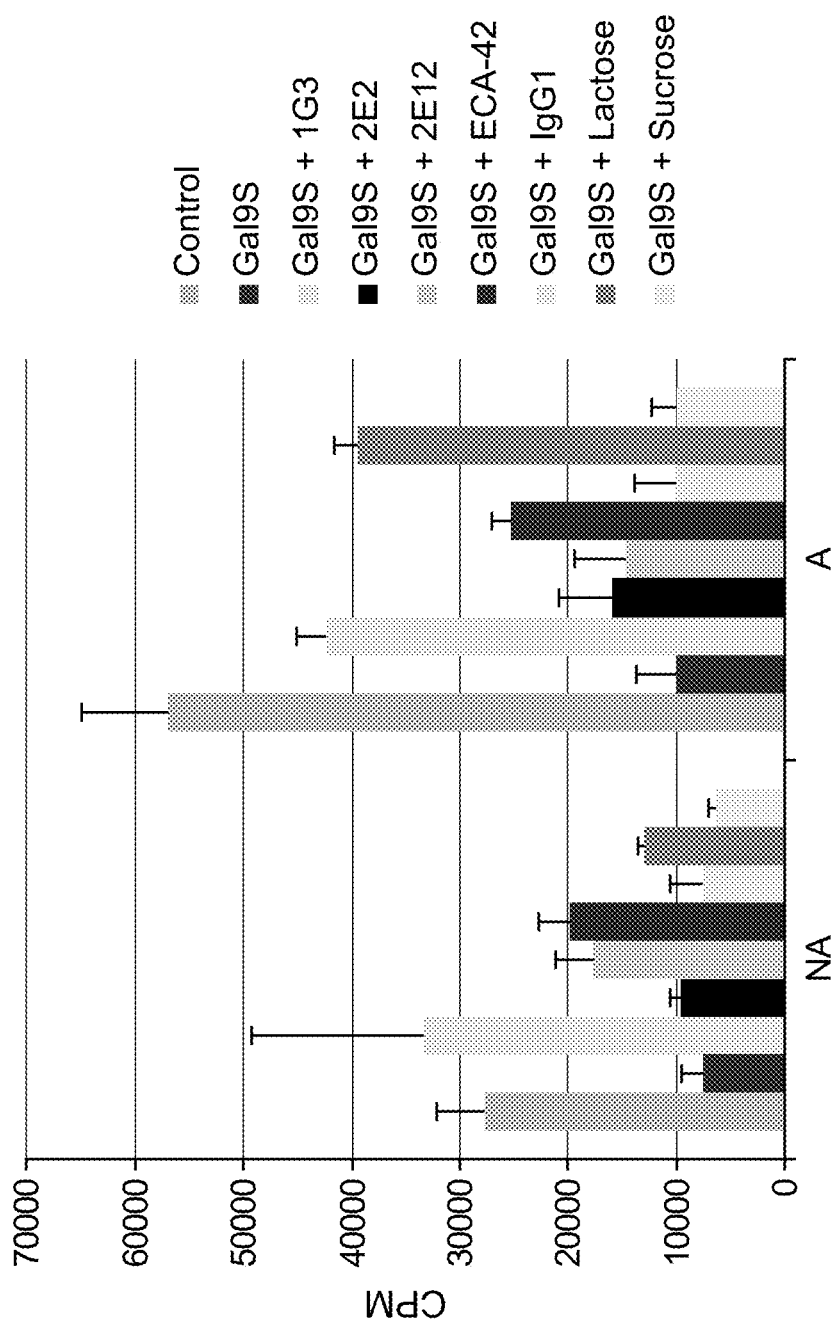

FIG. 9: Analysis of the restoration of proliferation on activated cells ("A", with anti-CD3 and anti-CD28) and non-activated (NA), after treatment with Galectin-9 (antibodies tested=ECA-42 (anti-Galectin-9), 1G3 (anti-Galectin-9), 2E2 (anti-TIM3) and 2E12 (anti-Galectin-9)). The control corresponds to the culture medium.

Figure 10:
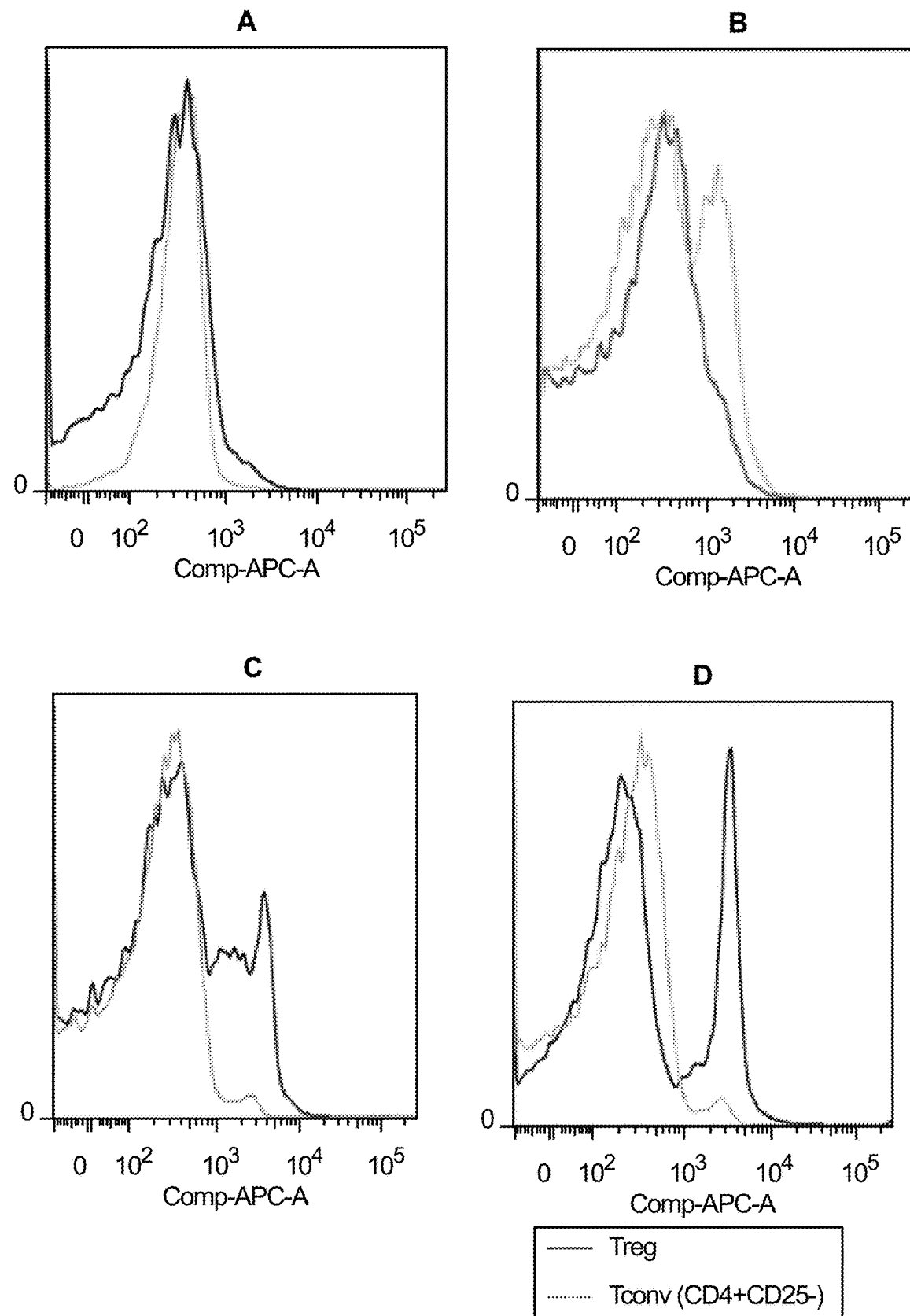

FIG. 10: Analysis of the expression of Galectin-9 by flow cytometry (FACS).

A: Expression of Galectin-9 from regulatory T lymphocytes and freshly isolated CD4+ Tconv cells (n=2 donors).

B: Expression of Galectin-9 extracted from regulatory T lymphocytes and CD4+ Tconv cells after 24 hours of activation (n=5 donors).

C: Expression of Galectin-9 extracted from regulatory T lymphocytes and CD4+ Tconv cells after 48 hours of activation (n=5 donors).

D: Expression of Galectin-9 extracted from regulatory T lymphocytes and CD4+ Tconv cells after 72 hours of activation (n=5 donors).

Figure 11:
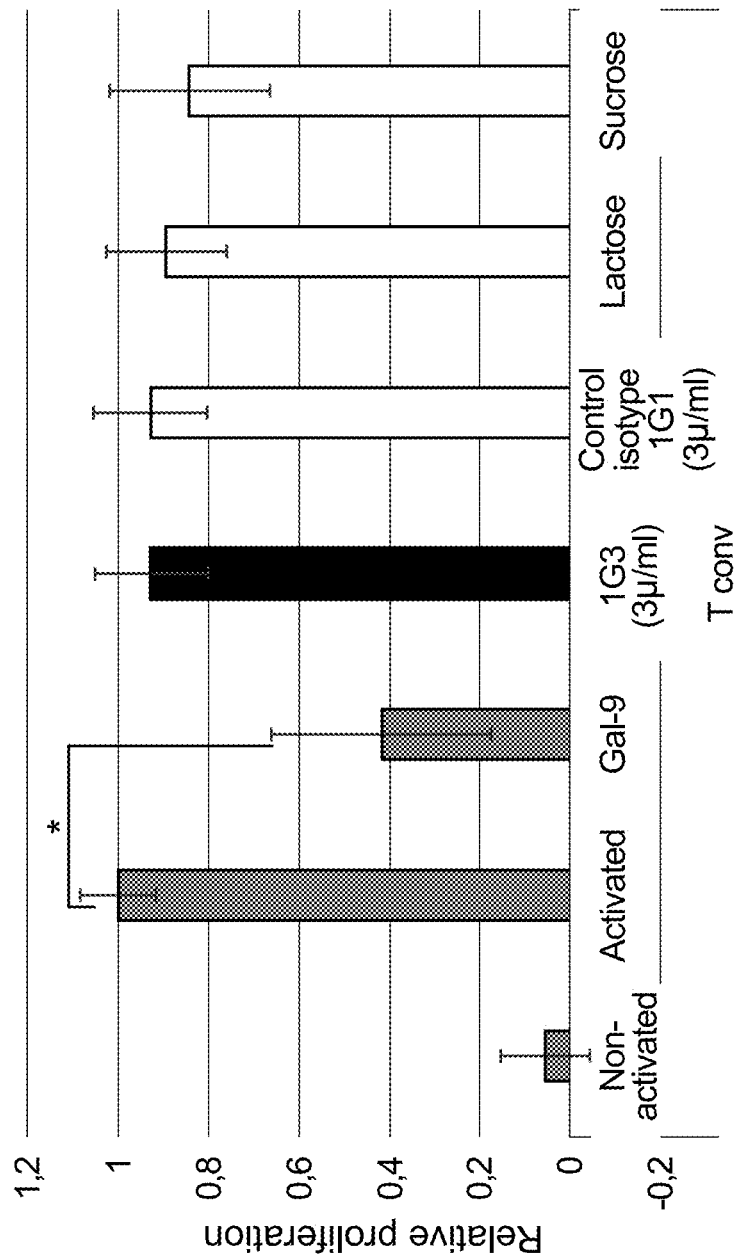

FIG. 11: Relative proliferation of Tconv lymphocytes under various conditions after 3 days of culture (cells activated or not, in the presence of Galectin-9 and with 1G3 ("anti-X"), a control isotope μgG1), an inhibitor (lactose) and a reference inhibiter (sucrose)).

Figure 12:
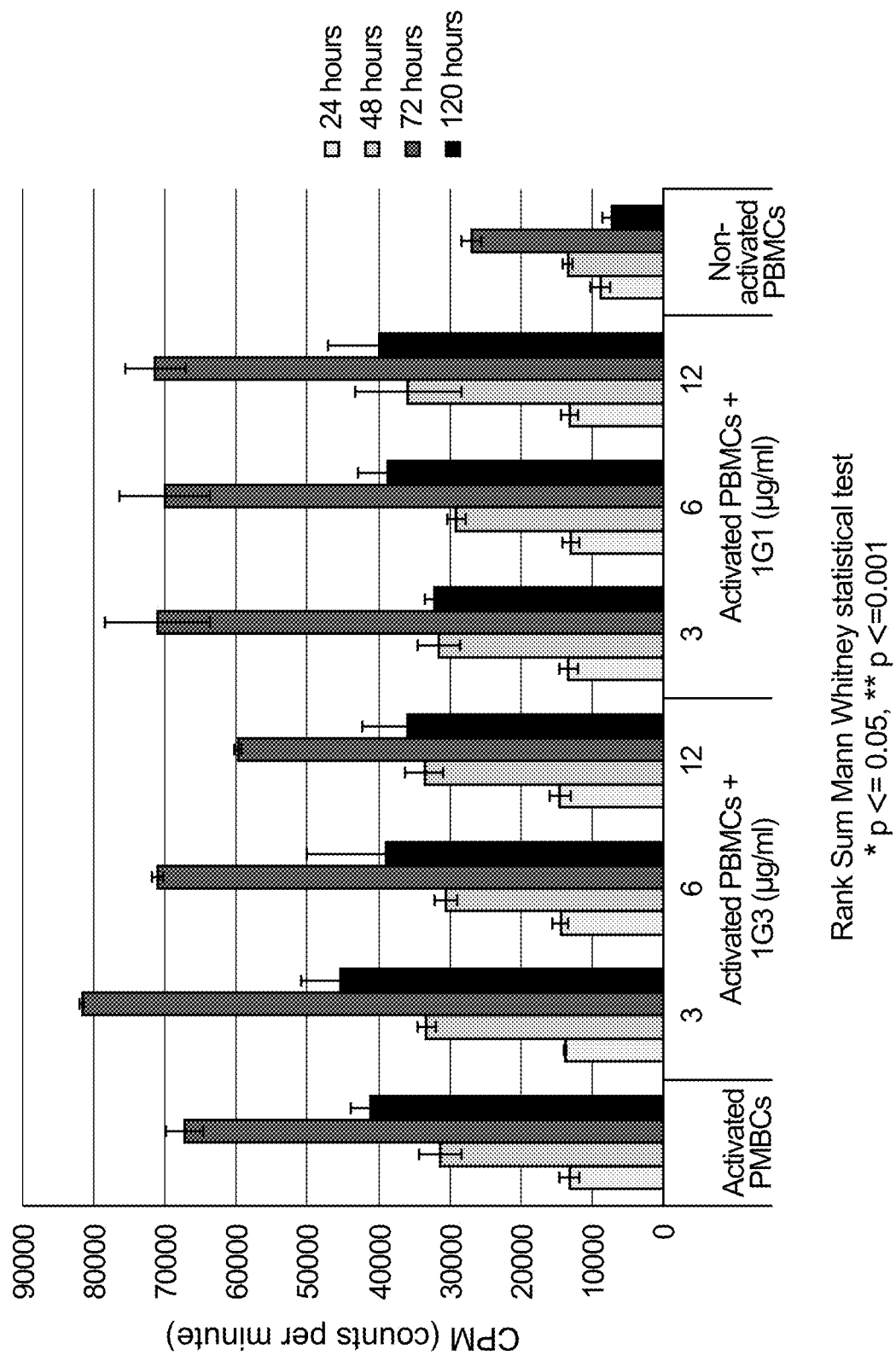

FIG. 12: Proliferation of PBMCs under various conditions after 5 days of culture (cells activated or not, in the presence of 1G3 or of a control isotope μgG1).

Figure 13:
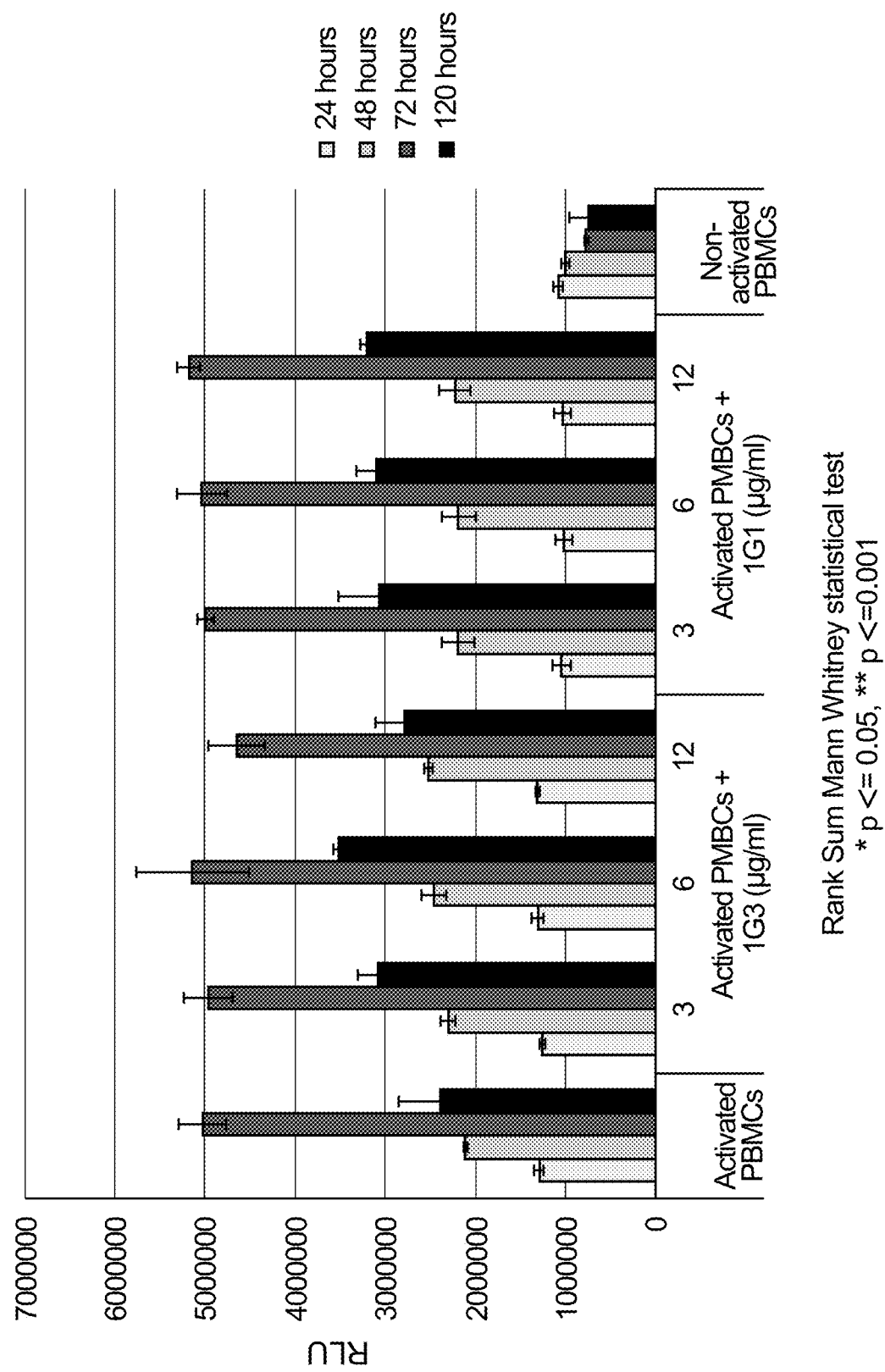

FIG. 13: Viability of PBMCs under various conditions after 5 days of culture (cells activated or not, in the presence of 1G3 or of a control isotope μgG1).

Figure 14:
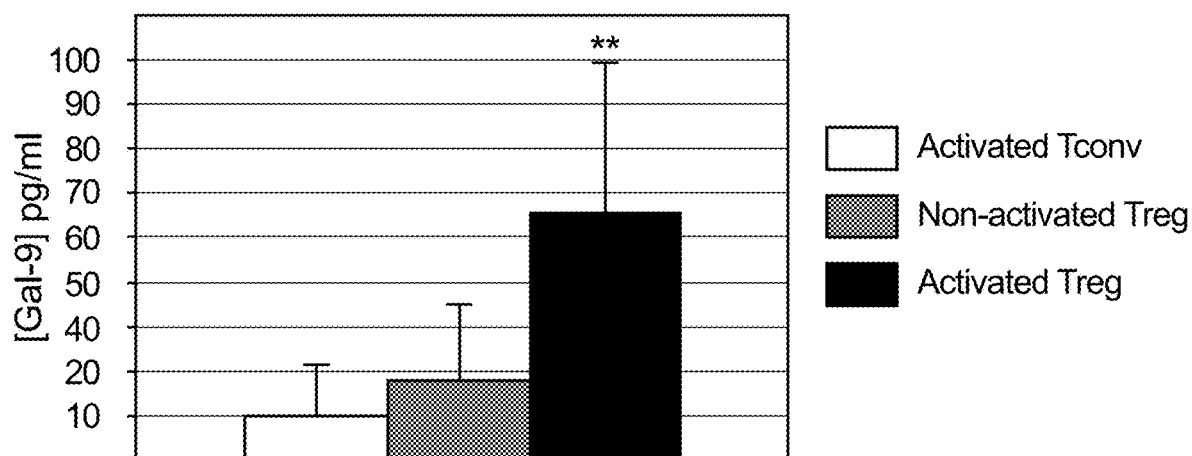

FIG. 14: Measurement of the secretion of Galectin-9 by conventional CD4+ Ts ("Tconv") and regulatory T lymphocytes ("Tregs") under non-activated and activated conditions (test carried out after 48 hours of culture).

Figure 15:
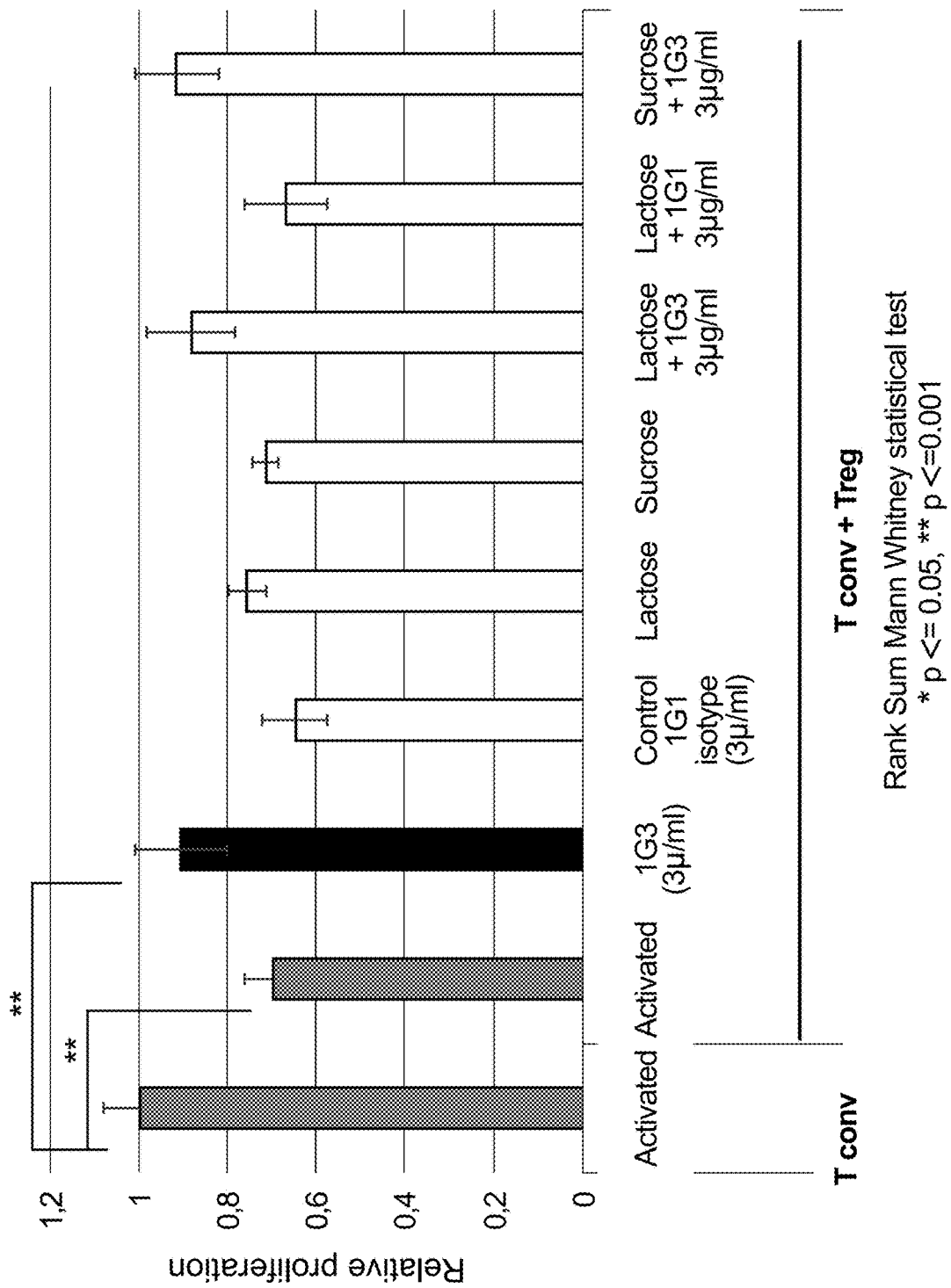

FIG. 15: Relative proliferation of conventional T lymphocytes in co-culture with autologous regulatory T lymphocytes under various conditions (cells activated, in the presence of 1G3 ("anti-X"), a control isotype (IgG1), an inhibiter (lactose) and/or a reference inhibiter (sucrose)).

Figure 16:
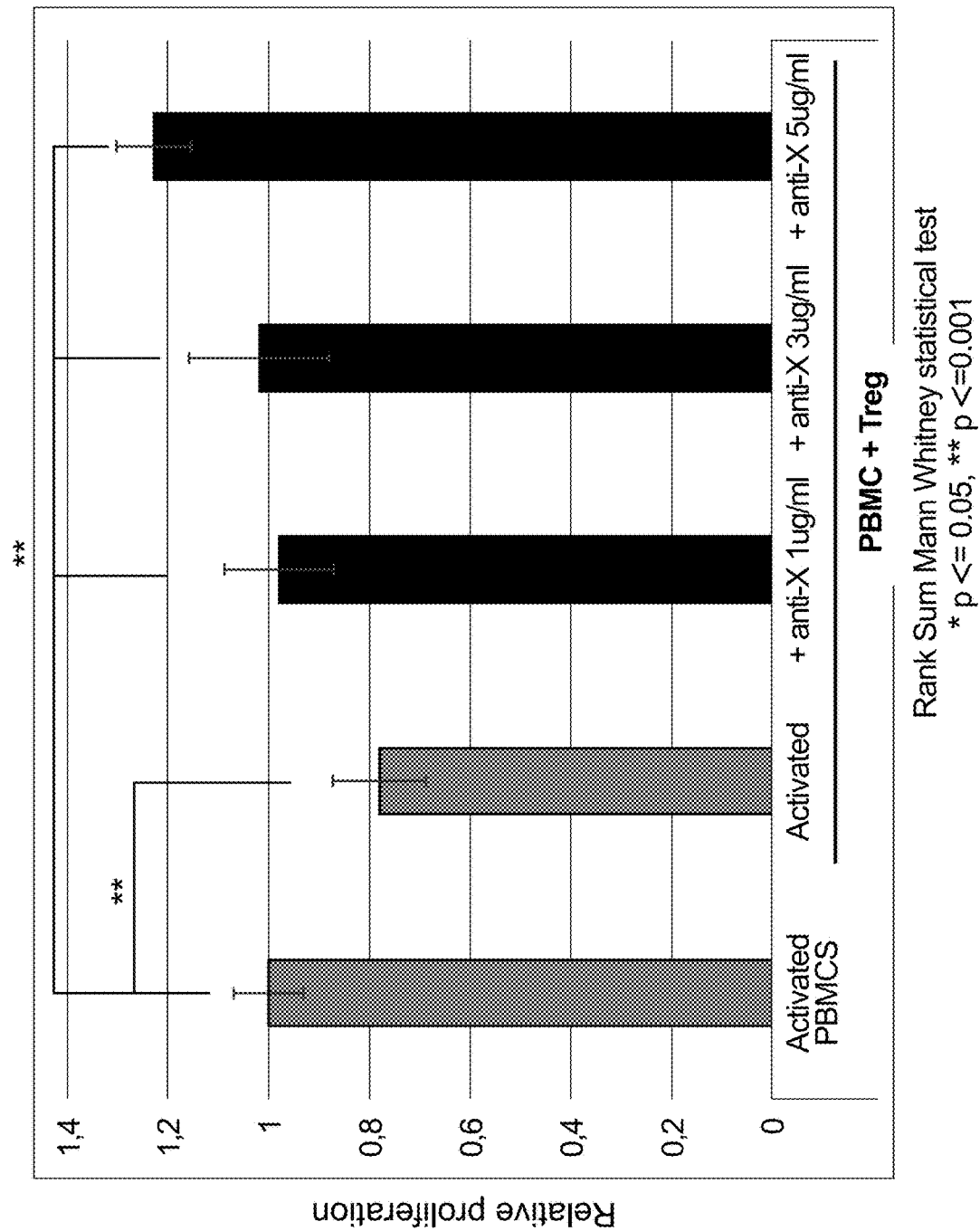

FIG. 16: Relative proliferation of PBMCs in the presence of regulatory T lymphocytes and various concentrations of 1G3 (1 μ/ml, 3 μ/ml, 5 μ/ml).

Figure 17:
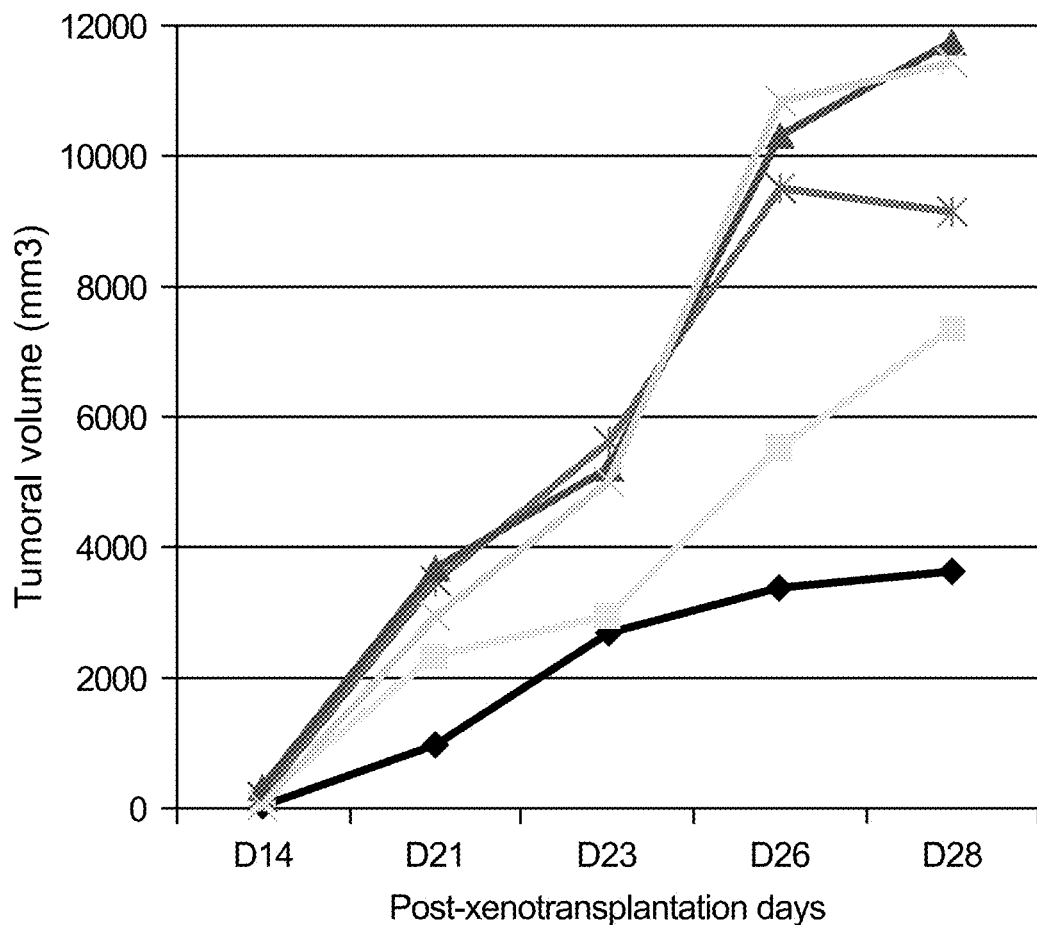

FIG. 17: Tumour volume under various treatments: PBMCs alone (control); PBMC+Treg+1G3 (activated); PBMC+Treg+IgG1 (activated); without PBMC+1G3 (activated); without PBMC+IgG1 (activated).

FIG. 18: Graphical representation of the weight of mice as a function of days.

A and B: Independent experiments with xenotransplanted SCID mice ($50.10^6$ PBMCs+6% Treg) and treated with 1G3 or the control isotype IgG1 (20 μg/mouse).

FIG. 19: Graphical representation of the weight of the mice as a function of days.

A: Xenotransplanted SCID mice ($20.10^6$ PBMCs+10% Treg) and treated with 1G3 or the control isotype IgG1 (2 μg/mouse).

B: Xenotransplanted SCID mice ($50.10^6$ PBMCs+6% Treg) and treated with 1G3 or the control isotype IgG1 (20 μg/mouse).

C: Xenotransplanted SCID mice ($50.10^6$ PBMCs+6% Treg) and treated with 1G3 or the control isotype IgG1 (20 μg/mouse).

D: Xenotransplanted SCID mice ($50.10^6$ PBMCs+6% Treg) and treated with 1G3 or the control isotype IgG1 (200 μg/mouse).

Figure 20:
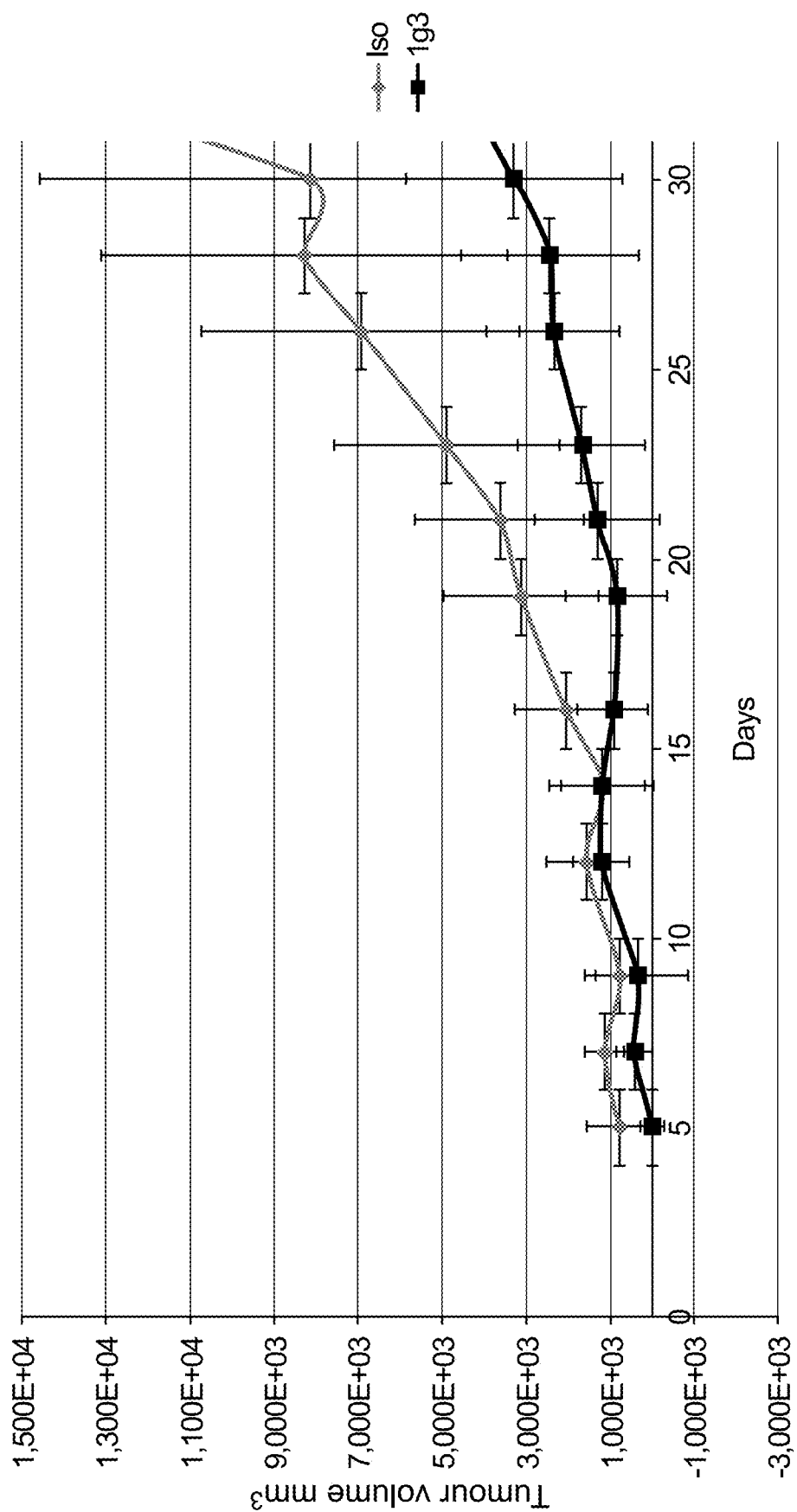

FIG. 20: Averages of the tumour volume measured manually ($mm^3$) of 6 independent experiments (20 μg of 1G3 per mouse, $50.10^6$ PBMC+6 to 8% Treg, in comparison with the control isotype IgG1) (manual measurement). (*$p<=0.05$, **$p<=0.001$).

FIG. 21: Measurements of the tumour volume measured by bioluminescence.

A: Xenotransplanted SCID mice ($50.10^6$ PBMCs+6% Treg) and treated with 1G3 or the control isotype IgG1 (2 μg/mouse).

B: Xenotransplanted SCID mice ($50.10^6$ PBMCs+6% Treg) and treated with 1G3 or the control isotype IgG1 (20 μg/mouse).

C: Xenotransplanted SCID mice ($40.10^6$ PBMCs+6% Treg) and treated with 1G3 or the control isotype IgG1 (20 μg/mouse).

D: Xenotransplanted SCID mice ($50.10^6$ PBMCs+6% Treg) and treated with 1G3 or the control isotype IgG1 (200 μg/mouse).

Figure 22:
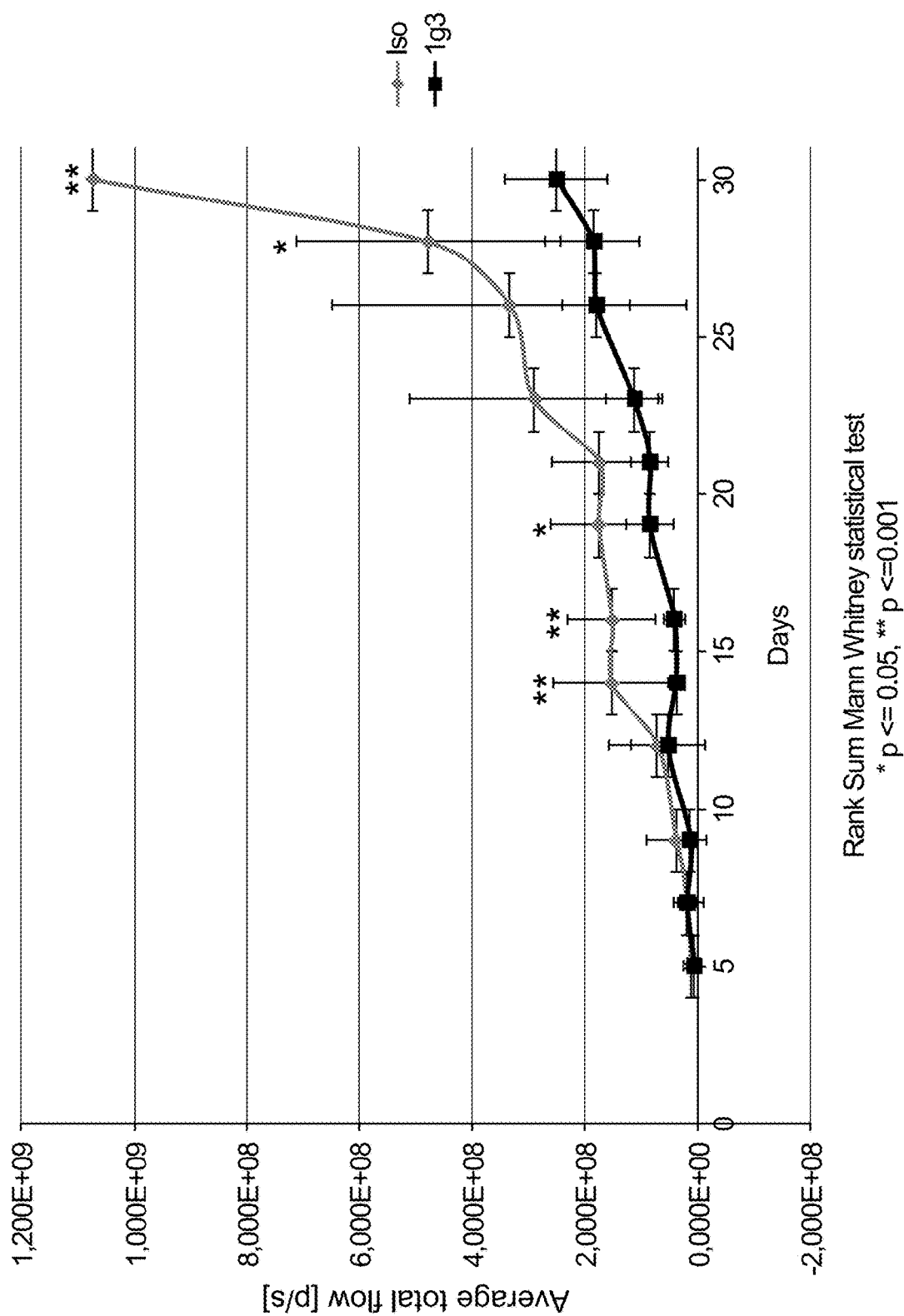

FIG. 22: Averages of the tumour volume measured by bioluminescence of 6 independent experiments (20 μg of 1G3 or IgG1 per mouse, $50.10^6$ PBMC+6% to 8% Treg) (measurement of total flux) (*$p<=0.05$, **$p<=0.001$).

Figure 23:
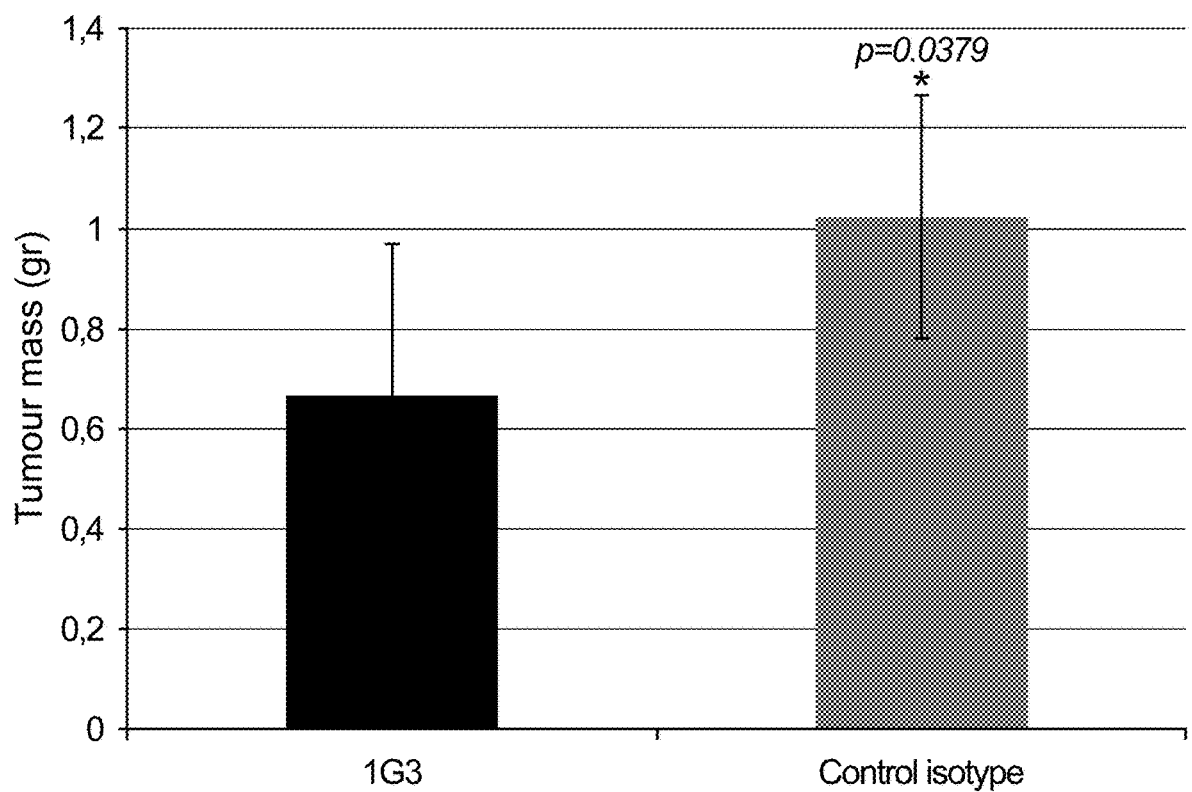

FIG. 23: Tumour masses in grams measured over 6 independent experiments (20 μg of 1G3 or IgG1 per mouse, $50.10^6$ PBMC+6% to 8% Treg). (*$p<=0.05$, **$p<=0.001$).

Figure 24:
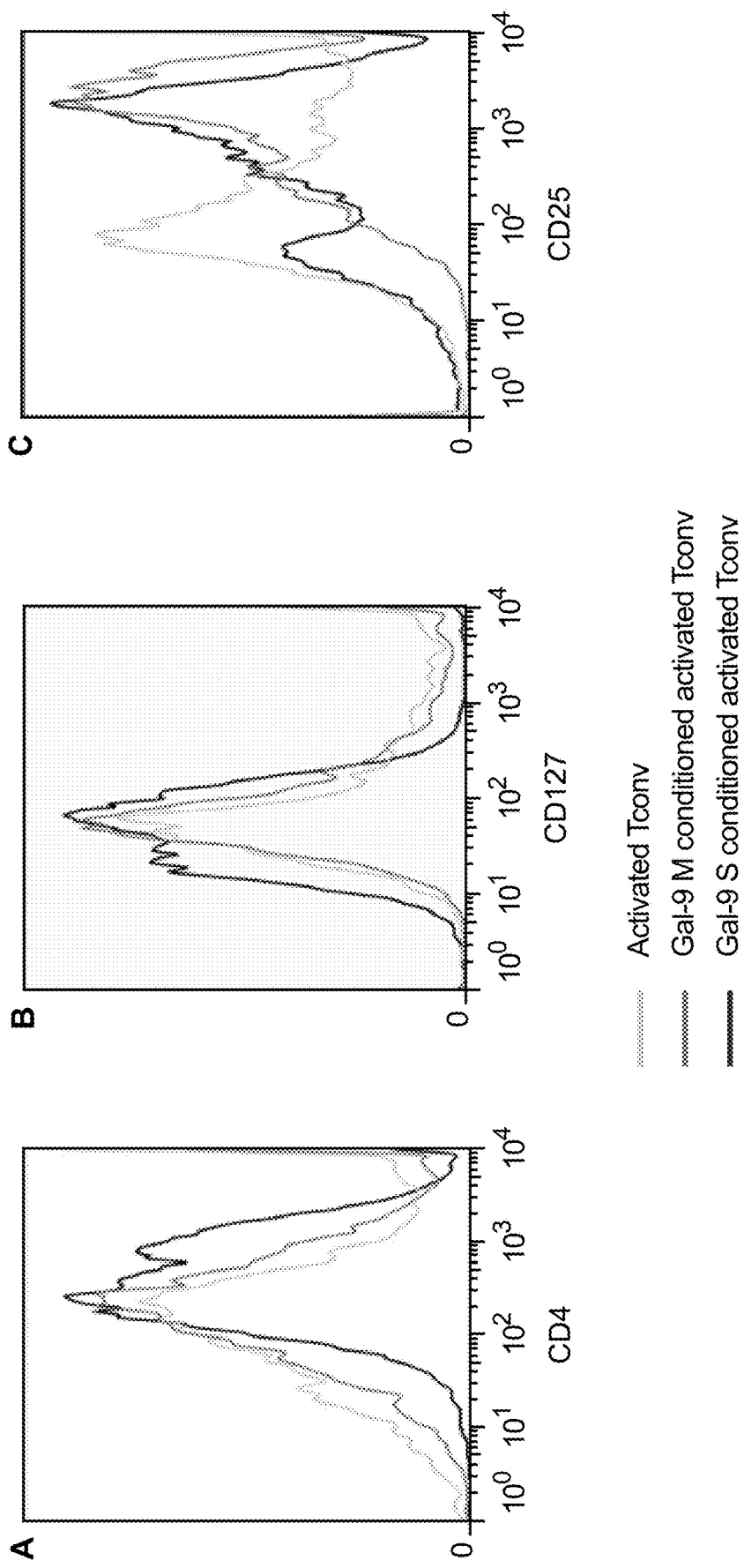

FIG. 24: Comparative cytometric analysis of the expression of various markers after 5 days of conditioning. A: Expression of CD4 between activated Tconv (light grey), activated with Gal-9 M (medium grey) or Gal-9-S (black). B: Expression of CD127 between Tconv activated (light grey), activated with Gal-9 M (medium grey) or Gal-9-S (black). C: Expression of CD25 between Tconv activated (light grey), activated with Gal-9 M (medium grey) or Gal-9-S (black).

Figure 25:
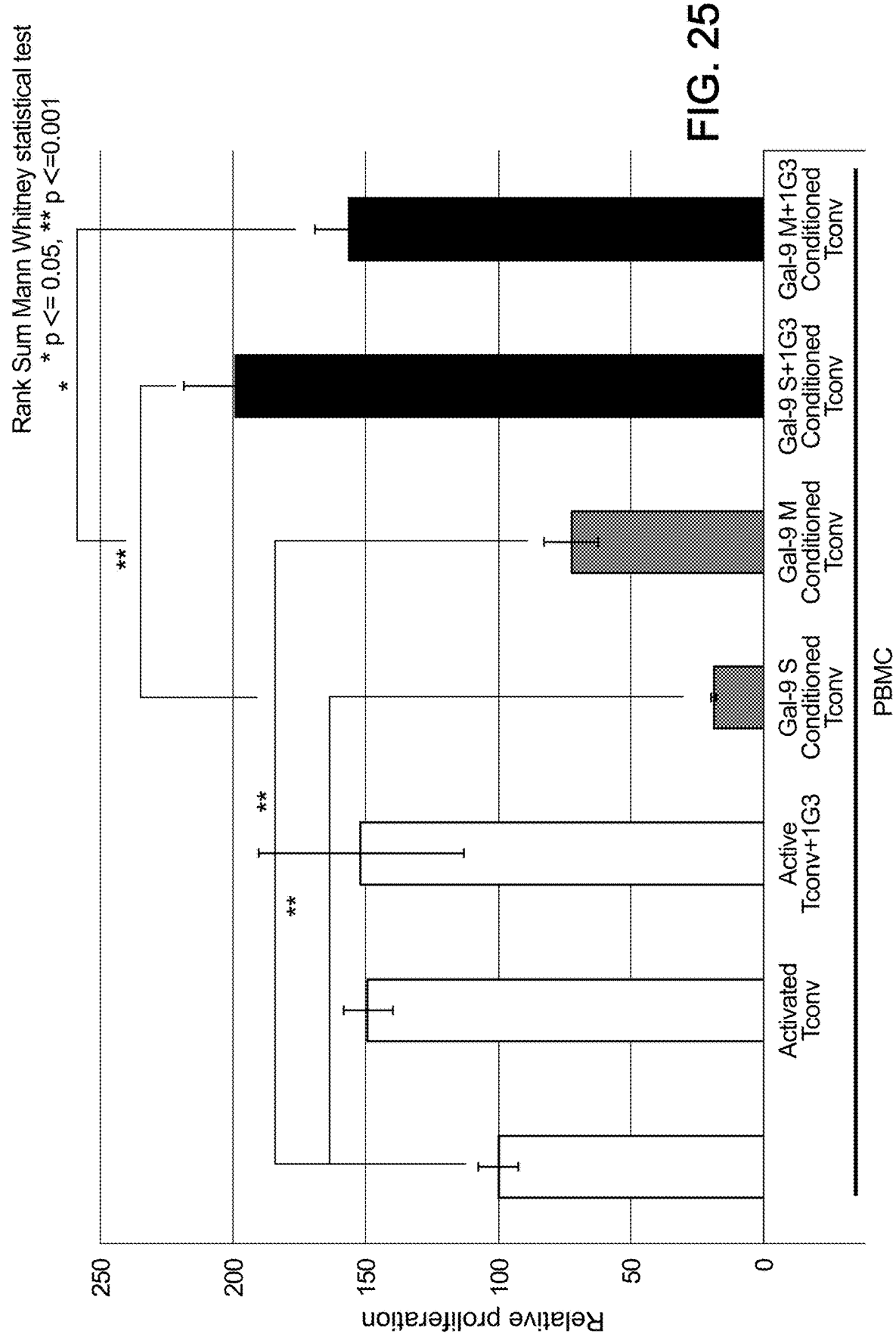

FIG. 25: Relative proliferation of PBMCs according to various conditions after 3 days of culture with Tconv conditioned by the M or S form of Gal-9 for 5 days. (*$p<=0.05$, **$p<=0.001$).

Figure 26:
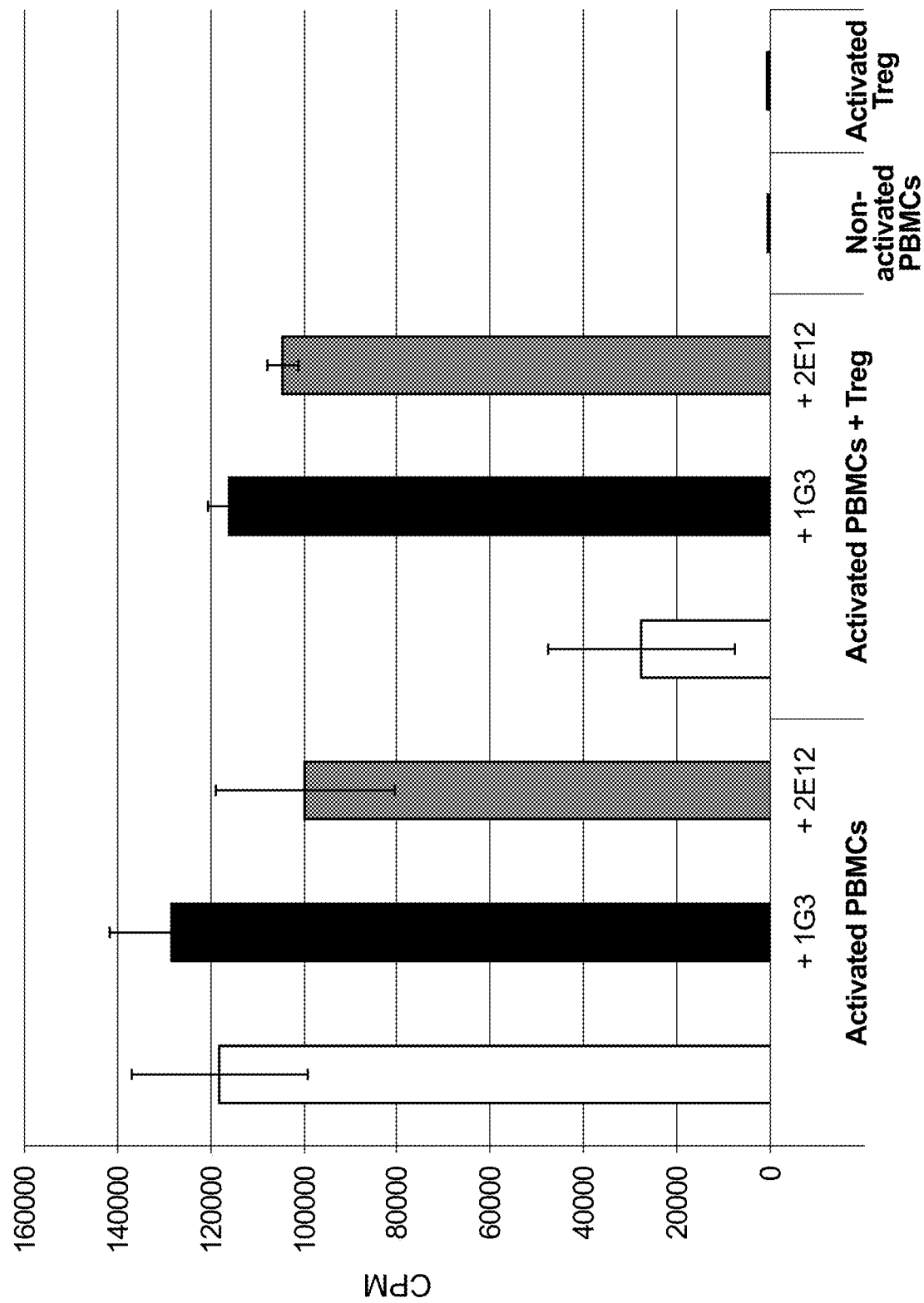

FIG. 26: Analysis of the inhibition of the suppressor activity of regulatory T lymphocytes by the anti-Gal9 antibody 1G3 and the anti-Gal9 antibody 2E12 (at a concentration of 1 μg/ml), by analysis of the proliferation of the PBMCs co-cultivated with regulatory T lymphocytes.

EXAMPLES

1. Equipment and Methods
Donors, Cell Lines and Culture Conditions
Donor Cells

Healthy donor cells were isolated from blood coming from the Etablissement Français du Sang—Nord de France (EFS), in accordance with an official ethics agreement between the latter and the Centre National de la Recherche Scientifique (CNRS)—Délégation Nord Pas-de-Calais et Picardie. The study was approved by the Institut de Biologie de Lille (CNRS) and the Institutional Committee of the EFS, and each of the donors had previously signed an explained consent.

NPC Cell Lines

C15 tumoral cell lines are derived from an EBV-positive NPC (nasopharyngeal carcinoma) xenotransplanted and propagated continuously in SCID mice subcutaneously every 6-7 weeks. All the animal experiments were carried out by qualified personnel, in accordance with French and European regulations, in the breeding farm of the Institut Pasteur de Lille (France). The C15 cells were recovered from the xenotransplanted tumours, then irradiated (5000 rads) before being preincubated with the immune cells simulating a tumour context.

Jurkat Human T Lymphocyte Line

The Jurkat line was established from a human T lymphocyte leukaemia. It has a phenotype of CD4+ lymphocytes.

Cell Culture Conditions

The standard culture medium used is RPMI 1640 (Invitrogen, Paisley, UK) supplemented with 10% AB human serum (BioWest, Nuaillé, France), 2 mM of L. Glutamine, 1 mM of sodium pyruvate, 10 mM of non-essential amino acids, 10 mM of HEPES, 50 μ/ml of streptomycin, 50 μg/ml of gentamycin and 50 μM β mercaptoethanol. The cells were incubated at 37° C. in a controlled atmosphere (5% $CO_2$ and 95% humidity) in a Hera Cell 150 incubator (Thermo Electron, Cergy Pontoise, France). Where applicable, the PBMCs and the CD4+ T cells were activated with an anti-CD3 antibody (1 μg/ml) (Clinisciences, Montrouge, France), which fixes to the plate after an incubation of 2 hours at 37° C. before culture, and an anti-CD28 soluble antibody (100 ng/ml) (Clinisciences) added extemporaneously.

Isolation of Human Immune Cells
Isolation of PBMCs

The peripheral blood mononuclear cells (PBMCs) of healthy donors were isolated by standard density gradient centrifugation using Ficoll Paque PLUS (Amersham Biosciences, Uppsala, Sweden).

Isolation of CD4+ T cells

CD4+ T cells were isolated from the PBMCs using a negative selection protocol in accordance with the instructions of the manufacturer (Miltenyi Biotec, Berlin, Germany). Briefly, the PBMCs are incubated for 10 minutes with a cocktail of biotinylated antibodies directed against CD8, CD14, CD16, CD19, CD36, CD56, CD123, TCRγ/δ and glycophorin A. Anti-biotin magnetic balls were then added for 15 minutes. The cells to be eliminated are retained magnetically in a magnetic activated cell sorting column (MACS®) placed in an MACS® separator. The cells to be isolated pass through the column and are collected and enriched with non-marked cells, depleted of non-targeted cells. Flow cytometry analysis shows that more than 98% of the isolated cells are CD4+ cells.

Isolation of Regulatory T Lymphocytes

The isolation of human regulatory T lymphocytes from adult donor PBMCs was carried out using a kit for isolation of CD4+CD25+ regulatory T lymphocytes (Miltenyi Biotech, Germany) in accordance with the instructions of the manufacturer. The fraction of the CD4+CD25− T cells was preserved for flow cytometry and chemoattraction experiments. The flow cytometry analysis shows, constantly, a greater than 95% enrichment of the CD4+CD25+ fraction.

Cell Proliferation Test $1.10^5$ cells (PBMCs or CD4+ T cells) were incubated with [3H methyl] thymidine during the last 18 hours of culture and collected on a glass-fibre filter (Printed Filtermat A, Wallac, Turku, Finland) using a Tomtec collector (Wallac). The filter was next sealed in a bag after drying and the addition of scintillation liquid (Beckman Coulter, United States). Proliferation was measured after incubation in the presence of [3H]thymidine (1 μCi/well) (PerkinElmer, Courtaboeuf, France) for the last 18 hours before collection. The radioactivity was measured using a β meter (1450 Trilux, Wallac, Finland). Each proliferation test was carried out in three examples and estimated in counts per minute (cpm). According to the experiment, the proliferation tests were carried out in the presence of 1 μg/ml of the short isoform of recombinant Galectin-9 (Gal9S) as supplied by Dr. Toshiro Niki (Galpharma, Japan), 1 μg/ml or a range of the anti-Galectin-9 antibody 1G3, a non-relevant anti-IGg1 antibody serving as a negative control (eBioscience, United Kingdom), 10 μg/ml of C15 exosomes, and 5 mM of lactose or sucrose (Sigma Aldrich).

Cell Lysis

The cell lysis measurement technique is based on the use of a cytotoxicity measurement kit (CytoTox-Glo Assay, Promega, USA) which measures a luciferase activity proportional to cell proteases released after cytolysis. The tests are carried out by putting $6.10^5$ CD4+CD25+ and $2.10^5$ autologous PBMCs in co-culture. The cells are cultivated in round-bottomed 96-well plates (Maxisorb Nunc. Denmark), in 200 μl of culture medium (RPMI-1640, 1% 2 mM L-glutamine, 0.02 mM of sodium pyruvate, 100 μ/ml of penicillin, 100 μg/ml of streptomycin, 10% of decomplemented AB human serum) (GIBCO BRL™, Invitrogen®, GB). The cells are activated by 1 μg/ml of anti-CD3, previously coated on the plates (2 hours at 37° C.), and 100 ng/ml of anti-CD28. After 48 hours of culture, 50 μl of reagent (aminoluciferin-Glo) is deposited in each well. After light agitation, the culture plates are incubated for 15 minutes at ambient temperature and away from light. A first measurement of the luminescence is made with a luminometer (Centro LB960, C Berthold Technologies, France) and is proportional to the quantity of cells lysed by the regulatory T lymphocytes. Next 50 μl of a digitonin solution is deposited in each well in order to cause total lysis of the cells. The plates are next agitated and then incubated for 15 minutes, at ambient temperature and in darkness, before making the second luminescence measurement. The tests are carried out in triplicate and the results are expressed as a lysis percentage.

Lysis percentage=cell viability/average total lysis−background noise

Cell viability=average total lysis−cytolysis

Cytolysis=average lysis caused by Treg lymphocytes−background noise

Test of Induction of Apoptosis in Jurket Cells

Jurkat cells cultivated in 5% RPMI of foetal calf's serum are transferred into a serum-free medium (Hybridoma SFM—Life Technologies) and then incubated in the presence of 30 nM Galectin-9 for 24 hours in a well of a 96-well plate (100,000 cells/well). The counting of the cells in apoptosis is done by flow cytometry after marking with V-APC annexin (allophycocyanin) and propidium iodide. To evaluate the protective action of the monoclonal antibodies, the galectin is preincubated for 30 minutes in the presence of the antibody, the final concentration of which for 24-hour incubation is 10 μg/ml.

Western Blot

The exosomes were lysed (10 minutes on ice) in PY buffer composed of 20 mM tris HCl, 50 mM NaCl, 5 mM EDTA, 1% Triton X 100, 0.02% sodium azide and a cocktail of protease inhibitors (Roche, Basle, Switzerland). After centrifugation (20,000 g, 15 minutes, +4° C.), the cell debris was eliminated and the supernatants collected. The protein concentrations were measured using Bio Rad Protein Assay in accordance with the instructions of the manufacturer (BioRad, Marnes la Coquette, France). The exosomes were then analysed by Western Blot. Briefly, the proteins were separated by an SDS PAGE electrophoresis using gels prepoured in a gradient (gradient 4 12%, Bis Tris, Invitrogen) under standard conditions. The proteins were then transferred onto a nitrocellulose membrane (Hybon dTM-C Extra, Amersham Biosciences, United Kingdom). The latter was blocked for 1 hour at ambient temperature in a blocking buffer containing 0.2% AuroraTN blocking reagent (MP Biomedicals, Mkirch Graffenstaden, France), 0.1% Tween20 (Sigma Aldrich) and PBS (IX), and was then incubated for one night at 4° C. with a primary antibody directed against Galectin-9: Galectin-9-CT-L1 1:100 (supplied by Galpharma, Japan). The membrane was washed with a blocking buffer and then incubated for 1 hour at ambient temperature with a secondary antibody conjugated with peroxidase (anti-mouse, 1:10000) (GE Healthcare, Wauwatosa, United States) and washed once again with the blocking buffer. The specific signals of the proteins were displayed by means of Western Lightning® Plus ECL, a kit amplifying the chemiluminescence of the substrate (PerkinElmer, Boston, Mass., USA), and an LAS3000 luminescent-image analyser (Fujifilm).

FACS Analysis

Immunophenotyping of the cells by flow cytometry was carried out using the "FACSCalibur flow cytometer" apparatus. After having collected them, the cells were washed with "phosphate-buffered saline" (PBS) (GIBCO-Life Technologies) and marked with monoclonal antibodies conjugated with fluorochromes (1:10). For each test, the appropriate control isotypes (monoclonal antibodies) were used for the adjustments of the markers. Finally, the data were analysed with Flow Jo software. In order to detect the surface antigens of the cell, anti-human mouse antibodies were used: CD4-phycoerythrin(PE)-cyanin(Cy)5 (BD Pharmingen, San Diego, United States), -CD25-PE (Miltenyi Biotech, Germany) and -CD127-FITC (1:20) (Clinisciences, Montrouge, France) in accordance with the instructions of the manufacturer.

Real-Time Quantitative PCR

The total RNAs of the regulatory T lymphocytes were isolated using the "RNeasy Minikit II" kit (Qiagen) in accordance with the instructions of the manufacturer. The concentration and purity of the RNAs were measured by the spectrophotometry method (Ultrospec 3000, Pharmacia Biotec). The total RNA was stored at −80° C. until subsequent use.

Inverse transcription of the mRNAs was carried out as follows: 2 μg of the total RNA was mixed with 5 μl of the master mix composed of 1 μl of oligo dT (Roche Diagnostic, Meylan, France) and 0.1 μl RNAsin (40 U/μl, Promega, Charbonnieres, France) and then incubated at 70° C. for 5 to 10 minutes. After 5 minutes at ambient temperature, 10 μl of a second mix was added: 6 μl 5× buffer (Invitrogen)+1 μl 0.1 M DTT (Invitrogen)+2 μl 10 mM dNTPs (Amersham)+0.1 μl RNAsin 40 U/μl (Promega)+1 μl Superscript (Invitrogen). The reaction was followed by a first incubation of 45 to 60 minutes at 45° C., a second incubation of 5 minutes at 95° C. and then a 20-minute treatment with RNase H (Promega). Finally, ultrapure distilled water (GIBCO-Life Technologies) was added in order to obtain a final concentration of 10 ng of total DNA/μl. The DNA was stored at −20° C. until subsequent use.

The transcripts were quantified using real-time PCR (RT-PCR) with the Mx3005P™ sequence detection system (Agilent Technologies, France), in 96-well optical plates (Eurogentec S.A., Belgium). In each well, 10 μl of specific primer pair, designed for RT-PCR and bought from MWG-Biotech (Germany), was disposed at a final concentration of 10 pg/ml, and then stored at −20° C. The β-actin, glyceraldehyde-3-phosphate dehydrogenase (G3PDH), ubiquitin and hypoxanthine guanine phosphoribosyl transferase (HPRT) housekeeping genes were used as controls in each plate. The PCR reactions were carried out in accordance with the instructions of the manufacturer, at a final volume of 20 μl and for 1 μl of cDNA (equivalent to 10 ng of total RNA/μl), using 2×MESA GREEN qPCR MasterMix Plus for SYBR® 258 Assay (Eurogentech) containing Meteor Taq DNA polymerase, $MgCl_2$ (final concentration of 4 mM), dNTPs (including dUTP), SYBR® 260 Green I, stabilisers and passive references required for normalisation of the signal and a buffer with optimised components.

The PCR programme included initial denaturation and activation of the Meteor Taq for 5 minutes at 95° C., followed by 40 standard amplification cycles as follows: 15 seconds at 95° C. (denaturation), 1 minute at 60° C. (synthesis and elongation). The fluorescent products were detected at the last step of each cycle. An analysis of fusion curves was carried out immediately after amplification, in accordance with the instructions of the manufacturer.

The quantitative PCR reactions were used to quantity the expression of the gene of the Galectin-9 by the regulatory T lymphocytes. The β-actin, G3PDH, ubiquitin and hypoxanthine guanine phosphoribosyl transferase (HPRT) housekeeping genes were used as controls. All the primers were designed for RT-PCT and purchased from MWG-Biotech (Germany). Quantitative analysis was carried out on the basis of the cycle threshold (CT) value for each well and calculated using the MxPro software. Each individual value was normalised using the average of the four housekeeping genes in accordance with the standard method of ΔCT: $\Delta CT = C_{T\ housekeeping\ genes}$. For a comparison between the groups, the relative expression of the genes was expressed in $2^{-\Delta\Delta C_T}$ giving an arbitrary value of 1 for the reference sample.

Manufacture of Hybridomes Producing the Monoclonal Antibodies Directed Against Galectin-9, 1G3 and 2E12

A recombinant protein representing the C-terminal portion of human Galectin-9 was used as an immunogen (residues 191 to 355 of the long isoform of Galectin-9). It was produced in E. coli in the form of a GST fusion protein. After separation of the GST label, the protein was purified by exclusion chromatography.

The immunisations were carried out by the company PX Therapeutics (Grenoble, France). Five female BALB-c mice, aged eight weeks, were immunised with the C-terminal portion of the Galectin-9 mentioned above. For the immunisations, 40 micrograms of protein were injected intraperitoneally at day 0, 22, 37 and 54 in association with the complete Freund adjuvant for the first injection, or with the incomplete Freund adjuvant for the following injections. The quality of the immunisation was assessed by an ELISA test, described below, on serum samples coming from the immunised mice. The same preparation of recombinant C-terminal Galectin-9 was used for the immunisations on the one hand and for the ELISA tests on the other hand. These tests showed good immunisation in the five treated mice.

Three days after the last repeat, the two mice that had given the best response were sacrificed and their splenocytes were harvested. These splenocytes were used for the fusion with Sp2/O murine myeloma cells, either in liquid medium or in semi-solid medium, with respective ratios of 5:1 and 2:1. The hybridome supernatants were next evaluated by an ELISA test, carried out as before and as described below, on the recombinant Galectin-9 preparation mentioned above.

The semi-solid fusion was a success and the 39 hybridomes secreting antibodies reacting with the Galectin-9 in ELISA were obtained. Seven of them were selected because of a particularly copious secretion of immunoglobulins and a high degree activity in ELISA. These seven hybridomes were next subjected to new functional screenings in order to study the anti-Galectin-9 neutralising properties of the antibodies produced.

The ELISA test was carried out as follows. The recombinant protein representing the C-terminal portion of the Galectin-9 was adsorbed in the wells of 96-well microtitration plates (50 ng/well) (Greiner Bio-One, Courtaboeuf, France) in the following fashion: dissolving in 0.05 M carbonate/bicarbonate buffer at pH 9.6 and incubation in the wells for 1 hour at ambient temperature. After washing with PBS containing 0.1% Tween-20, the wells were saturated with 3% bovine albumin serum (BSA) in solution in PBS at ambient temperature for 1 hour. They were next incubated with the mice serums or the hybridome supernatants to be tested. Serums and hybridome supernatants were diluted in PBS with 1% BSA and then incubated in the wells at ambient temperature for 2 hours. After a step of washing with 0.1% PBS-Tween-20, the plates were treated by a secondary antibody marked with peroxidise (anti-mouse goat). The final revelation took place after addition of substrate (3,3',5,5'-tetramethylbenzidine or TMB; Thermo Fisher Scientific) and measurement of absorbance at 405 and 620 nm on a Multiskan Ex microplate reader (Thermo Fisher Scientific).

In Vivo Tests on Transgenic Mice

Immunodeficient mice are first of all splenectomised and then xenotransplanted with a C666-1 cell line of modified CNP in order to express the luciferase, which makes it possible to monitor the tumour growth in imaging bioluminescence on the conscious animal. The immune system of the mice is reconstituted and humanised following the injection of human PBMCs more or less enriched with regulatory T lymphocytes (2% regulatory T lymphocytes in the original PBMCs, and addition of 6% to 10% regulatory T lymphocytes in the PBMCs). It has already been shown that PBMCs, to a certain extent, are capable of limiting the growth of the tumour and that the enrichment with regulatory T lymphocytes does not interfere with this effect (Moralès et al, Activation of a Helper and Not Regulatory Human CD4+ T Cell Response by Oncolytic H-1 Parvovirus; PLoS One. 2012; 7 (2): e32197). The anti-Gal-9 1G3 antibody was next injected and its effect on the tumour growth was assessed.

The following experimental protocol was followed:

The SCID mice aged from 6 to 8 weeks undergo a total splenectomy. After 7 days, these same mice are xenotransplanted subcutaneously with cells of a C666-luc tumoral line (expressing luciferase) issuing from a nasopharyngeal carcinoma (NPC). The same day, the mice received, intraperitoneally, 30 to 50 million PBMCs for reconstitution of the immune system, enriched or not with 10% regulatory T lymphocytes, and, according to the animal, 2, 20 or 200 µg of IgG1 antibody or 1G3 antibody subcutaneously in accordance with the following scheme (3 mice/group):

Group 1: IgG1 isotype (not reconstituted)
Group 2: 1G3 (not reconstituted)
Group 3: reconstituted+10% Treg+IgG1 isotype
Group 4: reconstituted (not treated)
Group 5: reconstituted+10% Treg+1G3

All the mice received 3 µg of CPG-ODN2216 (marketed by Miltenyi Biotech) in order to active the immune response.

The monitoring is carried out three times a week for four weeks by means of luminescence readings on the small-animal imaging platform (IVIS® Lumina XRMS, PerkinElmer) and by manual measurements of the tumoral volume and mass. At days 7, 14 and 21 post-transplantation, the mice receive a repeat of CPG-ODN2216 (marketed by Miltenyi Biotech) and, according to the groups presented previously, a repeat of 1G3 or IgG1 antibody. Before the first repeat, a blood sample is taken in order to verify the reconstitution by flow cytometry (cf. protocol page 58). After 28 days of measurement, the mice are sacrificed, the tumours recovered and cryopreserved in expectation of the preparation of immunohistochemistry or immunofluorescence plates and a blood sample is once again taken for analysis by flow cytometry.

The impact of the various concentrations of 1G3 and IgG1 isotype [2, 20 and 200 µg/ml] was evaluated on (i) the weight of the mice, (ii) the tumour volume and (iii) the tumour mass at the time of sacrifice.

(i) Analysis of the Impact of the Injection of the 1G3 Antibody on the Weight of the Mice The incoming mice are regularly weighed [from day 5 to day 28].

(ii) Analysis of the Impact of 1G3 on the Tumour Volume (Manual Measurement)

Several individual experiments were carried out on humanised SCID mice in accordance with the protocol described above and varying the concentration of 1G3 and 1G1 injected. The volume of the tumours was measured manually.

Moreover, in order to obtain a graph representing the impact of 1G3 on the tumour volume, averaged results containing 6 independent in vivo experiments were produced with the 1G3 antibody or the control isotype (20 µg).

The statistical analysis was carried out via a Rank Sum Mann Whitney test (*p<=0.05, **p<=0.001).

The volume of the tumour was also measured by analysis of the bioluminescence emitted by the tumour cells that express the gene of the luciferase, after injection of luciferin. The luminescence is measured via the use of the mouse bioluminescence measuring system (IVIS LUMINA). Six individual experiments were carried out on the humanised SCID mice in accordance with the protocol described above and varying the concentration of 1G3 and 1G1 injected.

Moreover, in order to obtain a graph representing the impact of 1G3 on the tumour volume, average results of 6 independent in vivo experiments were produced with the 1G3 antibody or the control isotype (20 µg).

Finally, tumours of mice treated with 1G3 or the control isotype IgG1 were photographed on millimetric paper in order to measure the size of the tumour at the time of euthanasia.

(iii) Analysis of the Impact of 1G3 on the Mass of the Tumour

The tumours of mice treated with 1G3 or the control isotype IgG1 were weighed after sacrifice. The mass is expressed in grams.

A statistical analysis was carried out by a Rank Sum Mann Whitney test (*p<=0.05, **p<=0.001) (FIG. 22).

Analysis of the Ability of 1G3 to Inhibit the Induction of Regulatory T Lymphocytes by Galectin-9

It has been shown that Galectin-9 is capable of inducing the differentiation of naive CD4 T cells into Treg lymphocytes (Seki, Oomizu et al. 2008), which reinforces the importance of this lectin in the phenomena of exhaustion of the anti-tumoral immune response.

First of all, it was therefore checked whether Galectin-9 can or not transform Tconv cells into Tregs. Tconv cells were cultivated for 3 or 5 days under activation or non-activation conditions, with or without an isoform of Galectin-9 (Gal-9 S or Gal-9 M), with or without 1G3. After these conditioning phases, the cells are recovered, washed and analysed by flow cytometry and co-cultured with PBMCs or autologous Tconv cells. The culture medium was also recovered for ELISA analysis.

The protocol is as follows: the PBMCs were isolated by purification on Ficoll gradient and the conventional T lymphocytes were isolated on magnetic columns in accordance with the protocol of the supplier (Miltenyi Biotech, T Cell Isolation kit). Some of the PBMCs are preserved in non-activation condition and the autologous Tconvs are cultivated for 5 days in activation and non-activation condition. The activation is done by anti-CD3 (1 µg/ml) (supplied by the Anne Tsicopoulos team, CIIL) previously coated on the plates (2H at 37° C.) and anti-CD28 (100 nm/ml) (Clinisciences, France).

These T cells are conditioned or not by the isoforms of Gal-9 S or M at 2 µg/ml, in the presence or not of the 1G3 antibody at 3 µg/ml. After 5 days, the conditioned Tconv are washed, viability is established by counting with Trypan blue* (cf. below), the supernatant is recovered with a view to ELISA tests and $10^5$ cells are analysed by flow cytometry in order to measure the expression the CD4, CD25 and CD127 markers. The rest of the conventional cells are put in contact with the autologous PBMCs that had been preserved for the MLR test.

The suppression tests are carried out by MLR (mixed lymphocyte reaction) by putting in co-culture $10^5$ conditioned Tconv with $10^5$ autologous PBMCs (ratio 1:1), in the presence or not of the 1G3 or 2E12 antibody. The cells are activated with 1 µg/ml of anti-CD3, previously coated on the plates (2H at 37° C.) and anti-CD28 (100 ng/ml).

After 3 days of co-culture, proliferation is evaluated by incorporation of 1 µCi/well of tritiated thymidine ($^3$H Th) (GE Healthcare, France), 18 hours before the end of the culture. After 3 days, the plates are filtered on glass-fibre filters (PerkinElmer, France). The filter is incubated in a scintillation liquid (Beckman Instruments Inc, Ready Safe, USA) and read with a scintillation counter (1450 Trilux, Wallac, Finland). The results are finally expressed in counts per minute (cpm). The statistical analysis carried out by a Rank Sum Mann Whitney test (*p<=0.05, **p<=0.001).

Counting with Trypan Blue

The vital azo dye (Trypan blue) for colouring dead cells. The counting is evaluated by incorporation of 1 volume of 0.4% Trypan blue solution (Sigma, USA) for one volume of cell suspension. After 3 minutes, the mixture is deposited on a Thomas plate. The dead cells that appear in blue and the refringent living cells are counted. The measurements are carried out in triplicate and the results expressed as a percentage of living cells.

Measurement of the Secretion of Galectin-9 by ELISA

50 µl of a 0.2 µg/ml solution of anti-Gal-9 antibody (clone: SEA309Hu-Uscn Life Science Inc, USA) is fixed in 96-well plates (NUNC, Denmark) for 1 night at 4° C. After 4 washings with IX PBS (Euromedex, France)—Tween (Sigma Aldrich, USA) 0.05%, the plates are saturated with 3% PBS-BSA (Sigma Aldrich®, USA) for 2 hours at ambient temperature. They are then washed 3 times with 0.05% PBS-Tween. 100 µl/well of culture supernatant of the Treg lymphocytes, activated or not, are deposited in duplicate, and incubated for 2 hours at ambient temperature. The Treg lymphocytes are conventionally activated by anti-CD3 (1 µg/ml) (supplied by the Anne Tsicopoulos team, CIIL) previously coated on the plates (2 hours at 37° C.) and anti-CD28 (100 ng/ml (Cliniscienes, France).

On each plate, a range of recombinant Galectin-9 (Uscn Life Science Inc, USA) with a concentration of 2.5 ng/ml at 2.5 pg/ml, in 1% PBS-BSA, is done.

After 3 washings with PBS-Tween, 100 µl/well of biotinylated secondary antibody, at 1 µg/ml, is incubated for 1 hour at ambient temperature. The plate is once again washed 3 times and the reaction is amplified by the addition of 100 µl/well of streptavidin-peroxidase at 1/10000, for 30 minutes at ambient temperature. After 4 washings, the plates are revealed by 100 µl/well of revealing solution with OPD (O-phenylenediamine dihydrochloride) (Sigma-Aldrich®, USA) at 1 mg/ml for 10 minutes in darkness. This reaction is stopped by the addition of 50 µl/well of 2N HCl (VWR, USA).

The plates are next read with a spectrophotometer, at a wavelength of 492 nm (Multiskan Ex, ThermoLabsystems, France).

Measurement of the Viability of the PBMCs

The viability tests were carried out directly by the Cell-Titer-Glo method, which makes it possible to measure mitochondrial metabolism. The same protocol is used for evaluating the viability of the Tconv lymphocytes.

$2.10^5$ of autologous PBMCs are deposited in co-culture. The cells are activated [activation by anti-CD3 (1 µg/ml) (supplied by the Anne Tsicopoulos team, CIIL) previously coated on the plates (2 hours at 37° C.) and anti-CD28 (100 ng/ml) (Cliniscienes, France)] or not depending on the conditions and are incubated with the 1G3 antibody or the control isotype 1G1 at a concentration of 3, 6 or 12 µg/ml. The culture is done in flat-bottomed 96-well plates with opaque "walls" (Corning 3610, Corning Incorporated, USA) in 100 µl of culture medium (DMEM+4.5 g/l glucose +L-glutamine, 100 U/mM of penicillin, 100 µg/ml of streptomycin, 10% decomplemented human AB serum) (Gibco-BRL™, Life Technologies, GB).

The test uses the Promega CellTiter-Glo Luminescent Cell Viability Assay kit (Promega Corporation, USA), which uses the activity of luciferase, in the presence of oxygen, to measure cell metabolism (ATP) as an indicator of cell viability. After 48 hours of culture, 100 µl of reagent (luciferin, luciferase and buffer containing magnesium) are added in each well; agitation of the plate for 2 minutes then incubation for 15 minutes, at ambient temperature, away from light. The tests are carried out in triplicate and the plates are read with a luminometer (Centra LB960, C Berthold Technologies, France). Reading 1 second/well.

Membrane Markings of the Tconv Lymphocytes by Flow Cytometry (Facs)

Antibodies Used (Ac)

Anti-human monoclonal primary antibodies coupled with fluorochromes, anti-CD4-PE (phycoerythrin) -C (cyanine) 5 (BD Pharmingen™, USA), anti-CD25-PE (Miltenyi Biotech, France), anti-CD127-FITC (fluorescein isothiocyanate) (Cliniscienes, France).

For compensation, the control isotype of the various monoclonal antibodies was used.

Direct Marking Protocol

The cells ($2.10^5$) are taken up in a volume of 100 µl of sterile PBS (GIBCO BRL™, Invitrogen®, GB) and incubated for 30 minutes at ambient temperature and in darkness with 10 µl of anti-CD4-PC, 10 µl of anti-CD25-PE and 4 µl of anti-CD127-FITC. The marked cells are next taken up with 400 µl of PBS and the fluorescence is analysed by flow cytometry by Facscalibur (FACS Flow Supply System, Becton Dickinson, USA).

The cytometry results are analysed by the Flow Jo software (Tree Star Incorporation, USA). For some experiments, after the addition of the marked antibodies, the cells are fixed by the addition of 100 µl of 4% FBA (Sigma-Aldrich, USA) for 10 minutes and are then taken up in 200 µl of PBS before analysis by cytometer.

Proliferation and Suppression (MLR) (2E12)

Proliferation Check

The proliferation tests are carried out on $10^5$ PBMCs cultivated for 48 hours. The cells are cultivated in 96 round-bottomed plates (Nunc, Denmark) in 200 µl of culture medium (RPMI-1640, 1% 2 mM L-glutamine, 0.02 mMde sodium pyruvate, 100 U/mM of penicillin, 100 µg/ml of streptomycin, 10% decomplemented human AB serum) (GibcoBRL™, Invitrogen, GB). They are activated by anti-CD3 (1 µg/ml) (supplied by the Ann Tsicopoulos team, CIIL) previously coated on the plates (2 hours at 37° C.) and anti-CD28 (100 ng/ml) (Cliniscienes, France) in the presence or not of 1G3 or 2E12 antibodies.

Suppression

The suppression tests are carried out by MLR (mixed lymphocytes reaction) by putting $6.10^4$ Treg in co-culture with $10^5$ autologous PBMCs, in the presence or not of 1G3 or 2E12 antibodies. The cells are activated with 1 µg/ml of anti-CD3, previously coated on the plates (2 hours at 37° C.) and anti-CD28 (100 ng/ml).

The proliferation is evaluated by incorporating 1 uCi/well of tritiated thymidine ($^3$H Th) (GE Healthcare, France), 18 hours before the end of the culture. After 48 hours, the plates are filtered on glass-fibre filters (PerkinElmer, France). The filter is incubated in a scintillation liquid (Beckman Instruments Inc, Ready Safe, USA) and read with a scintillation counter (1450 Trilux, Wallac, Finland). Finally, the results are expressed in counts per minute (cpm).

RESULTS

Phenotype Analysis of the PBMCs and the Regulatory T Lymphocytes

Analysis in flow cytometry (FACS) of the PBMCs shows that the regulatory T lymphocytes CD4+CD25+CD127− represent 1% of the total PBMCs (results not shown).

Moreover, FACS analysis of the phenotype markers of the autologous regulatory T lymphocytes isolated ex vivo indicates that 95% of the regulatory T lymphocytes are CD4+ CD25+ and that, among these cells, 90% are CD127− or CD127 low and more than 86% FoxP3+ (FIG. 1).

The Activated Regulatory T Lymphocytes have a Suppressor Activity

The suppressor activity of the human regulatory T lymphocytes, isolated ex vivo from healthy donor blood, was characterised by two complementary functional analyses: a test of suppression of the proliferation of the PBMCs activated by the autologous regulatory T lymphocytes and a test of cytolysis of the PBMCs activated by the autologous regulatory T lymphocytes (FIG. 2).

FIG. 2A shows that the activated PBMCs alone proliferate well in vitro while the regulatory T lymphocytes isolated ex vivo are anergic, even after activation thereof. However, the proliferation of the activated PBMCs decreases by more than 24% in the presence of activated autologous regulatory T lymphocytes with a ratio of 4:2 (cf. FIG. 2A). The proliferation test (MLR) therefore clearly shows that the regulatory T lymphocytes isolated ex vivo and in an activation condition have an immunosuppressor activity.

The results obtained by the proliferation test are reinforced by the results of the cytolysis test. It is in fact shown in FIG. 2B that the lower the PBMC:regulatory T lymphocytes ratio, the higher the percentage of lysis of the activated PBMCs. The regulatory T lymphocytes therefore induce lysis of the autologous PBMCs, at different ratios and in a dose-dependent fashion.

Galectin-9 is Present On, and Expressed By, the Regulatory T Lymphocytes

Analyses by real-time quantitative PCR (FIG. 3) and by Western Blot (FIG. 4) show that Galectin-9 is present on the human regulatory T lymphocytes isolated ex vivo and that the latter express Galectin-9, suggesting that regulatory T lymphocytes use the Galectin-9 channel to inhibit the proliferation of the effector T lymphocytes.

The expression of Galectin-9 by the Effector T Lymphocytes Decreases on Activation; the Expression of Galectin-9 by the Regulator T Lymphocytes Increases on Activation FIG. 14 shows that, whereas the Tconv lymphocytes and the non-activated regulatory T lymphocytes produce very small quantities of Galectin-9 (<10 pg/ml: that is to say below the detection threshold of an ELISA test), activated human regulatory T lymphocytes are capable of synthesising and secreting Galectin-9 in the extracellular environment. Moreover, this secretion of Galectin-9 is significantly greater when the regulatory T lymphocytes are activated, linking this secretion to their suppressive function.

FIG. 5 shows that the ratio between conventional CD4+ T lymphocytes and 5 regulatory T lymphocytes considerably decreases during activation.

The activated conventional CD4+ T lymphocytes express the gene coding Galectin-9 only a little and this expression significantly decreases during activation thereof.

On the other hand, expression of the gene coding Galectin-9 by regulatory T lymphocytes increases during activation thereof (cf. FIGS. 5 and 6).

Thus the constitutively activated effect of T lymphocytes, having an anti-tumoral action, will not be the target of the anti-Gal-9 antibody. On the other hand, the regulatory T lymphocytes that are activated and therefore functional will be a favoured target of the anti-Gal-9 antibody.

Analysis of the differential protein expression of Galectin-9 in the regulatory T lymphocytes and the CD4+ T cells was reinforced by flow cytometry. As can be seen in FIG. 10, the basal expression is low and almost identical between the regulatory T lymphocytes and the freshly isolated CD4+ T cells. Nevertheless, it is found that, after activation of the TCR (anti-CD3/anti-CD28), the expression profile changes with the appearance of a population in the regulatory T lymphocytes that very strongly expresses Galectin-9. This overexpression persists and increases proportionally to time whereas the basal expression of Galectin-9 remains low in the CD4+ Tconv cells, even after activation (FIG. 10).

It is thus demonstrated that the overexpression of Galectin-9 is specific to the activated regulatory T lymphocytes and that there is a very low expression of Galectin-9 in the CD4+ Tconv cells under basal conditions and after activation. The risk of targeting the effector CD4+ T lymphocytes is thus eliminated, which enables the patient being cared for according to the invention to maintain his immune defences.

The Suppressor Activity of Regulatory T Lymphocytes is Inhibited by the Anti-Galectin-9 1G3 Antibody To evaluate in vitro the impact of the 1G3 antibody on the activity of the regulatory T lymphocytes, a cell proliferation test based on the incorporation of tritiated thymidine was used.

FIG. 7 presents the results of the test on proliferation of the PBMCs in the presence of irradiated C15s in the presence or not of regulatory T lymphocytes and in the presence or not of 1G3 antibodies at a concentration of 1 μg/ml.

Firstly, it is confirmed by the positive controls of the test that the activation of the PBMCs does indeed give rise to an increase in their proliferation and that the presence of the regulatory T lymphocytes does indeed give rise to a reduction in the cell proliferation of the PBMCs.

It is also shown that the irradiation of the C15 tumoral cells does indeed cause a stoppage of their proliferation. The C15 cells are anergic.

The presence of C15 tumoral cells does indeed give rise to a reduction in the cell proliferation of human PBMCs.

It is next shown that the presence of the regulatory T lymphocytes in the co-culture of PBMCs and C15 causes a significant additional reduction in the proliferation, by approximately 56%.

FIG. 7 shows clearly that, unexpectedly, the presence of a 1G3 antibody makes it possible to restore the proliferation of the PBMCs. It is thus suggested that the 1G3 antibody neutralises the Galectin-9 present on, and expressed by, the regulatory T lymphocytes. Consequently it is shown that the 1G3 antibody inhibits the suppressor activity of the regulatory T lymphocytes.

The 1G3 Anti-Galectin-9 Antibody has an Efficacy Superior to Other Anti-Galectin-9 Antibodies To compare the effect of the 1G3 antibody with other anti-Galectin-9 antibodies, or even with an anti-TIM3 antibody, on the inhibition of the suppressor activity of the regulatory T lymphocytes, several tests were carried out.

Thus the effect of various anti-Galectin-9 antibodies on the inhibition of the apoptosis caused by Galectin-9, and the anti-Galectin-9 antibody effect on the restoration of the proliferation after treatment of human PBMCs with Galectin-9, were analysed. The anti-Galectin-9 antibodies tested in comparison with 1G3 do not recognise the same epitope of Galectin-9 as the 1G3 antibody.

An anti-TIM3 antibody was also tested. This is because certain theories have been raised concerning a link between the Tim-3 receptor, which would be present on the T lymphocytes, and the pro-apoptic effect of Galectin-9.

Inhibition of the Apoptosis Caused by Galectin-9

FIG. 8 presents the results of the test on the effect of the antibodies tested on the apoptosis of the Jurkats caused by recombinant Galectin-9.

The antibodies tested are the 9M1 (anti-Galectin-9), 9S2-3 (anti-Galectin-9) and 1G3 (anti-Galectin-9) antibodies, and an anti-TIM3, 2E12 (anti-Galectin-9) antibody.

As can be seen in FIG. 8, protection against the apoptosis of the Jurkats is better with the 1G3 antibody than with the other anti-Galectin-9 antibodies 9S2-3 and 9M1 or the anti-TIM3 antibody.

Restoration of Proliferation After Treatment with Galectin-9

FIG. 9 presents the results of the test on the effect of the antibodies tested on the proliferation of human PBMCs previously treated with Galectin-9.

The antibodies tested are the ECA-42 (anti-Galectin-9), 1G3 (anti-Galectin-9), 2E2 (anti-TIM3) and 2E12 (anti-Galectin-9) antibodies.

As can be seen in FIG. 9, the proliferation of the human PBMCs is restored more effectively with the 1G3 antibody than with the other anti-Galectin-9 antibodies ECA-42 and 2E12 or the anti-TIM3 antibody (2E2).

Effect on Tconv Lymphocytes (T CD4+)

FIG. 11 presents the results of the tests on the effect of Galectin-9 and 1G3 on Tconv lymphocytes (T CD4+) by measuring the proliferation on freshly isolated cells, via the incorporation of tritiated thymidine during the last 18 hours of culture. The results are also given in counts per minute (cpm).

Just like the PBMCs (FIG. 9), the Tconv lymphocytes isolated ex vivo proliferate under activation conditions. It is also shown that Galectin-9 significantly inhibits the proliferation of Tconv lymphocytes, in the same way as PBMCs.

Finally, it should be noted in this FIG. 11 that the anti-Galectin-9 (1G3) antibody does not have any effect on the proliferation of Tconv lymphocytes.

Analysis of the Cytotoxic Effect and its Control Isotype on the Proliferation of PBMCs The effect of increasing doses of 1G3 antibodies or of its control isotype (IgG1) was analysed on PBMCs by measuring the proliferation on freshly isolated cells extracted from the blood of 3 donors by incorporation of tritiated thymidine during the last 18 hours of culture. The results were obtained in CPM.

It is observed in FIG. 12 that the PBMCs isolated ex vivo proliferate in vitro under activation conditions. It is moveover to be noted that the 1G3 antibody and its control isotype IgG1 do not affect the proliferation of PBMCs, even with high doses of monoclonal antibody (from 3 to 12 µg/ml).

Analysis of the Cytotoxic Effect of the 1G3 Antibody and its Control Isotype on the Viability of PBMCs Increasing the dose of mAb 1G3 and of its control isotype (1G1) was analysed by measuring the viability of PBMCs freshly isolated from 3 donors by luminometric analysis. The mitochrondrial metabolism was measured for 5 days of activation. The results were obtained in RLU.

FIG. 13 shows that the PBMCs isolated ex vivo maintain and increase their viability in vitro under activation conditions. This also demonstrates that 1G3 and the 1G1 isotype do not modify the viability of the PBMCs, even at a high dose of antibody (from 3 to 12 µg/ml).

It has thus been demonstrated that the 1G3 antibody affects neither the proliferation nor the viability of the PBMCs and human T CD4+. Thus the risk of secondary effect, such as the induction of an immunosuppression that would be favourable to tumoral progression, is reduced. This allows better maintenance of the immune defences, in particular anti-tumoral, in the patient being cared for according to the invention.

Analysis of the Neutralising Effect of 1G3 on the Suppressor Activity of Regulatory T Lymphocytes The potential for inhibition of the function of the regulatory T lymphocytes by the 1G3 antibody was analysed by tests on proliferation of a mixed leucocyte reaction of regulatory T lymphocytes and conventional T lymphocytes.

As expected, the results demonstrated that regulatory T lymphocytes inhibit the proliferation of the cells in co-culture (FIG. 15). In addition, a preculture of 2 hours with 1G3 sufficed to reverse this inhibiting effect. Use of the control isotype of 1G3, which has no effect on Treg lymphocytes, makes it possible to conclude that this reversal of the inhibition caused by the regulatory T lymphocytes is specific and passes via Galectin-9.

In order to determine whether 1G3 inhibits regulatory T lymphocytes by acting on the soluble Galectin-9 or directly on the regulatory T lymphocytes, a test was carried out with an inhibitor blocking soluble Galectin-9, and compared with the results obtained with the 1G3 antibody.

The results show clearly that the chemical inhibiter had no significant effect on the suppressor activity of the regulatory T lymphocytes. Use with the 1G3 antibody once again caused a reversal of the suppression induced by the regulatory T lymphocytes. These results thus confirm that Galectin-9 acts in the suppression induced by the regulatory T lymphocytes and that 1G3 is capable of reversing this inhibition.

In Vivo Neutralisation of the Suppressor Activity of Regulatory T Lymphocytes

The impact of various concentrations of 1G3 and of IgG1 isotype [2, 20 and 200 µg/ml] was evaluated on (i) the weight of the mice, (ii) the tumour volume and (iii) the tumour mass on sacrifice.

(i) Analysis of the Impact of the Injection of the 1G3 Antibody on the Weight of the Mice As can be seen in FIGS. 18 A and B, the mice treated with 1G3 are lighter compared with those treated by the control isotype. These results suggest that the reduction in weight of the treated mouse may be related to the reduction of the tumour.

(ii) Analysis of the Impact of 1G3 on the Tumour Volume (Manual Measurement)

The results obtained shown in FIG. 19 A-D indicate a positive effect of 1G3, which causes a significant limitation of the tumour growth compared with the control isotype.

Moreover, the results presented in FIG. 20 clearly indicate a significant difference between immunisation by 1G3 and its control isotype, the tumour growth through 1G3 being largely limited.

These results are also confirmed by the bioluminescence measurements (FIG. 21 A-D, FIG. 22), 1G3 inducing a limitation to the tumour growth compared with its control isotype.

Finally, the photographs of the tumours (not shown), also show the positive effect of 1G3, causing a limitation to the tumour growth compared with its control isotype.

(iii) Analysis of the Impact of 1G3 on the Size of the Tumour

The results concerning the mass of the tumour (FIG. 23) in their turn confirm the beneficial effect of 1G3 compared with its control isotype.

Analysis of the Ability of 1G3 to Inhibit the Induction of Regulatory T Lymphocytes by Galectin-9

It has been shown that Galectin-9 is capable of inducing differentiation of naive CD4 T lymphocytes into Treg lymphocytes (Seki et al, Galectin-9 suppresses the generation of Th17, promotes the induction of regulatory T cells, and regulates experimental autoimmune arthritis; Clin Immunol. 2008 April; 127(1):78-88. doi:10.1016/j.clim.2008.01.006. Epub February 20), which reinforces the importance of this lectin in the phenomena of exhaustion of the anti-tumoral immune response.

The results presented in FIG. 25 clearly indicate that the CD4+ Tconv lymphocytes conditioned with each isoform of Galectin-9 acquire a suppressive phenotype and inhibit the proliferation of PBMCs. This inhibition is stronger with the S (short) form of Galectin-9 then with the M (medium) form. It has also been found that adding 1G3 during conditioning inhibits the establishment of this suppressor phenotype and restores proliferation significantly by neutralising Galectin-9.

Moreover, as shown in FIG. 24, the FACS analyses of the cells at the end of the test indicate that each isoform of Galectin-9 causes an increase in the expression of CD25. However, as shown by FIG. 24, the activated cells overexpress CD25 in normal times.

The results clearly indicate that adding Galectin-9 to the Tconv lymphocytes (i) causes a slight increase in the expression of CD4 with the S form or the M form of a Galectin-9, compared with the activated Tconv lymphocytes; (ii) has no effect on the expression of CD127 except during the conditioning phase with the M or S form of Galectin-9; (iii) causes a significant increase in the expression of CD25 with the M form and the S form of Galectin-9 compared with the activated Tconv lymphocytes.

FIG. 24 therefore indicates that the pre-incubation of the Tconv lymphocytes with the M or S form of Galectin-9 increases the expression of the CD4 and CD25 markers on account of a possibly more suppressing phenotype. Nevertheless, this hypothesis is acceptable only if it is correlated with a suppressor activity of these conditioned Tconv lymphocytes, making it possible to validate the suppressor phenotype, which is the case (cf. FIG. 25).

To conclude, it is shown that Galectin-9 causes a conversion of the conventional CD4+ T lymphocytes into immune suppressor CD4+ T lymphocytes. The 1G3 antibody is capable of neutralising the induction of this conversion and thus promoting the maintenance of an anti-tumoral immune response in the patient being cared for according to the invention.

Analysis of the Neutralising Effect of 2E12 on the Suppressor Activity of Treg Lymphocytes The potential for inhibition of the suppressor function of regulatory T lymphocytes by the 2E12 antibody was analysed by tests on proliferation of a mixed leucocyte reaction of regulatory T lymphocytes with autologous PBMCs (2 independent donors).

The results, which can be seen in FIG. 26, show that a preculture of 2 hours of regulatory T lymphocytes with 2E12 sufficed to reverse the inhibiting of the proliferation of the cells by the regulator T lymphocytes. The use of this control isotype of 2E12, which has no effect on the regulatory T lymphocytes, enables us once again to conclude that this reversal of the induced inhibition of regulatory T lymphocytes is specific and passes via Galectin-9.

Moreover, it is observed that the 2E12 antibody, just like 1G3, is capable of reversing this inhibition. The efficacy of 2E12 is substantially less high than 1G3 however, in that a slight reduction in the proliferation of PBMCs is observed, unlike 1G3.

REFERENCES (1) Grossman W J, Verbsky J W, Barchet W, Colonna M, Atkinson J P. Ley T J. "Human T regulatory cells can use the perforin pathway to cause autologous target cell death". Immunity. 2004 October; 21(4):589-601.
(2) Garin M I, Chu C C, Golshayan d, Cernuda-Moróllon E, Wait R, Lechler R I. "Galectin-1: a key effector of regulation mediated by CD4+CD25+ T cells". Blood. 2007 Mar. 1; 109(5):2058-65
(3) Johnson B D, Jing W, Orentas R J, "CD25+ regulatory T cell inhibition enhances vaccine-induced immunity to neuroblastoma". J Immunother, 2007 February-March; 30(2):203-14.
(4) McHugh R S, Whitters M J, Piccirillo C A, Young D A, Shevach E M, Collins M, Byrne M C, "CD4(+)CD25(+) immunoregulatory T cells: gene expression analysis reveals a functional role for the glucocorticoid-induced TNF receptor". Immunity. 2002 February; 16(2):311-23.
(5) Wing K, Onishi Y, Prieto-Martin P, Yamaguchi T, Miyara M, Fehervari Z, Nomura T, Sakaguchi S, "CTLA-4 control over Foxp3+ regulatory T cell function". Science. 2008 Oct. 10; 322(5899):271-5. (5) Zahran A M et al, Int J Clin Oncol. 2013 Sep. 26.
(6) Fisson S I, Darasse-Jèze G, Litvinova E, Septier F, Klatzmann D. Liblau R, Salomon B L. Continuous activation of autoreactive CD4+ CD25+ regulatory T cells in the steady state. J Exp. Med. 2003 Sep. 1; 198(5): 737-46. Epub 2003 Aug. 25.
(7) Xu W et al. J Cancer Res Clin Oncol. 2013 November; 139(11); 1845-52
(8) Ladanyi A, Magy Onkol. 2013 June; 57(2):85-95
(9) Zhang W et al, Gynecol Oncol. 2014 Jan. 2. pii: S0090-8258(13)01427-3.
(10) Faghih Z et al, Immunol Lett. 2013 Dec. 8:158(1-2): 57-65
(11) Aida K et al, Cancer Sci. 2013 Nov. 30
(12) Huang X M et al, Cancer Sci. 2013 November
(13) Preston C C et al, PLoS One. 2013 Nov. 14; 8(11): e80063
(14) He M et al, Neuro Oncol. 2013 June; 15(6):727-34
(15) Muthu Raja K R et al, PLoS One. 2012; 7(10:e47077
(16) Davidson S et al, Mod Pathol. 2013 March; 26(3):448-55
(17) Huang Y et al, Digestion 2012; 86(4):329-37
(18) Memarian A. Tumour Biol. 2013 February; 34(1):531-42
(19) Delhem et al, Expert Opin Biol Ther. 2010:10(11): 1563-1572
(20) Ouaguia et al, ISRN Hepatology, Volume 2013 (2013), Article ID 928485
(21) Carpentier et al, Am J Transplant. 2009:9(9): 2192-2112.
(22) Moralès et al, BRMI, Volume 2014 (2014), Article ID 290878
(23) Baumforth et al, Am J Pathol. 2008 July; 173(1):195-204
(24) Moralès et al, PlosOne, In press 2014
(25) Krausz L T et al, Ideggyogy Sz. 2013 Sep. 30; 66(9-10):343-8.

The invention claimed is:

1. A method of treating nasopharyngeal carcinoma in a human patient in need thereof comprising administering to the human patient an amount of an antibody directed against Galectin-9 effective to inhibit the suppressor activity of human regulatory T lymphocytes, thereby reducing tumor growth in the human patient, wherein the antibody has as CDRs
   the six CDRs defined by:
   the amino acid sequence SEQ ID NO:2 in the region H-CDR1;
   the amino acid sequence SEQ ID NO:3 in the region H-CDR2;
   the amino acid sequence SEQ ID NO:4 in the region H-CDR3;
   the amino acid sequence SEQ ID NO:6 in the region L-CDR1;
   the amino acid sequence SEQ ID NO:7 in the region L-CDR2; and
   the amino acid sequence SEQ ID NO:8 in the region L-CDR3.

2. The method according to claim 1, wherein the carcinoma is associated with Epstein-Barr virus.

3. The method according to claim 1, wherein the antibody binds specifically to an epitope of an amino acid sequence SEQ ID NO:9.

4. The method according to claim 1, wherein the variable heavy-chain region of said antibody has the amino acid sequence SEQ ID NO:1 and the variable light-chain region of said antibody has the amino acid sequence SEQ ID NO:5.

5. The method according to claim 1, wherein the antibody is included in a pharmaceutical composition comprising a therapeutically effective amount of the antibody and at least one pharmaceutically acceptable carrier.

6. The method according to claim 1, wherein the antibody is combined with an anticancer agent and wherein the administration to the human patient in need thereof is simultaneous, separate or spread over time in the treatment of the nasopharynegeal carcinoma.

7. The method according to claim 1, wherein the administration of the antibody inhibits the suppressor activity of regulatory T lymphocytes in the nasopharyngeal carcinoma of the human patient.

* * * * *

SEQUENCE LISTING

<160> NUMBER OF SEQ ID NOS: 17

<210> SEQ ID NO 1
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fragment of antibody

<400> SEQUENCE: 1

Met Lys Cys Ser Trp Gly Ile Phe Phe Leu Leu Ser Val Thr Ala Gly
1               5                   10                  15

Val His Ser Lys Val Gln Leu Gln Gln Ser Gly Ala Glu Leu Val Lys
            20                  25                  30

Pro Gly Ala Ser Val Lys Leu Ser Cys Lys Ala Ser Gly Tyr Thr Phe
        35                  40                  45

Thr Asp Tyr Thr Ile His Trp Val Lys Gln Arg Ser Gly Gln Gly Leu
    50                  55                  60

Glu Trp Ile Gly Trp Phe Tyr Pro Gly Ser His Ser Ile Lys Tyr Asn
65                  70                  75                  80

Glu Gln Phe Lys Asp Arg Ala Thr Leu Thr Ala Asp Lys Ser Ser Ser
                85                  90                  95

Thr Val Tyr Met Glu Leu Ser Arg Leu Thr Ser Glu Asp Ser Ala Val
            100                 105                 110

Tyr Phe Cys Thr Arg His Gly Gly Tyr Asp Gly Phe Asp Tyr Trp Gly
        115                 120                 125

Gln Gly Thr Thr Leu Thr Val Ser Ser Ala Lys Thr Thr Pro Pro Ser
    130                 135                 140

Val Tyr Pro Leu
145

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Fragment of antibody

<400> SEQUENCE: 2

Gly Tyr Thr Phe Thr Asp Tyr Thr Ile His
1               5                   10

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Fragment of antibody

<400> SEQUENCE: 3

Trp Phe Tyr Pro Gly Ser His Ser Ile Lys Tyr Asn Glu Gln Phe Lys
1               5                   10                  15

Asp Arg

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Fragment of antibody

<400> SEQUENCE: 4

His Gly Gly Tyr Asp Gly Phe Asp Tyr
1               5

<210> SEQ ID NO 5
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fragment of antibody

<400> SEQUENCE: 5

Leu Asp Gly Gly Lys Met Asp Ser Gln Ala Gln Val Leu Met Leu Leu
1               5                   10                  15

Leu Leu Trp Val Ser Gly Thr Cys Gly Asp Ile Val Met Ser Gln Ser
            20                  25                  30

Pro Ser Ser Leu Ala Val Ser Val Gly Glu Lys Ile Thr Met Ser Cys
        35                  40                  45

Lys Ser Ser Gln Ser Leu Phe Tyr Ser Thr Asn Gln Lys Asn Tyr Leu
    50                  55                  60

Ala Trp Tyr Gln Gln Lys Pro Gly Gln Ser Pro Lys Leu Leu Ile Tyr
65                  70                  75                  80

Trp Ala Ser Thr Arg Glu Ser Gly Val Pro Asp Arg Phe Thr Gly Ser
                85                  90                  95

Gly Ser Gly Thr Asp Phe Thr Leu Thr Ile Ser Ser Val Lys Ala Glu
            100                 105                 110

Asp Leu Ala Val Tyr Tyr Cys Gln Gln Tyr Tyr Tyr Phe Pro Tyr Thr
        115                 120                 125

Phe Gly Gly Gly Thr Lys Leu Glu Ile Lys Arg Ala Asp Ala Ala Pro
    130                 135                 140

Thr Val Ser Ile Phe Pro Pro Ser Ser
145                 150

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Fragment of antibody

<400> SEQUENCE: 6

Lys Ser Ser Gln Ser Leu Phe Tyr Ser Thr Asn Gln Lys Asn Tyr Leu
1               5                   10                  15

Ala

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Fragment of antibody

<400> SEQUENCE: 7

Trp Ala Ser Thr Arg Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Antibody

<400> SEQUENCE: 8

Gln Gln Tyr Tyr Tyr Phe Pro Tyr Thr
1               5

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Fragment of galectin 9

<400> SEQUENCE: 9

Thr Pro Ala Ile Pro Pro Met Met Tyr Pro His Pro Ala
1               5                   10

<210> SEQ ID NO 10
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH 2E12

<400> SEQUENCE: 10

Met Gly Trp Ser Phe Ile Ile Leu Leu Ser Val Thr Ala Gly Val His
1               5                   10                  15

Ser Lys Val Gln Leu Gln Gln Ser Gly Ala Glu Leu Val Lys Pro Gly
            20                  25                  30

Ala Ser Val Lys Leu Ser Cys Lys Ala Ser Gly Tyr Thr Phe Thr Glu
        35                  40                  45

Tyr Thr Ile His Trp Val Lys Gln Arg Ser Gly Gln Gly Leu Glu Trp
    50                  55                  60

Ile Gly Trp Phe Tyr Pro Gly Ser Gly Ser Met Glu Tyr Asn Glu Lys
65                  70                  75                  80

Phe Asp Lys Ala Thr Leu Thr Ala Asp Asn Ser Ser Thr Val Tyr
            85                  90                  95

Met Glu Leu Ser Arg Leu Thr Ser Glu Asp Ser Ala Val Tyr Phe Cys
        100                 105                 110

Glu Arg His Gly Gly Tyr Asp Gly Phe Asp Tyr Trp Gly Gln Gly Thr
        115                 120                 125

Thr Leu Thr Val Ser Ser Ala Lys Thr Thr Pro Pro Ser Val Tyr Pro
    130                 135                 140

Leu Ile Phe Leu Glu Asp Leu Leu Gln Tyr Ser Gln Leu Pro Trp Lys
145                 150                 155                 160

Ile Asp Val Leu Leu Leu Phe Ser Gln Asp Phe Gln Ala Val Tyr
                165                 170                 175

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: H-CDR1 2E12

<400> SEQUENCE: 11

Gly Tyr Thr Phe Thr Glu Tyr Thr Ile His
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: H-CDR2 2E12

<400> SEQUENCE: 12

Trp Phe Tyr Pro Gly Ser Gly Ser Met Glu Tyr Asn Glu Lys Phe Asp
1               5                   10                  15

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: H-CDR3 2E12

<400> SEQUENCE: 13

His Gly Gly Tyr Asp Gly Phe Asp Tyr
1               5

<210> SEQ ID NO 14
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL 2E12

<400> SEQUENCE: 14

```
Leu Asp Gly Gly Lys Met Asp Ser Gln Ala Gln Val Leu Met Leu Leu
 1               5                  10                  15

Leu Leu Trp Val Ser Gly Thr Cys Gly Asp Ile Val Met Ser Gln Ser
             20                  25                  30

Pro Ser Ser Leu Ala Val Ser Val Gly Glu Lys Val Thr Met Ser Cys
             35                  40                  45

Lys Ser Ser Gln Ser Leu Leu Tyr Ser Asn Asn Gln Lys Asn Tyr Leu
 50                  55                  60

Ala Trp Tyr Gln Gln Lys Pro Gly Gln Ser Pro Lys Leu Leu Ile Tyr
 65                  70                  75                  80

Trp Ala Ser Thr Arg Gly Ser Gly Val Pro Asp Arg Phe Thr Gly Ser
                 85                  90                  95

Gly Ser Gly Thr Asp Phe Thr Leu Thr Ile Ser Ser Val Lys Ala Glu
                100                 105                 110

Asp Leu Ala Ile Tyr Tyr Cys Gln Gln Tyr Tyr Ser Tyr Pro Phe Thr
                115                 120                 125

Phe Gly Gly Gly Thr Lys Leu Glu Ile Lys Arg Ala Asp Ala Ala Pro
    130                 135                 140

Thr Val Ser Ile Phe Pro Pro Ser Ser
145                 150

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: L-CDR1 2E12

<400> SEQUENCE: 15

Lys Ser Ser Gln Ser Leu Leu Tyr Ser Asn Asn Gln Lys Asn Tyr Leu
 1               5                  10                  15

Ala

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR2 2E12

<400> SEQUENCE: 16

Trp Ala Ser Thr Arg Gly Ser
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: L-CDR3 2E12
```

```
<400> SEQUENCE: 17

Gln Gln Tyr Tyr Ser Tyr Pro Phe Thr
1               5
```